(12) United States Patent
Hauenstein et al.

(10) Patent No.: US 10,794,906 B2
(45) Date of Patent: *Oct. 6, 2020

(54) ASSAYS FOR DETECTING NEUTRALIZING AUTOANTIBODIES TO BIOLOGIC THERAPY

(71) Applicant: Prometheus Biosciences, Inc., San Diego, CA (US)

(72) Inventors: Scott Hauenstein, San Diego, CA (US); Linda Ohrmund, San Diego, CA (US); Sharat Singh, Rancho Santa Fe, CA (US); Shui Long Wang, San Diego, CA (US)

(73) Assignee: Prometheus Biosciences, Inc., San Diego, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 15/254,934

(22) Filed: Sep. 1, 2016

(65) Prior Publication Data

US 2017/0176433 A1    Jun. 22, 2017

Related U.S. Application Data

(63) Continuation of application No. 14/144,261, filed on Dec. 30, 2013, now Pat. No. 9,465,027, which is a continuation of application No. PCT/US2012/045794, filed on Jul. 6, 2012.

(60) Provisional application No. 61/505,031, filed on Jul. 6, 2011, provisional application No. 61/528,072, filed on Aug. 26, 2011, provisional application No. 61/535,884, filed on Sep. 16, 2011.

(51) Int. Cl.
| | |
|---|---|
| *G01N 33/564* | (2006.01) |
| *G01N 33/53* | (2006.01) |
| *B01D 15/34* | (2006.01) |
| *G01N 33/68* | (2006.01) |

(52) U.S. Cl.
CPC ........... *G01N 33/564* (2013.01); *B01D 15/34* (2013.01); *G01N 33/5308* (2013.01); *G01N 33/6854* (2013.01); *G01N 2333/525* (2013.01)

(58) Field of Classification Search
None
See application file for complete search history.

(56) References Cited

U.S. PATENT DOCUMENTS

| | | |
|---|---|---|
| 286,774 A | 10/1883 | Brinton |
| 4,459,359 A | 7/1984 | Neurath |
| 4,857,456 A | 8/1989 | Urist |
| 4,965,069 A | 10/1990 | Quash et al. |
| 5,094,740 A | 3/1992 | Brandley et al. |
| 5,223,395 A | 6/1993 | Gero |
| 5,231,024 A | 7/1993 | Moeller et al. |
| 5,582,998 A | 12/1996 | Adolf et al. |
| 5,698,419 A | 12/1997 | Wolpe et al. |
| 5,795,967 A | 8/1998 | Aggarwal et al. |
| 5,837,242 A | 11/1998 | Holliger et al. |
| 6,284,471 B1 | 9/2001 | Le et al. |
| 6,309,888 B1 | 10/2001 | Holvoet et al. |
| 6,444,461 B1 | 9/2002 | Knapp et al. |
| 6,903,183 B1 | 6/2005 | Stocco et al. |
| 6,906,183 B2 | 6/2005 | Romisch |
| 7,189,515 B2 | 3/2007 | Buechler et al. |
| 7,276,477 B2 | 10/2007 | Osslund et al. |
| 7,524,502 B2 | 4/2009 | Hellendoorn et al. |
| 7,542,502 B2 | 4/2009 | Hellendoorn et al. |
| 7,601,335 B2 | 10/2009 | McCutcheon et al. |
| 7,611,702 B2 | 11/2009 | Fischkoff et al. |
| 7,662,569 B2 | 2/2010 | Targan et al. |
| 8,574,855 B2 | 11/2013 | Singh et al. |
| 8,865,417 B2 | 10/2014 | Singh et al. |
| 9,465,027 B2 | 10/2016 | Hauenstein et al. |

(Continued)

FOREIGN PATENT DOCUMENTS

| | | |
|---|---|---|
| CN | 102695955 A | 9/2012 |
| CN | 103782172 A | 5/2014 |

(Continued)

OTHER PUBLICATIONS

Svenson et al., Monitoring patients treated with anti-TNF-α biopharmaceuticals: assessing serum infliximab and anti-infliximab antibodies, Rheumatology, 46, (2007), p. 1828-1834 (Year: 2007).*

(Continued)

*Primary Examiner* — Ellen J Marcsisin
(74) *Attorney, Agent, or Firm* — Wilson Sonsini Goodrich & Rosati

(57) ABSTRACT

The present invention provides assays for detecting and measuring the presence or level of neutralizing and non-neutralizing autoantibodies to biologics such as anti-TNFα drug therapeutics in a sample. The present invention is useful for monitoring the formation of neutralizing and/or non-neutralizing anti-drug antibodies over time while a subject is on biologic therapy. The present invention is also useful for predicting and/or determining the cross-reactivity of neutralizing anti-drug antibodies in a subject's sample with alternative biologic therapies. As such, the present invention provides information for guiding treatment decisions for those subjects receiving therapy with a biologic agent and improves the accuracy of optimizing therapy, reducing toxicity, and/or monitoring the efficacy of therapeutic treatment to biologic therapy.

15 Claims, 26 Drawing Sheets

(15 of 26 Drawing Sheet(s) Filed in Color)

(56) References Cited

U.S. PATENT DOCUMENTS

| | | |
|---|---|---|
| 9,506,920 B2 | 11/2016 | Singh et al. |
| 9,784,748 B2 | 10/2017 | Wang et al. |
| 10,386,366 B2 | 8/2019 | Singh et al. |
| 10,422,807 B2 | 9/2019 | Salbato et al. |
| 2002/0182651 A1 | 12/2002 | Patricelli |
| 2003/0040027 A1 | 2/2003 | Ritter et al. |
| 2003/0077246 A1 | 4/2003 | Welcher et al. |
| 2003/0109691 A1 | 6/2003 | Arnaout et al. |
| 2004/0022792 A1 | 2/2004 | Klinke et al. |
| 2004/0157782 A1 | 8/2004 | Doronina |
| 2005/0054005 A1* | 3/2005 | Ellis ............... G01N 33/564 435/7.1 |
| 2005/0181483 A1 | 8/2005 | Sawyer et al. |
| 2006/0003384 A1 | 1/2006 | Wagner et al. |
| 2006/0078944 A1 | 4/2006 | Kuai et al. |
| 2006/0110407 A1 | 5/2006 | Stopera et al. |
| 2006/0240480 A1 | 10/2006 | Curdt et al. |
| 2006/0253263 A1 | 11/2006 | Meshkin |
| 2007/0077249 A1 | 4/2007 | Silence et al. |
| 2008/0280311 A1* | 11/2008 | Strohner .......... G01N 33/54306 435/7.94 |
| 2008/0286774 A1 | 11/2008 | Turteltaub et al. |
| 2009/0035216 A1 | 2/2009 | Svenson et al. |
| 2009/0162374 A1 | 6/2009 | Geraghty et al. |
| 2009/0234202 A1 | 9/2009 | Goix et al. |
| 2009/0275496 A1 | 11/2009 | Baldwin et al. |
| 2010/0130367 A1 | 5/2010 | Murthy et al. |
| 2010/0330156 A1 | 12/2010 | Liu |
| 2012/0329172 A1 | 12/2012 | Singh et al. |
| 2013/0266963 A1 | 10/2013 | Hauenstein et al. |
| 2013/0295685 A1 | 11/2013 | Singh et al. |
| 2013/0344621 A1 | 12/2013 | Wang et al. |
| 2014/0045276 A1 | 2/2014 | Singh et al. |
| 2014/0051184 A1 | 2/2014 | Singh et al. |
| 2014/0057367 A1 | 2/2014 | Singh et al. |
| 2014/0135483 A1 | 5/2014 | Seito et al. |
| 2014/0186973 A1 | 7/2014 | Hauenstein et al. |
| 2015/0024404 A1 | 1/2015 | Singh et al. |
| 2016/0295685 A1 | 10/2016 | Ryu et al. |
| 2017/0184588 A1 | 6/2017 | Singh et al. |
| 2017/0328923 A1 | 11/2017 | Salbato et al. |
| 2019/0331694 A1 | 10/2019 | Arch et al. |
| 2019/0343425 A1 | 11/2019 | Jones et al. |

FOREIGN PATENT DOCUMENTS

| | | |
|---|---|---|
| EP | 0440044 | 8/1991 |
| EP | 0492448 A1 | 7/1992 |
| EP | 0642021 A2 | 3/1995 |
| EP | 0882984 A1 | 12/1998 |
| EP | 1237926 B1 | 9/2002 |
| EP | 1637601 A2 | 3/2006 |
| EP | 1769244 | 4/2007 |
| EP | 1902320 | 3/2008 |
| EP | 1237926 B1 | 6/2009 |
| EP | 2 676 137 | 12/2014 |
| JP | H05-066222 A2 | 1/1993 |
| JP | 05-066222 A2 | 3/1993 |
| JP | H07-110331 A2 | 4/1995 |
| JP | 7-140144 | 6/1995 |
| JP | H11-500607T A | 1/1999 |
| JP | 2001-249127 A2 | 9/2001 |
| JP | 2007-147367 | 6/2007 |
| JP | 2011254179 A | 12/2011 |
| JP | 2013-508739 | 3/2013 |
| JP | 2013545438 A | 12/2013 |
| JP | 2014515763 A | 7/2014 |
| JP | 2014525036 A | 9/2014 |
| WO | WO-9410308 A1 | 5/1994 |
| WO | 96/020219 A1 | 7/1996 |
| WO | WO-02081518 A2 | 10/2002 |
| WO | 2005/019271 A1 | 3/2005 |
| WO | WO-2005072340 A2 | 8/2005 |
| WO | 2006/004958 A2 | 1/2006 |
| WO | 2007/009469 A2 | 1/2007 |
| WO | WO-2009012140 A2 | 1/2009 |
| WO | WO-2009012140 A3 | 3/2009 |
| WO | 2009/091240 A1 | 7/2009 |
| WO | 2011/056590 A1 | 5/2011 |
| WO | WO-2012032181 A2 | 3/2012 |
| WO | 2012/054532 A1 | 4/2012 |
| WO | 2012/154253 A1 | 11/2012 |
| WO | WO-2012151247 A2 | 11/2012 |
| WO | 2013/006810 A1 | 1/2013 |
| WO | 2014/083520 A1 | 6/2014 |
| WO | WO-2016088104 A2 | 6/2016 |

OTHER PUBLICATIONS

Benucci, M. et al., "No correlations between the development of specific IgA and IgM antibodies against anti-TNF blocking agents, disease activity and adverse side reactions in patients with Rheumatoid arthritis," The Open Rheumatology Journal, 7:75-80, 2013.

English Machine Translation of CN 103782172 A; published May 7, 2014, 47 pages.

English Machine Translation of JP 07-140144; published Jun. 2, 1995, abstract only, 1 page.

English Machine Translation of JP 2013-508739; published May 7, 2013, 53 pages.

Aarden, L. et al., "Immunogenicity of anti-tumor necrosis factor antibodies—toward improved methods of anti-antibody measurement," Current Opinion in Immunology, 20(4): 431-435, 2008.

Arcangelo & Peterson, Pharmacotherapeutics for Advanced Practice: A Practical Approach, Philadelphia, PA, 536:18, 2006.

Aybay, C. et al., "Demonstration of specific antibodies against infliximab induced during treatment of a patient with ankylosing spondylitis," Rheumatology International, Clin. and Exper. Invest., 26(5):473-480, 2006.

Bendtzen, K. et al., "Individualized monitoring of drug bioavailability and immunogenicity in rheumatoid arthritis patients treated with the tumor necrosis factor alpha inhibitor infliximab," Arthritis & Rheumatism, 54(12):3782-3789, 2006.

Brekke, O. et al., "Therapeutic antibodies for human diseases at the dawn of the twenty-first century," Nature Reviews Drug Discovery, 2:52-62, 2003.

Bourdage et al., "An affinity capture elution (ACE) assay for detection of anti-drug antibody to monoclonal antibody therapeutics in the presence of high levels of drug," J. Immunol. Methods, 327(1-2):10-17, 2007.

Cheifetz, A. et al., "Monoclonal antibodies: immunogenicity, and associated infusion reactions," Mount Sinai J. Medicine, 72(4):250-256, 2005.

Chernesky & Mahony, "Immunoassays: principles and assay design," in Virology Methods Manuals, Mahy & Kangro (Eds.), pp. 123-124, San Diego, CA: Academic Press Inc., 1996.

Cisbio Bioassays, "HTRF human kappa and lambda MAb assay: A new solution for human IgG characterisation," 2009, URL: http://www.biolab.cn/plus/view-241835-1.html, Accessed on Feb. 20, 2014.

Deventer, S. et al., "Anti-tumour necrosis factor therapy in Crohn's disease: Where are we now?" Gut, 51(3):362-63, 2002.

Elliott, M. et al., "Repeated therapy with monoclonal antibody to tumour necrosis factor alpha (cA2) in patients with rheumatoid arthritis," Lancet, 334(8930):1125-1127, 1994.

Finckh et al., "Influence of anti-infliximab antibodies and residual infliximab concentrations on the occurrence of acquired drug resistance to infliximab in rheumatoid patients," Joint Bone Spine, 77:313-318, 2010.

Flood, J., "Tumor necrosis factor inhibitors in the treatment of chronic inflammatory diseases: A review of immunogenicity and potential implications," Suppl. to Managed Care, 18(4):1-5, 2009.

Gisbert, Javier et al., "Loss of Response and Requirement of Infliximab Dose Intensification in Crohn's Disease: A Review," Journal of Gastroenterology, 104:760-767, 2009.

Hagg, D. et al., "Measurement and biological correlates of antibody bioactivity during antibody immunotherapies," J. Immunol. Meth., 219(1-2): 7-21, 1998.

(56) References Cited

OTHER PUBLICATIONS

Harlow, E. and Lane, D., "Antibodies: A Laboratory Manual," Cold Spring Harbor Laboratory Press, Cold Spring Harbor, NY, pp. 7-10, 1988.

Harris, Quantitative Chemical Analysis, Sixth Ed., New York, W.H. Freeman Co., p. 85-86, 2003.

Harris, Quantitative Chemical Analysis, Sixth Ed., New York, W.H. Freeman Co., p. 91, 2003.

Holmskov-Nielsen, U. et al., "Immune complex formation analysed by high-performance size exclusion chromatography (HPLC-SEC) using either 125I-labelled antigen or enzyme-linked immunosorbent assay (ELISA) for detection," Immunology, 51(4):809-14, 1984.

Hosono, M. et al., "Human-mouse chimeric antibodies show low reactivity with human anti-murine antibodies HAMA," British J. Cancer, 65(2):197-200, 1992.

Invitrogen, "Looking on the bright side with Alexa Fluor® secondary antibodies," 2008, URL http://www.jimmunol.org/content/181/3/local/advertising.pdf, retrieved on Oct. 11, 2013.

Kawate, T. et al., "Fluorescence-detection size-exclusion chromatography for precrystallization screening of integral membrane proteins," Structure, 14:673-681, 2006.

Koren et al., "Recommendations on risk-based strategies for detection and characterization of antibodies against biotechnology products," Journal of Immunological Methods, 333:1-9, 2008.

Lofgren, J. et al., "Detection of neutralizing anti-therapeutic protein antibodies in serum or plasma samples containing high levels of the therapeutic protein," J. Immunol. Meth., 308(1-2):101-108, 2006.

Maier, K. et al., "Fluorescent HPLC assay for 20-HETE and other P-450 metabolites of arachidonic acid," A. J. Physiol. Heart Circ. Physiol., 279:H865-H871, 2000.

Molecular Probes, Inc., "BioParticles® Fluorescent Particles and Opsonizing Reagents," Product Information, Mar. 9, 2001, pp. 1-3, retrieved online from http://tools.lifetechnologies.com/content/sfs/manuals/mp02701.pdf on Aug. 12, 2014.

Murtazina, N.R. et al., "Immunochemical detection of sulfamethazine in river water and medicines," Chemotherapeutic Magazine, 39(8):93-97, 2005.

O'Keefe, Michael, Ed., Residue Analysis in Food Principles and Applications, Amsterdam, Hardwood Academic Publishers, p. 20, 2000.

Palframan R. et al., "Use of biofluorescence imaging to compare the distribution of certolizumab pegol, adalimumab, and infliximab in the inflamed paws of mice with collagen-induced arthritis," J. Immunol. Methods., 348(1-2):36-41, 2009.

Panchuk-Voloshina, N. et al., "Alexa dyes, a series of new fluorescent dyes that yield exceptionally bright, photostable conjugates," J. Histochem & Cytochem., 47(9):1179-1188, 1999.

Patton et al., "An acid dissociation bridging ELISA for detection of antibodies directed against therapeutic proteins in the presence of antigen," J. Immunol. Meth., 304(1-2):189-195, 2005.

Reynolds, J.C. et al., "Anti-murine antibody response to mouse monoclonal antibodies: Clinical findings and implications," Int'l. J. Radiation Applications and Instrumentation, Part B: Nuclear Medicine and Biology, 16(2):121-125, 1989.

Rojas, J.R. et al., "Formation, distribution, and elimination of infliximab and anti-infliximab immune complexes in cynomolgus monkeys," JPET, 313(2):578-585, 2005.

Scallon, B. et al., "Binding and functional comparisons of two types of tumor necrosis factor antagonists," J. Pharmacol. Exper. Ther., 301(2):418-426, 2002.

Sickert, D. et al., "Improvement of drug tolerance in immunogenicity testing by acid treatment on Biacore," J. Immunol. Meth., 334(1-2):29-36, 2008.

Smith et al., "Detection of antibodies against therapeutic proteins in the presence of residual therapeutic protein using a solid-phase extraction with acid dissociation (SPEAD) sample treatment prior to ELISA," Regulatory Toxicology and Pharmacology, 49(3): 230-237, 2007.

Steenholdt, C. et al. "Measurement of infliximab and anti-infliximab antibody levels can help distinguish maintenance versus loss of response," Gastroenterology & Hepatology, 8(2):131-134, 2012.

Svenson, M. et al., "Monitoring patients treated with anti-TNFα biopharmaceuticals: assessing serum infliximab and anti-infliximab antibodies," Rheumatology, 46:1828-34, 2007.

Tayyab, S. et al., "Size exclusion chromatography and size exclusion HPLC of proteins," Biochemical Education, 19(3):149-152, 1991.

Tiittanen, M. et al., "Anti-insulin activity in IgG-fractions from children with newly-diagnosed type 1 diabetes and negative for insulin autoantibodies," Autoimmunity, 37(I): 45-9, 2004.

U.S. Department of Health and Human Services et al., "Guidance for industry assay development for immunogenicity testing of therapeutic proteins," Draft Guidance, 2009, 24 pages, retrieved from <http://www.fda.gov/Drugs/GuidanceComplianceRegulatoryInformation/Guidances/UCM192750.

Van Der Laken, C. et al., "Imaging and serum analysis of immune complex formation of radiolabeled infliximab and anti-infliximab in responders and non-responders to therapy for rheumatoid arthritis," Ann. Rheum. Dis., 66(2):253-256, 2007.

Van Schouwenburg, P. et al., "A novel method for the detection of antibodies to adalimumab in the presence of drug reveals "hidden" immunogenicity in rheumatoid arthritis patients," J. Immunol. Meth., 362(1-2):82-88, 2010.

Wang, S. et al., "Analysis of anti-drug antibodies (ADA) to adalimumab in patient serum using a novel homogeneous mobility shift assay," Am. J. Gastro., 105(Suppl. 1): S444-S445, 2010.

Arends et al.: The formation of autoantibodies and antibodies to TNF-α blocking agents in relation to clinical response in patients with ankylosing spondylitis; Clinical and Experimental Rheumatology; 28(5):661-8 (2010).

Apostolovic et al.: Coiled coils: attractive protein folding motifs for the fabrication of self-assembled, responsive and bioactive materials. Chemical Society Reviews. 39(9):3541 (2010).

Clark, K. et al., Production of recombinant soluble human integrin α4β1. FEBS Letters 471:182-186 (2000).

European Patent Application No. 19163825.3 European Search Report dated Jun. 7, 2019, (10 pages).

International Application No. PCT/IB2015/058048 International Search Report and Written Opinion dated Apr. 28, 2016, (7 pages).

Kim, M. et al., Comparative analyses of complex formation and binding sites between Human Tumor Necrosis Factor-alpha and its three antagonists elucidate their different neutralizing mechanisms. J. Mol. Biol. 374:1374-1388 (2007).

Salbato, J. et al., Tu1301 validation of a homogenous mobility shift assay (HMSA) for the measurement of vedolizumab (VLM) and anti-VLM antibodies in inflammatory bowel disease (IBD) patient serum. Gastroenterology 148(4):S-852 (2015).

Santora, L. et al., Characterization of noncovalent complexes of recombinant human monoclonal antibody and antigen using cation exchange, size exclusion chromatography, and BIAcore. Analytical Biochemistry 299:119-129 (2001).

Wang, S. et al., Development and validation of a homogeneous mobility shift assay for the measurement of infliximab and antibodies-to-infliximab levels in patient serum. Journal of Immunological Methods 382:177-188 (2012).

Wang, S. et al., Monitoring of adalimumab and antibodies-to-adalimumab levels in patient serum by the homogeneous mobility shift assay. Journal of Pharmaceutical and Biomedical Analysis 78-79:39-44 (2013).

Yu et al.: Structural specializations of [alpha] 4 [beta] 7, an integrin that mediates rolling adhesion. The Journal of Cell Biology. 196(1):131-146 (2012).

* cited by examiner

Binding (non-NAB) Antibody

Neutralizing Antibody (NAB)

ASSAYS FOR DETECTING NEUTRALIZING AUTOANTIBODIES TO BIOLOGIC THERAPY

CROSS-REFERENCES TO RELATED APPLICATIONS

This application is a continuation of Ser. No. 14/144,261, filed Dec. 30, 2013 which is a continuation of PCT/US2012/045794, filed Jul. 6, 2012, which claims priority to U.S. Provisional Application No. 61/505,031, filed Jul. 6, 2011, U.S. Provisional Application No. 61/528,072, filed Aug. 26, 2011, and U.S. Provisional Application No. 61/535,884, filed Sep. 16, 2011, the disclosures of which are hereby incorporated by reference in their entirety for all purposes.

BACKGROUND OF THE INVENTION

Autoimmune disorders are a significant and widespread medical problem. For example, rheumatoid arthritis (RA) is an autoimmune disease affecting more than two million people in the United States. RA causes chronic inflammation of the joints and typically is a progressive illness that has the potential to cause joint destruction and functional disability. The cause of rheumatoid arthritis is unknown, although genetic predisposition, infectious agents and environmental factors have all been implicated in the etiology of the disease. In active RA, symptoms can include fatigue, lack of appetite, low grade fever, muscle and joint aches and stiffness. Also during disease flare ups, joints frequently become red, swollen, painful and tender, due to inflammation of the synovium. Furthermore, since RA is a systemic disease, inflammation can affect organs and areas of the body other than the joints, including glands of the eyes and mouth, the lung lining, the pericardium, and blood vessels.

Traditional treatments for the management of RA and other autoimmune disorders include fast acting "first line drugs" and slower acting "second line drugs." The first line drugs reduce pain and inflammation. Example of such first line drugs include aspirin, naproxen, ibuprofen, etodolac and other non-steroidal anti-inflammatory drugs (NSAIDs), as well as corticosteroids, given orally or injected directly into tissues and joints. The second line drugs promote disease remission and prevent progressive joint destruction and are also referred to as disease-modifying anti-rheumatic drugs or DMARDs. Examples of second line drugs include gold, hydrochloroquine, azulfidine and immunosuppressive agents, such as methotrexate, azathioprine, cyclophosphamide, chlorambucil and cyclosporine. Many of these drugs, however, can have detrimental side-effects. Thus, additional therapies for rheumatoid arthritis and other autoimmune disorders have been sought.

Tumor necrosis factor alpha (TNF-α) is a cytokine produced by numerous cell types, including monocytes and macrophages, that was originally identified based on its ability to induce the necrosis of certain mouse tumors. Subsequently, a factor termed cachectin, associated with cachexia, was shown to be identical to TNF-α. TNF-α has been implicated in the pathophysiology of a variety of other human diseases and disorders, including shock, sepsis, infections, autoimmune diseases, RA, Crohn's disease, transplant rejection and graft-versus-host disease.

Because of the harmful role of human TNF-α (hTNF-α) in a variety of human disorders, therapeutic strategies have been designed to inhibit or counteract hTNF-α activity. In particular, antibodies that bind to, and neutralize, hTNF-α have been sought as a means to inhibit hTNF-α activity.

Some of the earliest of such antibodies were mouse monoclonal antibodies (mAbs), secreted by hybridomas prepared from lymphocytes of mice immunized with hTNF-α (see, e.g., U.S. Pat. No. 5,231,024 to Moeller et al.). While these mouse anti-hTNF-α antibodies often displayed high affinity for hTNF-α and were able to neutralize hTNF-α activity, their use in vivo has been limited by problems associated with the administration of mouse antibodies to humans, such as a short serum half-life, an inability to trigger certain human effector functions, and elicitation of an unwanted immune response against the mouse antibody in a human (the "human anti-mouse antibody" (HAMA) reaction).

More recently, biological therapies have been applied to the treatment of autoimmune disorders such as rheumatoid arthritis. For example, four TNFα inhibitors, REMICADE™ (infliximab), a chimeric anti-TNFα mAb, ENBREL™ (etanercept), a TNFR-Ig Fc fusion protein, HUMIRA™ (adalimumab), a human anti-TNFα mAb, and CIMZIA® (certolizumab pegol), a PEGylated Fab fragment, have been approved by the FDA for treatment of rheumatoid arthritis. CIMZIA® is also used for the treatment of moderate to severe Crohn's disease (CD). While such biologic therapies have demonstrated success in the treatment of rheumatoid arthritis and other autoimmune disorders such as CD, not all subjects treated respond, or respond well, to such therapy. Moreover, administration of TNFα inhibitors can induce an immune response to the drug and lead to the production of autoantibodies such as human anti-chimeric antibodies (HACA), human anti-humanized antibodies (HAHA), and human anti-mouse antibodies (HAMA). Such HACA, HAHA, or HAMA immune responses can be associated with hypersensitive reactions and dramatic changes in pharmacokinetics and biodistribution of the immunotherapeutic TNFα inhibitor that preclude further treatment with the drug. Thus, there is a need in the art for assays to detect the presence of autoantibodies to biologic agents such as anti-TNFα drugs in a patient sample to monitor biologic therapy and to guide treatment decisions. The present invention satisfies this need and provides related advantages as well.

BRIEF SUMMARY OF THE INVENTION

The present invention provides assays for detecting and measuring the presence or level of neutralizing and non-neutralizing autoantibodies to biologics such as anti-TNFα drug therapeutics in a sample. The present invention is useful for monitoring the formation of neutralizing and/or non-neutralizing anti-drug antibodies over time while a subject is on biologic therapy (e.g., anti-TNFα drug therapy). The present invention is also useful for predicting and/or determining the cross-reactivity of neutralizing anti-drug antibodies in a subject's sample with alternative biologic therapies (e.g., alternative anti-TNFα therapies). As such, the present invention provides information for guiding treatment decisions for those subjects receiving therapy with a biologic agent and improves the accuracy of optimizing therapy, reducing toxicity, and/or monitoring the efficacy of therapeutic treatment to biologic therapy.

In one aspect, the present invention provides a method for detecting the presence of a neutralizing and/or non-neutralizing form of an autoantibody to a biologic in a sample, the method comprising:
  (a) contacting the sample with a labeled biologic and a labeled biologic binding moiety to form:
    (i) a first labeled complex (i.e., immuno-complex or conjugate) of the labeled biologic and the autoantibody (i.e., wherein the components of the first labeled complex are not covalently attached to each other); and/or (ii) a second labeled complex (i.e., immuno-complex or conjugate) of the labeled biologic, the labeled biologic binding moiety, and the autoantibody (i.e., wherein the components of the second labeled complex are not covalently attached to each other);

(b) subjecting the first labeled complex and/or the second labeled complex to size exclusion chromatography to separate them from free (i.e., unbound) labeled biologic binding moiety, free labeled biologic, and/or a complex of labeled biologic and labeled biologic binding moiety;

(c) measuring the level of free labeled biologic binding moiety after size exclusion chromatography (e.g., by measuring the area under the curve (AUC) of the free labeled biologic binding moiety peak following size exclusion chromatography (SEC)); and (d) comparing the level of the free labeled biologic binding moiety measured in step (c) to the level of free labeled biologic binding moiety in a control sample (e.g., by measuring the AUC of the free labeled biologic binding moiety peak following SEC of a reference sample containing only free labeled biologic binding moiety), thereby detecting the presence of a neutralizing and/or non-neutralizing form of the autoantibody.

In certain embodiments, a neutralizing form of the autoantibody is detected when the level of the free labeled biologic binding moiety measured in step (c) is the same or substantially the same as the level of the free labeled biologic binding moiety in the control sample. In certain other embodiments, a non-neutralizing form of the autoantibody is detected when the level of the free labeled biologic binding moiety measured in step (c) is decreased (e.g., substantially decreased) or absent (e.g., undetectable) compared to the level of the free labeled biologic binding moiety in the control sample.

In another aspect, the present invention provides a method for measuring the level or percent of a neutralizing form of an autoantibody to a biologic in a sample, the method comprising:

(a) contacting the sample with a labeled biologic and a labeled biologic binding moiety to form:

(i) a first labeled complex (i.e., immuno-complex or conjugate) of the labeled biologic and the autoantibody (i.e., wherein the components of the first labeled complex are not covalently attached to each other); and/or (ii) a second labeled complex (i.e., immuno-complex or conjugate) of the labeled biologic, the labeled biologic binding moiety, and the autoantibody (i.e., wherein the components of the second labeled complex are not covalently attached to each other);

(b) subjecting the first labeled complex and/or the second labeled complex to size exclusion chromatography to separate them from free (i.e., unbound) labeled biologic binding moiety, free labeled biologic, and/or a complex of labeled biologic and labeled biologic binding moiety;

(c) measuring the level of free labeled biologic binding moiety after size exclusion chromatography (e.g., by measuring the area under the curve (AUC) of the free labeled biologic binding moiety peak following size exclusion chromatography (SEC)); and (d) comparing the level of free labeled biologic binding moiety measured in step (c) to a normalized level or percent of free labeled biologic binding moiety in a control sample (e.g., by measuring and normalizing the AUC of the free labeled biologic binding moiety peak following SEC of a reference sample containing only free labeled biologic binding moiety to calculate the level or percent of free labeled biologic binding moiety), wherein the normalized level or percent of the free labeled biologic binding moiety in the control sample corresponds to the level or percent of a neutralizing form of the autoantibody.

In some embodiments, the difference between the normalized level or percent of the free labeled biologic binding moiety in the control sample and the level of free labeled biologic binding moiety measured in step (c) corresponds to the level or percent of a non-neutralizing form of the autoantibody.

In yet another aspect, the present invention provides a method for determining whether a neutralizing form of an autoantibody to a first biologic is cross-reactive with a second (i.e., different) biologic, the method comprising:

(a) detecting or measuring the presence, level, or percent of a neutralizing form of the autoantibody in a sample in accordance with an assay described herein to determine whether the sample is positive or negative for the neutralizing form of the autoantibody; and if the sample is positive for the neutralizing form of the autoantibody, then:

(b) contacting the sample with a labeled second biologic to form a labeled complex of the labeled second biologic and the neutralizing form of the autoantibody (i.e., wherein the components of the labeled complex are not covalently attached to each other);

(c) subjecting the labeled complex to size exclusion chromatography to separate the labeled complex (e.g., from free labeled second biologic); and (d) detecting the labeled complex, thereby determining whether a neutralizing form of an autoantibody to a first biologic is cross-reactive with a second biologic.

In certain embodiments, the presence of the labeled complex is an indication that the neutralizing autoantibody against the first biologic is cross-reactive with the second biologic, i.e., the neutralizing autoantibody will inhibit the activity of both the first and second biological drugs.

In certain other embodiments, the absence of the labeled complex is an indication that the neutralizing autoantibody against the first biologic is not cross-reactive with the second biologic, i.e., the neutralizing autoantibody will not inhibit the activity of the second biological drug.

In some embodiments, the biologic includes antibodies (e.g., anti-TNFα monoclonal antibodies), antibody fragments, proteins (e.g., cytokines such as interleukins), polypeptides, peptides, fusion proteins, multivalent binding proteins, antibody-drug conjugates, vaccines, nucleic acids, sugars, recombinant forms thereof, engineered forms thereof, and combinations thereof.

In other embodiments, the sample is a whole blood, serum, or plasma sample, e.g., from a subject receiving biologic therapy. In preferred embodiments, the sample is serum. In particular embodiments, the subject has a disease or disorder such as, e.g., an autoimmune disease (e.g., rheumatoid arthritis), an inflammatory disease (e.g., inflammatory bowel disease (IBD) such as Crohn's disease (CD) or ulcerative colitis (UC)), or cancer.

In certain embodiments, the sample has or is suspected of having an autoantibody to the biologic. In other embodiments, the biologic autoantibody includes, but is not limited to, human anti-chimeric antibodies (HACA), human anti-humanized antibodies (HAHA), and human anti-mouse antibodies (HAMA), as well as combinations thereof.

In certain aspects, the assay methods of the present invention further comprise an acid dissociation step comprising contacting a sample with an acid prior to, during, and/or after contacting the sample with a labeled biologic and a labeled biologic binding moiety.

In certain other aspects, the assay methods of the present invention comprise detecting the presence or level of one or more isotypes of a neutralizing and/or non-neutralizing form of an autoantibody to a biologic in a sample.

In one particular aspect, the present invention provides a method for detecting the presence of a neutralizing and/or non-neutralizing form of an autoantibody to an anti-TNFα drug in a sample, the method comprising:
(a) contacting the sample with a labeled anti-TNFα drug and a labeled TNFα to form:
    (i) a first labeled complex (i.e., immuno-complex or conjugate) of the labeled anti-TNFα drug and the autoantibody (i.e., wherein the components of the first labeled complex are not covalently attached to each other); and/or
    (ii) a second labeled complex (i.e., immuno-complex or conjugate) of the labeled anti-TNFα drug, the labeled TNFα, and the autoantibody (i.e., wherein the components of the second labeled complex are not covalently attached to each other);
(b) subjecting the first labeled complex and/or the second labeled complex to size exclusion chromatography to separate them from free (i.e., unbound) labeled TNFα, free labeled anti-TNFα drug, and/or a complex of labeled anti-TNFα drug and labeled TNFα;
(c) measuring the level of free labeled TNFα after size exclusion chromatography (e.g., by measuring the area under the curve (AUC) of the free labeled TNFα peak following size exclusion chromatography (SEC)); and
(d) comparing the level of the free labeled TNFα measured in step (c) to the level of free labeled TNFα in a control sample (e.g., by measuring the AUC of the free labeled TNFα peak following SEC of a reference sample containing only free labeled TNFα), thereby detecting the presence of a neutralizing and/or non-neutralizing form of the autoantibody.

In certain embodiments, a neutralizing form of the autoantibody is detected when the level of the free labeled TNFα measured in step (c) is the same or substantially the same as the level of the free labeled TNFα in the control sample. In certain other embodiments, a non-neutralizing form of the autoantibody is detected when the level of the free labeled TNFα measured in step (c) is decreased (e.g., substantially decreased) or absent (e.g., undetectable) compared to the level of the free labeled TNFα in the control sample.

In another particular aspect, the present invention provides a method for measuring the level or percent of a neutralizing form of an autoantibody to an anti-TNFα drug in a sample, the method comprising:
(a) contacting the sample with a labeled anti-TNFα drug and a labeled TNFα to form:
    (i) a first labeled complex (i.e., immuno-complex or conjugate) of the labeled anti-TNFα drug and the autoantibody (i.e., wherein the components of the first labeled complex are not covalently attached to each other); and/or
    (ii) a second labeled complex (i.e., immuno-complex or conjugate) of the labeled anti-TNFα drug, the labeled TNFα, and the autoantibody (i.e., wherein the components of the second labeled complex are not covalently attached to each other);
(b) subjecting the first labeled complex and/or the second labeled complex to size exclusion chromatography to separate them from free (i.e., unbound) labeled TNFα, free labeled anti-TNFα drug, and/or a complex of labeled anti-TNFα drug and labeled TNFα;
(c) measuring the level of free labeled TNFα after size exclusion chromatography (e.g., by measuring the area under the curve (AUC) of the free labeled TNFα peak following size exclusion chromatography (SEC)); and
(d) comparing the level of free labeled TNFα measured in step (c) to a normalized level or percent of free labeled TNFα in a control sample (e.g., by measuring and normalizing the AUC of the free labeled TNFα peak following SEC of a reference sample containing only free labeled TNFα to calculate the level or percent of free labeled TNFα), wherein the normalized level or percent of the free labeled TNFα in the control sample corresponds to the level or percent of a neutralizing form of the autoantibody.

In some embodiments, the difference between the normalized level or percent of the free labeled TNFα in the control sample and the level of free labeled TNFα measured in step (c) corresponds to the level or percent of a non-neutralizing form of the autoantibody.

In yet another particular aspect, the present invention provides a method for determining whether a neutralizing form of an autoantibody to a first anti-TNFα drug is cross-reactive with a second (i.e., different) anti-TNFα drug, the method comprising:
(a) detecting or measuring the presence, level, or percent of a neutralizing form of the autoantibody in a sample in accordance with an assay described herein to determine whether the sample is positive or negative for the neutralizing form of the autoantibody; and
if the sample is positive for the neutralizing form of the autoantibody, then:
(b) contacting the sample with a labeled second anti-TNFα drug to form a labeled complex of the labeled second anti-TNFα drug and the neutralizing form of the autoantibody (i.e., wherein the components of the labeled complex are not covalently attached to each other);
(c) subjecting the labeled complex to size exclusion chromatography to separate the labeled complex (e.g., from free labeled second anti-TNFα drug); and
(d) detecting the labeled complex, thereby determining whether a neutralizing form of an autoantibody to a first anti-TNFα drug is cross-reactive with a second anti-TNFα drug.

In certain embodiments, the presence of the labeled complex is an indication that the neutralizing autoantibody against the first anti-TNFα drug is cross-reactive with the second anti-TNFα drug, i.e., the neutralizing autoantibody will inhibit the activity of both the first and second anti-TNFα drugs.

In certain other embodiments, the absence of the labeled complex is an indication that the neutralizing autoantibody against the first anti-TNFα drug is not cross-reactive with the second anti-TNFα drug, i.e., the neutralizing autoantibody will not inhibit the activity of the second anti-TNFα drug.

In some embodiments, the anti-TNFα drug is selected from the group consisting of REMICADE™ (infliximab), ENBREL™ (etanercept), HUMIRA™ (adalimumab), CIMZIA® (certolizumab pegol), SIMPONI® (golimumab; CNTO 148), and combinations thereof.

In other embodiments, the sample is a whole blood, serum, or plasma sample, e.g., from a subject receiving anti-TNFα drug therapy. In preferred embodiments, the sample is serum. In particular embodiments, the subject has a TNFα-mediated disease or disorder such as, e.g., an autoimmune disease (e.g., rheumatoid arthritis) or an inflammatory disease (e.g., inflammatory bowel disease (IBD) such as Crohn's disease (CD) or ulcerative colitis (UC)).

In certain embodiments, the sample has or is suspected of having an autoantibody to the anti-TNFα drug. In other embodiments, the anti-TNFα drug autoantibody includes, but is not limited to, human anti-chimeric antibodies (HACA), human anti-humanized antibodies (HAHA), and human anti-mouse antibodies (HAMA), as well as combinations thereof.

In certain aspects, the assay methods of the present invention further comprise an acid dissociation step comprising contacting a sample with an acid prior to, during, and/or after contacting the sample with a labeled anti-TNFα drug and a labeled TNFα.

In certain other aspects, the assay methods of the present invention comprise detecting the presence or level of one or more isotypes of a neutralizing and/or non-neutralizing form of an autoantibody to an anti-TNFα drug in a sample.

In a further aspect, the present invention provides a method for monitoring and/or optimizing therapy to a biologic in a subject receiving a course of therapy with the biologic, the method comprising:
(a) detecting or measuring the presence, level, or percent of a neutralizing form of an autoantibody to the biologic in accordance with the assay described herein at a plurality of time points over the course of therapy;
(b) detecting a change in the presence, level, or percent of the neutralizing form of the autoantibody over time; and
(c) determining a subsequent dose of the course of therapy for the subject or whether a different course of therapy should be administered to the subject based upon the change in the presence, level, or percent of the neutralizing form of the autoantibody over time.

In one particular aspect, the present invention provides a method for monitoring and/or optimizing therapy to a biologic in a subject receiving a course of therapy with the biologic, the method comprising:
(a) measuring the level or percent of a neutralizing form of an autoantibody to the biologic in a first sample from the subject as described herein at time point $t_0$;
(b) measuring the level or percent of the neutralizing form of the autoantibody in a second sample from the subject as described herein at time point $t_1$;
(c) optionally repeating step (b) with n additional samples from the subject at time points $t_{n+1}$, wherein n is an integer from 1 to about 25 (e.g., n is 1, 2, 3, 4, 5, 6, 7, 8, 9, 10, 11, 12, 13, 14, 15, 16, 17, 18, 19, 20, 21, 22, 23, 24, or 25, or any range therein);
(d) detecting a change in the level or percent of the neutralizing form of the autoantibody from time points $t_0$ to $t_1$ or from time points $t_0$ to $t_{n+1}$; and
(e) determining a subsequent dose of the course of therapy for the subject or whether a different course of therapy should be administered to the subject based upon the change in the level or percent of the neutralizing form of the autoantibody over time.

In an additional aspect, the present invention provides a method for optimizing therapy and/or reducing toxicity in a subject receiving a course of therapy with a first biologic, the method comprising:
(a) determining whether a neutralizing form of an autoantibody to the first biologic is cross-reactive with a second (i.e., different) biologic by detecting or measuring the presence, level, or percent of a neutralizing form of the autoantibody in a sample from the subject in accordance with an assay described herein; and
(b) determining that a different course of therapy should be administered to the subject if the neutralizing form of the autoantibody is cross-reactive with the second biologic.

In one particular aspect, the present invention provides a method for monitoring and/or optimizing therapy to an anti-TNFα drug in a subject receiving a course of therapy with the anti-TNFα drug, the method comprising:
(a) detecting or measuring the presence, level, or percent of a neutralizing form of an autoantibody to the anti-TNFα drug in accordance with the assay described herein at a plurality of time points over the course of therapy;
(b) detecting a change in the presence, level, or percent of the neutralizing form of the autoantibody over time; and
(c) determining a subsequent dose of the course of therapy for the subject or whether a different course of therapy should be administered to the subject based upon the change in the presence, level, or percent of the neutralizing form of the autoantibody over time.

In another particular aspect, the present invention provides a method for monitoring and/or optimizing therapy to an anti-TNFα drug in a subject receiving a course of therapy with the anti-TNFα drug, the method comprising:
(a) measuring the level or percent of a neutralizing form of an autoantibody to the anti-TNFα drug in a first sample from the subject as described herein at time point $t_0$;
(b) measuring the level or percent of the neutralizing form of the autoantibody in a second sample from the subject as described herein at time point $t_1$;
(c) optionally repeating step (b) with n additional samples from the subject at time points $t_{n+1}$, wherein n is an integer from 1 to about 25 (e.g., n is 1, 2, 3, 4, 5, 6, 7, 8, 9, 10, 11, 12, 13, 14, 15, 16, 17, 18, 19, 20, 21, 22, 23, 24, or 25, or any range therein);
(d) detecting a change in the level or percent of the neutralizing form of the autoantibody from time points $t_0$ to $t_1$ or from time points $t_0$ to $t_{n+1}$; and
(e) determining a subsequent dose of the course of therapy for the subject or whether a different course of therapy should be administered to the subject based upon the change in the level or percent of the neutralizing form of the autoantibody over time.

In yet another particular aspect, the present invention provides a method for optimizing therapy and/or reducing toxicity in a subject receiving a course of therapy with a first anti-TNFα drug, the method comprising:
(a) determining whether a neutralizing form of an autoantibody to the first anti-TNFα drug is cross-reactive with a second (i.e., different) anti-TNFα drug by detecting or measuring the presence, level, or percent of a neutralizing form of the autoantibody in a sample from the subject in accordance with an assay described herein; and (b) determining that a different course of therapy should be administered to the subject if the neutralizing form of the autoantibody is cross-reactive with the second anti-TNFα drug.

Other objects, features, and advantages of the present invention will be apparent to one of skill in the art from the following detailed description and figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

I. Introduction

Figure 1:
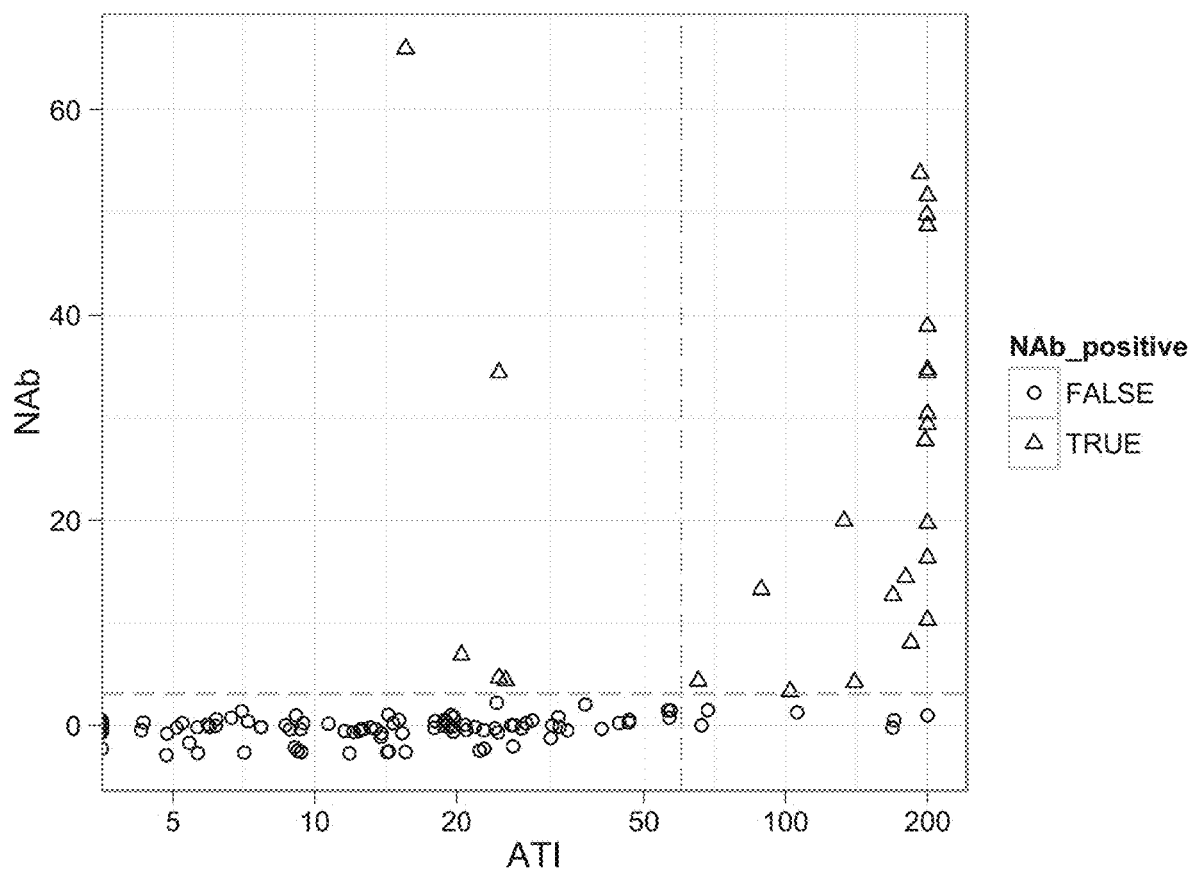
FIG. 1 illustrates that there was a clear relationship between NAb percent (y-axis) and ATI levels.

The present invention is based in part on the discovery that a homogeneous mobility shift assay using size exclusion chromatography and optionally acid dissociation to enable equilibration of immune complexes is particularly advantageous for measuring the presence or level of neutralizing and non-neutralizing forms of autoantibodies (e.g., HACA, HAHA, etc.) that are generated against biologics such as anti-TNFα drugs. Such autoantibodies are also known as anti-drug antibodies or ADA, and neutralizing and non-neutralizing forms thereof are also known as NAb and non-NAb, respectively.

In particular embodiments, the homogeneous mobility shift assays of the invention are performed by contacting a subject's sample with (e.g., fluorescently) labeled biologic (e.g., anti-TNFα drug) and (e.g., fluorescently) labeled biologic binding moiety (e.g., TNFα). The assays described herein are advantageous for at least the following reasons: they obviate the need for wash steps which remove low affinity ADA; they use distinct labels such as fluorophores that allow for detection on the visible, IR, and/or near IR (NIR) spectra which decreases background and serum interference issues; they increase the ability to detect neutralizing and/or non-neutralizing ADA in subjects with a low titer due to the high sensitivity of fluorescent label detection; and they occur as a liquid phase reaction, thereby reducing the chance of any changes in the epitope by attachment to a solid surface such as an ELISA plate.

In exemplary embodiments, the assays of the present invention are advantageous because they enable time course case studies of IBD subjects on anti-TNFα drug therapy for monitoring the formation of neutralizing and/or non-neutralizing anti-drug antibodies in multiple samples at different time points. The assays of the present invention are also advantageous because they enable the determination of whether there is a shift from non-neutralizing to neutralizing anti-drug antibodies over time while a subject is on anti-TNFα drug therapy. Without being bound to any particular theory, neutralizing anti-drug antibodies may have significant negative clinical consequences because they interfere with the binding between the anti-TNFα drug and TNFα, thereby inducing a loss of efficacy.

In additional exemplary embodiments, the assays of the present invention find utility in predicting and/or determining the cross-reactivity of neutralizing anti-drug antibodies in a subject's sample with alternative biological drugs such as other anti-TNF drugs. For illustration purposes only, if the sample contains neutralizing ADA to one anti-TNFα drug, these neutralizing ADA will likely cross-react and be neutralizing to other anti-TNFα drugs, such that the recommended treatment adjustment for the subject would be to switch to a drug with a different mechanism of action (e.g., a non-anti-TNF agent). However, if the sample contains non-neutralizing ADA to one anti-TNFα drug, the recommended treatment adjustment for the subject could be to switch to another anti-TNFα drug.

Accordingly, the present invention addresses and overcomes current limitations associated with the administration of anti-TNFα drugs, such as infliximab and adalimumab, in part, by providing information useful for guiding treatment decisions for those subjects receiving anti-TNFα drug therapy. The methods of the present invention are particularly useful for monitoring those subjects receiving an anti-TNFα drug to detect or measure the formation and/or development of neutralizing ADA (e.g., over time during a course of anti-TNFα drug therapy) and are also useful to detect or measure a change in (e.g., increase) the amount, percent, or ratio of neutralizing ADA compared to non-neutralizing ADA over time while a subject is on anti-TNFα drug therapy.

As such, the present invention provides methods for determining when and/or how (1) to adjust or modify (e.g., increase or decrease) the subsequent dose of an anti-TNFα drug to optimize therapeutic efficacy and/or to reduce toxicity in view of the presence, level, or percent of neutralizing ADA, (2) to combine an anti-TNFα drug (e.g., at an initial, increased, decreased, or same dose) with one or more immunosuppressive agents such as methotrexate (MTX) or azathioprine (AZA) in view of the presence, level, or percent of neutralizing ADA, and/or (3) to change the current course of therapy (e.g., switch to a different anti-TNFα drug or to a drug that targets a different mechanism) in view of the presence, level, or percent of neutralizing ADA. Such methods are useful for ensuring that subjects receiving anti-TNFα drugs are getting the right dose, that they are not developing an immune response against the drug, and that they should be switched to a different drug due to failure with the initial drug (e.g., development of cross-reactive neutralizing ADA against the initial anti-TNFα drug).

II. Definitions

As used herein, the following terms have the meanings ascribed to them unless specified otherwise.

The terms "biologic" or "biologic agent" or "biological drug" as used herein encompass products and substances produced from or extracted from a biological system (e.g., a living organism). Non-limiting examples of biologics include antibodies, antibody fragments, proteins, polypeptides, peptides, fusion proteins (e.g., Ig fusion proteins or Fc fusion proteins), multivalent binding proteins (e.g., DVD Ig), antibody-drug conjugates, vaccines, nucleic acids, sugars, recombinant forms thereof, engineered forms thereof, and combinations thereof.

The term "biologic binding moiety" includes any molecule, agent, or substance that (e.g., specifically) binds to or interacts with a biologic. In certain instances, a neutralizing form of the autoantibody interferes with the binding between the biologic binding moiety and the biologic. In certain other instances, a non-neutralizing form of the autoantibody does not interfere with the binding between the biologic binding moiety and the biologic. As one non-limiting example, the biologic binding moiety comprises TNFα when the biologic comprises an anti-TNFα drug. As another non-limiting example, the biologic binding moiety comprises an interleukin receptor (e.g., a soluble extracellular fragment of an interleukin receptor) when the biologic comprises an interleukin such as IL-2.

The terms "anti-TNFα drug" or "TNFα inhibitor" as used herein are intended to encompass agents including proteins, antibodies, antibody fragments, fusion proteins (e.g., Ig fusion proteins or Fc fusion proteins), multivalent binding proteins (e.g., DVD Ig), small molecule TNFα antagonists and similar naturally- or nonnaturally-occurring molecules, and/or recombinant and/or engineered forms thereof, that, directly or indirectly, inhibit TNFα activity, such as by inhibiting interaction of TNFα with a cell surface receptor for TNFα, inhibiting TNFα protein production, inhibiting TNFα gene expression, inhibiting TNFα secretion from cells, inhibiting TNFα receptor signaling or any other means resulting in decreased TNFα activity in a subject. The term "anti-TNFα drug" or "TNFα inhibitor" preferably includes agents which interfere with TNFα activity. Examples of anti-TNFα drugs include, without limitation, infliximab (REMICADE™, Johnson and Johnson), human anti-TNF monoclonal antibody adalimumab (D2E7/HUMIRA™, Abbott Laboratories), etanercept (ENBREL™, Amgen), certolizumab pegol (CIMZIA®, UCB, Inc.), golimumab (SIMPONI®; CNTO 148), CDP 571 (Celltech), CDP 870 (Celltech), as well as other compounds which inhibit TNFα activity, such that when administered to a subject suffering from or at risk of suffering from a disorder in which TNFα activity is detrimental (e.g., RA), the disorder is treated.

The term "TNFα" is intended to include a human cytokine that exists as a 17 kDa secreted form and a 26 kDa membrane associated form, the biologically active form of which is composed of a trimer of noncovalently bound 17 kDa molecules. The structure of TNFα is described further in, for example, Jones et al., *Nature,* 338:225-228 (1989). The term TNFα is intended to include human TNFα, a recombinant human TNFα (rhTNF-α), or TNFα that is at least about 80% identity to the human TNFα protein. Human TNFα consists of a 35 amino acid (aa) cytoplasmic domain, a 21 aa transmembrane segment, and a 177 aa extracellular domain (ECD) (Pennica, D. et al. (1984) *Nature* 312:724). Within the ECD, human TNFα shares 97% aa sequence identity with rhesus TNFα, and 71% to 92% aa sequence identity with bovine, canine, cotton rat, equine, feline, mouse, porcine, and rat TNFα. TNFα can be prepared by standard recombinant expression methods or purchased commercially (R & D Systems, Catalog No. 210-TA, Minneapolis, Minn.).

In certain embodiments, "TNFα" is an "antigen," which includes a molecule or a portion of the molecule capable of being bound by an anti-TNF-α drug. TNFα can have one or more than one epitope. In certain instances, TNFα will react, in a highly selective manner, with an anti-TNFα antibody. Preferred antigens that bind antibodies, fragments, and regions of anti-TNFα antibodies include at least 5 amino acids of human TNFα. In certain instances, TNFα is a sufficient length having an epitope of TNFα that is capable of binding anti-TNFα antibodies, fragments, and regions thereof.

The term "size exclusion chromatography" or "SEC" includes a chromatographic method in which molecules in solution are separated based on their size and/or hydrodynamic volume. It is applied to large molecules or macromolecular complexes such as proteins and their conjugates. Typically, when an aqueous solution is used to transport the sample through the column, the technique is known as gel filtration chromatography.

The terms "complex," "immuno-complex," "conjugate," and "immunoconjugate" include, but are not limited to, TNFα bound (e.g., by non-covalent means) to an anti-TNFα drug, an anti-TNFα drug bound (e.g., by non-covalent means) to an autoantibody against the anti-TNFα drug (e.g., a neutralizing or non-neutralizing anti-drug antibody), and an anti-TNFα drug bound (e.g., by non-covalent means) to both TNFα and an autoantibody against the anti-TNFα drug (e.g., a neutralizing or non-neutralizing anti-drug antibody).

As used herein, an entity that is modified by the term "labeled" includes any entity, molecule, protein, enzyme, antibody, antibody fragment, cytokine, or related species that is conjugated with another molecule or chemical entity that is empirically detectable. Chemical species suitable as labels for labeled-entities include, but are not limited to, fluorescent dyes, e.g. Alexa Fluor® dyes such as Alexa Fluor® 647, quantum dots, optical dyes, luminescent dyes, and radionuclides, e.g. $^{125}$I.

The phrase "fluorescence label detection" includes a means for detecting a fluorescent label. Means for detection include, but are not limited to, a spectrometer, a fluorimeter, a photometer, and a detection device commonly incorporated with a chromatography instrument such as, but not limited to, size exclusion-high performance liquid chromatography, such as, but not limited to, an Agilent-1200 HPLC System.

The phrase "optimize therapy" includes optimizing the dose (e.g., the effective amount or level) and/or the type of a particular therapy. For example, optimizing the dose of an anti-TNFα drug includes increasing or decreasing the amount of the anti-TNFα drug subsequently administered to a subject. In certain instances, optimizing the type of an anti-TNFα drug includes changing the administered anti-TNFα drug from one drug to a different drug (e.g., a different anti-TNFα drug or a drug that targets a different mechanism). In other instances, optimizing therapy includes co-administering a dose of an anti-TNFα drug (e.g., at an increased, decreased, or same dose as the previous dose) in combination with one or more immunosuppressive drugs.

The term "co-administer" includes to administer more than one active agent, such that the duration of physiological effect of one active agent overlaps with the physiological effect of a second active agent.

The term "subject," "patient," or "individual" typically includes humans, but also includes other animals such as, e.g., other primates, rodents, canines, felines, equines, ovines, porcines, and the like.

The term "course of therapy" includes any therapeutic approach taken to relieve or prevent one or more symptoms associated with a disease or disorder. The term encompasses administering any compound, drug, procedure, and/or regimen useful for improving the health of an individual with a disease or disorder and includes any of the therapeutic agents described herein. As a non-limiting example, the course of therapy or the dose of the current course of therapy can be changed (e.g., increased or decreased) based upon the presence or concentration level of TNFα, anti-TNFα drug, and/or anti-drug antibody (e.g., the presence, level, or percent of neutralizing and/or non-neutralizing anti-drug antibody determined using the methods of the invention).

The term "immunosuppressive drug" or "immunosuppressive agent" includes any substance capable of producing an immunosuppressive effect, e.g., the prevention or diminution of the immune response, as by irradiation or by administration of drugs such as anti-metabolites, anti-lymphocyte sera, antibodies, etc. Examples of immunosuppressive drugs include, without limitation, thiopurine drugs such as azathioprine (AZA) and metabolites thereof; anti-metabolites such as methotrexate (MTX); sirolimus (rapamycin); temsirolimus; everolimus; tacrolimus (FK-506); FK-778; anti-lymphocyte globulin antibodies, anti-thymocyte globulin antibodies, anti-CD3 antibodies, anti-CD4 antibodies, and antibody-toxin conjugates; cyclosporine; mycophenolate; mizoribine monophosphate; scoparone; glatiramer acetate; metabolites thereof; pharmaceutically acceptable salts thereof; derivatives thereof; prodrugs thereof; and combinations thereof.

The term "thiopurine drug" includes azathioprine (AZA), 6-mercaptopurine (6-MP), or any metabolite thereof that has therapeutic efficacy and includes, without limitation, 6-thioguanine (6-TG), 6-methylmercaptopurine riboside, 6-thioinosine nucleotides (e.g., 6-thioinosine monophosphate, 6-thioinosine diphosphate, 6-thioinosine triphosphate), 6-thioguanine nucleotides (e.g., 6-thioguanosine monophosphate, 6-thioguanosine diphosphate, 6-thioguanosine triphosphate), 6-thioxanthosine nucleotides (e.g., 6-thioxanthosine monophosphate, 6-thioxanthosine diphosphate, 6-thioxanthosine triphosphate), derivatives thereof, analogues thereof, and combinations thereof.

The term "sample" includes any biological specimen obtained from an individual. Samples include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), cellular extracts thereof, and an immunoglobulin enriched fraction derived from one or more of these bodily fluids or tissues. In some embodiments, the sample is whole blood, a fractional component thereof such as plasma, serum, or a cell pellet, or an immunoglobulin enriched fraction thereof. One skilled in the art will appreciate that samples such as serum samples can be diluted prior to the analysis. In certain embodiments, the sample is obtained by isolating PBMCs and/or PMN cells using any technique known in the art. In certain other embodiments, the sample is a tissue biopsy such as, e.g., from a site of inflammation such as a portion of the gastrointestinal tract or synovial tissue.

The steps of the methods of the present invention do not necessarily have to be performed in the particular order in which they are presented. A person of ordinary skill in the art would understand that other orderings of the steps of the methods of the invention are encompassed within the scope of the present invention.

Brackets, "[ ]" indicate that the species within the brackets are referred to by their concentration.

III. Description of the Embodiments

The present invention provides assays for detecting and measuring the presence or level of neutralizing and non-neutralizing autoantibodies to biologics such as anti-TNFα drug therapeutics in a sample. The present invention is useful for monitoring the formation of neutralizing and/or non-neutralizing anti-drug antibodies over time while a subject is on biologic therapy (e.g., anti-TNFα drug therapy). The present invention is also useful for predicting and/or determining the cross-reactivity of neutralizing anti-drug antibodies in a subject's sample with alternative biologic therapies (e.g., alternative anti-TNFα therapies). As such, the present invention provides information for guiding treatment decisions for those subjects receiving therapy with a biologic agent and improves the accuracy of optimizing therapy, reducing toxicity, and/or monitoring the efficacy of therapeutic treatment to biologic therapy.

In one aspect, the present invention provides a method for detecting the presence of a neutralizing and/or non-neutralizing form of an autoantibody to a biologic in a sample, the method comprising:
  (a) contacting the sample with a labeled biologic and a labeled biologic binding moiety to form:
    (i) a first labeled complex (i.e., immuno-complex or conjugate) of the labeled biologic and the autoantibody (i.e., wherein the components of the first labeled complex are not covalently attached to each other); and/or
    (ii) a second labeled complex (i.e., immuno-complex or conjugate) of the labeled biologic, the labeled biologic binding moiety, and the autoantibody (i.e., wherein the components of the second labeled complex are not covalently attached to each other);
  (b) subjecting the first labeled complex and/or the second labeled complex to size exclusion chromatography to separate them from free (i.e., unbound) labeled biologic binding moiety, free labeled biologic, and/or a complex of labeled biologic and labeled biologic binding moiety;
  (c) measuring the level of free labeled biologic binding moiety after size exclusion chromatography (e.g., by measuring the area under the curve (AUC) of the free labeled biologic binding moiety peak following size exclusion chromatography (SEC)); and
  (d) comparing the level of the free labeled biologic binding moiety measured in step (c) to the level of free labeled biologic binding moiety in a control sample (e.g., by measuring the AUC of the free labeled biologic binding moiety peak following SEC of a reference sample containing only free labeled biologic binding moiety), thereby detecting the presence of a neutralizing and/or non-neutralizing form of the autoantibody.

In some embodiments, a neutralizing form of the autoantibody interferes with the binding between the biologic and biologic binding moiety. In other embodiments, a non-neutralizing form of the autoantibody does not interfere with the binding between the biologic and biologic binding moiety.

In some instances, free labeled biologic binding moiety consists of labeled biologic binding moiety that is substantially free of bound biologic (e.g., labeled and/or unlabeled biologic).

In certain embodiments, a neutralizing form of the autoantibody is detected when the level of the free labeled biologic binding moiety measured in step (c) is the same or substantially the same as the level of the free labeled biologic binding moiety in the control sample. In certain other embodiments, a non-neutralizing form of the autoantibody is detected when the level of the free labeled biologic binding moiety measured in step (c) is decreased (e.g., substantially decreased) or absent (e.g., undetectable) compared to the level of the free labeled biologic binding moiety in the control sample.

In particular embodiments, the level of the free labeled biologic binding moiety measured in step (c) is considered to be substantially the same as the level of the free labeled biologic binding moiety in the control sample when it is at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% the level of the free labeled biologic binding moiety measured in the control sample. In particular embodiments, the level of the free labeled biologic binding moiety measured in step (c) is considered to be substantially decreased compared to the level of the free labeled biologic binding moiety in the control sample when it is at least about 50%, 55%, 60%, 65%, 70%, 75%, 80%, 85%, 90%, or 95% less than the level of the free labeled biologic binding moiety measured in the control sample.

In some embodiments, the level of free labeled biologic binding moiety is measured by integrating the area under the curve (AUC) of the free labeled biologic binding moiety peak from a plot of signal intensity as a function of elution time from the size exclusion chromatography (e.g., SEC-HPLC).

In some embodiments, the biologic includes antibodies (e.g., anti-TNFα monoclonal antibodies), antibody fragments, proteins (e.g., cytokines such as interleukins), polypeptides, peptides, fusion proteins, multivalent binding proteins, antibody-drug conjugates, vaccines, nucleic acids, sugars, recombinant forms thereof, engineered forms thereof, and combinations thereof.

In other embodiments, the sample is a whole blood, serum, or plasma sample, e.g., from a subject receiving biologic therapy. In preferred embodiments, the sample is serum. In particular embodiments, the subject has a disease or disorder such as, e.g., an autoimmune disease (e.g., rheumatoid arthritis), an inflammatory disease (e.g., inflammatory bowel disease (IBD) such as Crohn's disease (CD) or ulcerative colitis (UC)), or cancer.

In certain embodiments, the sample has or is suspected of having an autoantibody to the biologic. In other embodiments, the biologic autoantibody includes, but is not limited to, human anti-chimeric antibodies (HACA), human anti-humanized antibodies (HAHA), and human anti-mouse antibodies (HAMA), as well as combinations thereof.

In another aspect, the present invention provides a method for measuring the level or percent of a neutralizing form of an autoantibody to a biologic in a sample, the method comprising:
  (a) contacting the sample with a labeled biologic and a labeled biologic binding moiety to form:
    (i) a first labeled complex (i.e., immuno-complex or conjugate) of the labeled biologic and the autoantibody (i.e., wherein the components of the first labeled complex are not covalently attached to each other); and/or (ii) a second labeled complex (i.e., immuno-complex or conjugate) of the labeled biologic, the labeled biologic binding moiety, and the autoantibody (i.e., wherein the components of the second labeled complex are not covalently attached to each other);

(b) subjecting the first labeled complex and/or the second labeled complex to size exclusion chromatography to separate them from free (i.e., unbound) labeled biologic binding moiety, free labeled biologic, and/or a complex of labeled biologic and labeled biologic binding moiety;

(c) measuring the level of free labeled biologic binding moiety after size exclusion chromatography (e.g., by measuring the area under the curve (AUC) of the free labeled biologic binding moiety peak following size exclusion chromatography (SEC)); and (d) comparing the level of free labeled biologic binding moiety measured in step (c) to a normalized level or percent of free labeled biologic binding moiety in a control sample (e.g., by measuring and normalizing the AUC of the free labeled biologic binding moiety peak following SEC of a reference sample containing only free labeled biologic binding moiety to calculate the level or percent of free labeled biologic binding moiety), wherein the normalized level or percent of the free labeled biologic binding moiety in the control sample corresponds to the level or percent of a neutralizing form of the autoantibody.

In some embodiments, the difference between the normalized level or percent of the free labeled biologic binding moiety in the control sample and the level of free labeled biologic binding moiety measured in step (c) corresponds to the level or percent of a non-neutralizing form of the autoantibody.

In some instances, free labeled biologic binding moiety consists of labeled biologic binding moiety that is substantially free of bound biologic (e.g., labeled and/or unlabeled biologic).

In particular embodiments, the level or percent of the free labeled biologic binding moiety in a control sample is normalized by measuring the peak area (e.g., by measuring the AUC) of a complex formed between the labeled biologic and the labeled biologic binding moiety (e.g., "labeled complex"), and then subtracting the measured peak area of the labeled complex from the peak area of the free labeled biologic binding moiety (e.g., by measuring the AUC of the free labeled biologic binding moiety peak).

In certain embodiments, the level of the free labeled biologic binding moiety is measured by integrating the area under the curve (AUC) of the free labeled biologic binding moiety peak from a plot of signal intensity as a function of elution time from the size exclusion chromatography (e.g., SEC-HPLC). In other embodiments, the level of a complex formed between the labeled biologic and labeled biologic binding moiety is measured by integrating the AUC of the free labeled biologic binding moiety peak from a plot of signal intensity as a function of elution time from the size exclusion chromatography (e.g., SEC-HPLC).

In certain embodiments, a subpopulation of the autoantibody to a biologic (e.g., ADA) is a neutralizing form of the autoantibody (e.g., NAb). In some embodiments, the total level of an autoantibody to a biologic in a sample can be calculated by adding the levels of both neutralizing and non-neutralizing forms of the autoantibody measured in accordance with the methods of the invention.

In some embodiments, the level of the free labeled biologic binding moiety measured in step (c) is further compared to a negative control, a positive control, or a combination thereof. In further embodiments, the percent of the neutralizing form of the autoantibody (e.g., NAb) determined in step (d) is compared to a cutoff value or reference range established from a healthly control (e.g., normal human serum). In some embodiments, the cutoff value or reference range is expressed as a threshold percent of NAb that the sample must have in order to be considered positive for NAb. In such embodiments, the sample is positive for NAb when the percent of NAb determined in step (d) is greater than or equal to the cutoff value or reference range established from the healthly control. In other embodiments, the sample is negative for NAb when the percent of NAb determined in step (d) is less than the cutoff value or reference range established from the healthly control. Non-limiting examples of cutoff values or reference ranges include, e.g., at least about 0.25%, 0.50%, 0.75%, 1.00%, 1.50%, 2.00%, 2.50%, 2.60%, 2.70%, 2.80%, 2.90%, 3.00%, 3.01%, 3.02%, 3.03%, 3.04%, 3.05%, 3.06%, 3.07%, 3.08%, 3.09%, 3.10%, 3.20%, 3.30%, 3.40%, 3.50%, 4.00%, 4.50%, 5.00%, 5.50%, 6.00%, 6.50%, 7.00%, 7.50%, 8.00%, 8.50%, 9.00%, 9.50%, 10.00% NAb, or any range therein.

In some embodiments, all of the autoantibodies to the biologic are neutralizing antibodies and the sample is defined as having 100% neutralizing anti-drug antibodies (NAb) and/or 0% non-neutralizing anti-drug antibodies (non-NAb). In these embodiments, the level of the free labeled biologic binding moiety measured in step (c) is generally the same as the level of the free labeled biologic binding moiety in the control sample, and the autoantibodies are predicted to completely block or interfere with the binding between the biologic and the biologic binding moiety.

In other embodiments, none of the autoantibodies to the biologic are neutralizing antibodies and the sample is defined as having 100% non-NAb and/or 0% NAb. In these embodiments, the level of the free labeled biologic binding moiety measured in step (c) is generally absent (e.g., undetectable) compared to the level of the free labeled biologic binding moiety in the control sample, and the autoantibodies are predicted to not completely block or interfere with the binding between the biologic and the biologic binding moiety.

In further embodiments, when both neutralizing and non-neutralizing forms of the autoantibody are present in a sample, the percent of each species can be expressed on their own (e.g., 50% NAb or 50% non-NAb is defined as an equal proportion of NAb and non-NAb in a sample) or as a ratio. In certain instances, the ratio is calculated by dividing the percent of NAb by the percent of non-NAb, or vice versa. In other instances, the ratio is calculated by dividing the level of NAb by the level of non-NAb, or vice versa.

In some embodiments, the biologic includes antibodies (e.g., anti-TNFα monoclonal antibodies), antibody fragments, proteins (e.g., cytokines such as interleukins), polypeptides, peptides, fusion proteins, multivalent binding proteins, antibody-drug conjugates, vaccines, nucleic acids, sugars, recombinant forms thereof, engineered forms thereof, and combinations thereof.

In other embodiments, the sample is a whole blood, serum, or plasma sample, e.g., from a subject receiving biologic therapy. In preferred embodiments, the sample is serum. In particular embodiments, the subject has a disease or disorder such as, e.g., an autoimmune disease (e.g., rheumatoid arthritis), an inflammatory disease (e.g., inflammatory bowel disease (IBD) such as Crohn's disease (CD) or ulcerative colitis (UC)), or cancer.

In certain embodiments, the sample has or is suspected of having an autoantibody to the biologic. In other embodiments, the biologic autoantibody includes, but is not limited to, human anti-chimeric antibodies (HACA), human anti-humanized antibodies (HAHA), and human anti-mouse antibodies (HAMA), as well as combinations thereof.

In yet another aspect, the present invention provides a method for determining whether a neutralizing form of an autoantibody to a first biologic is cross-reactive with a second (i.e., different) biologic, the method comprising:

(a) detecting or measuring the presence, level, or percent of a neutralizing form of the autoantibody in a sample in accordance with an assay described herein to determine whether the sample is positive or negative for the neutralizing form of the autoantibody; and if the sample is positive for the neutralizing form of the autoantibody, then:

(b) contacting the sample with a labeled second biologic to form a labeled complex of the labeled second biologic and the neutralizing form of the autoantibody (i.e., wherein the components of the labeled complex are not covalently attached to each other);

(c) subjecting the labeled complex to size exclusion chromatography to separate the labeled complex (e.g., from free labeled second biologic); and (d) detecting the labeled complex, thereby determining whether a neutralizing form of an autoantibody to a first biologic is cross-reactive with a second biologic.

In certain embodiments, the presence of the labeled complex is an indication that the neutralizing autoantibody against the first biologic is cross-reactive with the second biologic, i.e., the neutralizing autoantibody will inhibit the activity of both the first and second biological drugs.

In certain other embodiments, the absence of the labeled complex is an indication that the neutralizing autoantibody against the first biologic is not cross-reactive with the second biologic, i.e., the neutralizing autoantibody will not inhibit the activity of the second biological drug.

In some embodiments, the first and second biologics are independently selected from the group consisting of antibodies (e.g., anti-TNFα monoclonal antibodies), antibody fragments, proteins (e.g., cytokines such as interleukins), polypeptides, peptides, fusion proteins, multivalent binding proteins, antibody-drug conjugates, vaccines, nucleic acids, sugars, recombinant forms thereof, engineered forms thereof, and combinations thereof.

In other embodiments, the sample is a whole blood, serum, or plasma sample, e.g., from a subject receiving biologic therapy. In preferred embodiments, the sample is serum. In particular embodiments, the subject has a disease or disorder such as, e.g., an autoimmune disease (e.g., rheumatoid arthritis), an inflammatory disease (e.g., inflammatory bowel disease (IBD) such as Crohn's disease (CD) or ulcerative colitis (UC)), or cancer.

In certain embodiments, the sample has or is suspected of having an autoantibody to the biologic. In other embodiments, the biologic autoantibody includes, but is not limited to, human anti-chimeric antibodies (HACA), human anti-humanized antibodies (HAHA), and human anti-mouse antibodies (HAMA), as well as combinations thereof.

In certain aspects, the assay methods of the present invention further comprise an acid dissociation step comprising contacting a sample with an acid prior to, during, and/or after contacting the sample with a labeled biologic and a labeled biologic binding moiety.

In certain other aspects, the assay methods of the present invention comprise detecting the presence or level of one or more isotypes of a neutralizing and/or non-neutralizing form of an autoantibody to a biologic in a sample.

In one particular aspect, the present invention provides a method for detecting the presence of a neutralizing and/or non-neutralizing form of an autoantibody to an anti-TNFα drug in a sample, the method comprising:

(a) contacting the sample with a labeled anti-TNFα drug and a labeled TNFα to form:

(i) a first labeled complex (i.e., immuno-complex or conjugate) of the labeled anti-TNFα drug and the autoantibody (i.e., wherein the components of the first labeled complex are not covalently attached to each other); and/or (ii) a second labeled complex (i.e., immuno-complex or conjugate) of the labeled anti-TNFα drug, the labeled TNFα, and the autoantibody (i.e., wherein the components of the second labeled complex are not covalently attached to each other);

(b) subjecting the first labeled complex and/or the second labeled complex to size exclusion chromatography to separate them from free (i.e., unbound) labeled TNFα, free labeled anti-TNFα drug, and/or a complex of labeled anti-TNFα drug and labeled TNFα;

(c) measuring the level of free labeled TNFα after size exclusion chromatography (e.g., by measuring the area under the curve (AUC) of the free labeled TNFα peak following size exclusion chromatography (SEC)); and (d) comparing the level of the free labeled TNFα measured in step (c) to the level of free labeled TNFα in a control sample (e.g., by measuring the AUC of the free labeled TNFα peak following SEC of a reference sample containing only free labeled TNFα), thereby detecting the presence of a neutralizing and/or non-neutralizing form of the autoantibody.

In some embodiments, a neutralizing form of the autoantibody interferes with the binding between the anti-TNFα drug and TNFα. In other embodiments, a non-neutralizing form of the autoantibody does not interfere with the binding between the anti-TNFα drug and TNFα.

In some instances, free labeled TNFα consists of labeled TNFα that is substantially free of bound anti-TNFα drug (e.g., labeled and/or unlabeled anti-TNFα drug).

In certain embodiments, a neutralizing form of the autoantibody is detected when the level of the free labeled TNFα measured in step (c) is the same or substantially the same as the level of the free labeled TNFα in the control sample. In certain other embodiments, a non-neutralizing form of the autoantibody is detected when the level of the free labeled TNFα measured in step (c) is decreased (e.g., substantially decreased) or absent (e.g., undetectable) compared to the level of the free labeled TNFα in the control sample.

In particular embodiments, the level of the free labeled TNFα measured in step (c) is considered to be substantially the same as the level of the free labeled TNFα in the control sample when it is at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% the level of the free labeled TNFα measured in the control sample. In particular embodiments, the level of the free labeled TNFα measured in step (c) is considered to be substantially decreased compared to the level of the free labeled TNFα in the control sample when it is at least about 50%, 55%, 60%, 65%, 70%, 75%, 80%, 85%, 90%, or 95% less than the level of the free labeled TNFα measured in the control sample.

In certain embodiments, the level of free labeled TNFα is measured by integrating the area under the curve (AUC) of the free labeled TNFα peak from a plot of signal intensity as a function of elution time from the size exclusion chromatography (e.g., SEC-HPLC).

In some embodiments, the anti-TNFα drug is selected from the group consisting of REMICADE™ (infliximab), ENBREL™ (etanercept), HUMIRA™ (adalimumab), CIMZIA® (certolizumab pegol), SIMPONI® (golimumab; CNTO 148), and combinations thereof.

In other embodiments, the sample is a whole blood, serum, or plasma sample, e.g., from a subject receiving anti-TNFα drug therapy. In preferred embodiments, the sample is serum. In particular embodiments, the subject has a TNFα-mediated disease or disorder such as, e.g., an autoimmune disease (e.g., rheumatoid arthritis) or an inflammatory disease (e.g., inflammatory bowel disease (IBD) such as Crohn's disease (CD) or ulcerative colitis (UC)).

In certain embodiments, the sample has or is suspected of having an autoantibody to the anti-TNFα drug. In other embodiments, the anti-TNFα drug autoantibody includes, but is not limited to, human anti-chimeric antibodies (HACA), human anti-humanized antibodies (HAHA), and human anti-mouse antibodies (HAMA), as well as combinations thereof.

In another particular aspect, the present invention provides a method for measuring the level or percent of a neutralizing form of an autoantibody to an anti-TNFα drug in a sample, the method comprising:
(a) contacting the sample with a labeled anti-TNFα drug and a labeled TNFα to form:
   (i) a first labeled complex (i.e., immuno-complex or conjugate) of the labeled anti-TNFα drug and the autoantibody (i.e., wherein the components of the first labeled complex are not covalently attached to each other); and/or
   (ii) a second labeled complex (i.e., immuno-complex or conjugate) of the labeled anti-TNFα drug, the labeled TNFα, and the autoantibody (i.e., wherein the components of the second labeled complex are not covalently attached to each other);
(b) subjecting the first labeled complex and/or the second labeled complex to size exclusion chromatography to separate them from free (i.e., unbound) labeled TNFα, free labeled anti-TNFα drug, and/or a complex of labeled anti-TNFα drug and labeled TNFα;
(c) measuring the level of free labeled TNFα after size exclusion chromatography (e.g., by measuring the area under the curve (AUC) of the free labeled TNFα peak following size exclusion chromatography (SEC)); and
(d) comparing the level of free labeled TNFα measured in step (c) to a normalized level or percent of free labeled TNFα in a control sample (e.g., by measuring and normalizing the AUC of the free labeled TNFα peak following SEC of a reference sample containing only free labeled TNFα to calculate the level or percent of free labeled TNFα), wherein the normalized level or percent of the free labeled TNFα in the control sample corresponds to the level or percent of a neutralizing form of the autoantibody.

In some embodiments, the difference between the normalized level or percent of the free labeled TNFα in the control sample and the level of free labeled TNFα measured in step (c) corresponds to the level or percent of a non-neutralizing form of the autoantibody.

In some instances, free labeled TNFα consists of labeled TNFα that is substantially free of bound anti-TNFα drug (e.g., labeled and/or unlabeled anti-TNFα drug).

In particular embodiments, the level or percent of the free labeled TNFα in a control sample is normalized by measuring the peak area (e.g., by measuring the AUC) of a complex formed between the labeled anti-TNFα drug and labeled TNFα (e.g., "labeled complex"), and then subtracting the measured peak area of the labeled complex from the peak area of the free labeled TNFα (e.g., by measuring the AUC of the free labeled TNFα peak).

In certain embodiments, the level of free labeled TNFα is measured by integrating the area under the curve (AUC) of the free labeled TNFα peak from a plot of signal intensity as a function of elution time from the size exclusion chromatography (e.g., SEC-HPLC). In other embodiments, the level of a complex formed between the labeled anti-TNFα drug and labeled TNFα is measured by integrating the AUC of the free labeled TNFα peak from a plot of signal intensity as a function of elution time from the size exclusion chromatography (e.g., SEC-HPLC).

In certain embodiments, a subpopulation of the autoantibody to an anti-TNFα drug (e.g., ADA) is a neutralizing form of the autoantibody (e.g., NAb). In some embodiments, the total level of an autoantibody to an anti-TNFα drug in a sample can be calculated by adding the levels of both neutralizing and non-neutralizing forms of the autoantibody measured in accordance with the methods of the invention.

In some embodiments, the level of the free labeled TNFα measured in step (c) is further compared to a negative control, a positive control, or a combination thereof. Non-limiting examples of negative controls include a mouse monoclonal anti-human $IgG_1$ Fc sample and/or a rabbit monoclonal anti-human $IgG_1$ Fc sample. Non-limiting examples of positive controls include a pooled ADA-positive patient serum sample and/or a sample of rabbit polyclonal antibodies against the $F(ab')_2$ fragment of an anti-TNFα drug.

In further embodiments, the percent of the neutralizing form of the autoantibody (e.g., NAb) determined in step (d) is compared to a cutoff value or reference range established from a healthly control (e.g., normal human serum). In particular embodiments, the cutoff value or reference range is expressed as a threshold percent of NAb that the sample must have in order to be considered positive for NAb. In such embodiments, the sample is positive for NAb when the percent of NAb determined in step (d) is greater than or equal to the cutoff value or reference range established from the healthly control. In other embodiments, the sample is negative for NAb when the percent of NAb determined in step (d) is less than the cutoff value or reference range established from the healthly control. Non-limiting examples of cutoff values or reference ranges include, e.g., at least about 0.25%, 0.50%, 0.75%, 1.00%, 1.50%, 2.00%, 2.50%, 2.60%, 2.70%, 2.80%, 2.90%, 3.00%, 3.01%, 3.02%, 3.03%, 3.04%, 3.05%, 3.06%, 3.07%, 3.08%, 3.09%, 3.10%, 3.20%, 3.30%, 3.40%, 3.50%, 4.00%, 4.50%, 5.00%, 5.50%, 6.00%, 6.50%, 7.00%, 7.50%, 8.00%, 8.50%, 9.00%, 9.50%, 10.00% NAb, or any range therein. In some instances, the cutoff value or reference range is about 3.00% NAb or about 3.06% NAb or between about 3.00%-3.10% NAb.

In some embodiments, all the autoantibodies to the anti-TNFα drug are neutralizing antibodies and the sample is defined as having 100% neutralizing anti-drug antibodies (NAb) and/or 0% non-neutralizing anti-drug antibodies (non-NAb). In these embodiments, the level of the free labeled TNFα measured in step (c) is generally the same as the level of the free labeled TNFα in the control sample, and the autoantibodies are predicted to completely block or interfere with the binding between the anti-TNFα drug and TNFα.

In certain other embodiments, none of the autoantibodies to the anti-TNFα drug are neutralizing antibodies and the sample is defined as having 100% non-NAb and/or 0% NAb. In these embodiments, the level of the free labeled TNFα measured in step (c) is generally absent (e.g., undetectable) compared to the level of the free labeled TNFα in the control sample, and the autoantibodies are predicted to not completely block or interfere with the binding between the anti-TNFα drug and TNFα.

In further embodiments, when both neutralizing and non-neutralizing forms of the autoantibody are present in a sample, the percent of each species can be expressed on their own (e.g., 50% NAb or 50% non-NAb is defined as an equal proportion of NAb and non-NAb in a sample) or as a ratio. In certain instances, the ratio is calculated by dividing the percent of NAb by the percent of non-NAb, or vice versa. In other instances, the ratio is calculated by dividing the level of NAb by the level of non-NAb, or vice versa.

In some embodiments, the anti-TNFα drug is selected from the group consisting of REMICADE™ (infliximab), ENBREL™ (etanercept), HUMIRA™ (adalimumab), CIMZIA® (certolizumab pegol), SIMPONI® (golimumab; CNTO 148), and combinations thereof.

In other embodiments, the sample is a whole blood, serum, or plasma sample, e.g., from a subject receiving anti-TNFα drug therapy. In preferred embodiments, the sample is serum. In particular embodiments, the subject has a TNFα-mediated disease or disorder such as, e.g., an autoimmune disease (e.g., rheumatoid arthritis) or an inflammatory disease (e.g., inflammatory bowel disease (IBD) such as Crohn's disease (CD) or ulcerative colitis (UC)).

In certain embodiments, the sample has or is suspected of having an autoantibody to the anti-TNFα drug. In other embodiments, the anti-TNFα drug autoantibody includes, but is not limited to, human anti-chimeric antibodies (HACA), human anti-humanized antibodies (HAHA), and human anti-mouse antibodies (HAMA), as well as combinations thereof.

In yet another particular aspect, the present invention provides a method for determining whether a neutralizing form of an autoantibody to a first anti-TNFα drug is cross-reactive with a second (i.e., different) anti-TNFα drug, the method comprising:
  (a) detecting or measuring the presence, level, or percent of a neutralizing form of the autoantibody in a sample in accordance with an assay described herein to determine whether the sample is positive or negative for the neutralizing form of the autoantibody; and
  if the sample is positive for the neutralizing form of the autoantibody, then:
  (b) contacting the sample with a labeled second anti-TNFα drug to form a labeled complex of the labeled second anti-TNFα drug and the neutralizing form of the autoantibody (i.e., wherein the components of the labeled complex are not covalently attached to each other);
  (c) subjecting the labeled complex to size exclusion chromatography to separate the labeled complex (e.g., from free labeled second anti-TNFα drug); and
  (d) detecting the labeled complex, thereby determining whether a neutralizing form of an autoantibody to a first anti-TNFα drug is cross-reactive with a second anti-TNFα drug.

In certain embodiments, the presence of the labeled complex is an indication that the neutralizing autoantibody against the first anti-TNFα drug is cross-reactive with the second anti-TNFα drug, i.e., the neutralizing autoantibody will inhibit the activity of both the first and second anti-TNFα drugs.

In certain other embodiments, the absence of the labeled complex is an indication that the neutralizing autoantibody against the first anti-TNFα drug is not cross-reactive with the second anti-TNFα drug, i.e., the neutralizing autoantibody will not inhibit the activity of the second anti-TNFα drug.

In particular embodiments, the first and second anti-TNFα drugs are independently selected from the group consisting of REMICADE™ (infliximab), ENBREL™ (etanercept), HUMIRA™ (adalimumab), CIMZIA® (certolizumab pegol), SIMPONI® (golimumab; CNTO 148), and combinations thereof.

In other embodiments, the sample is a whole blood, serum, or plasma sample, e.g., from a subject receiving anti-TNFα drug therapy. In preferred embodiments, the sample is serum. In particular embodiments, the subject has a TNFα-mediated disease or disorder such as, e.g., an autoimmune disease (e.g., rheumatoid arthritis) or an inflammatory disease (e.g., inflammatory bowel disease (IBD) such as Crohn's disease (CD) or ulcerative colitis (UC)).

In certain embodiments, the sample has or is suspected of having an autoantibody to the anti-TNFα drug. In other embodiments, the anti-TNFα drug autoantibody includes, but is not limited to, human anti-chimeric antibodies (HACA), human anti-humanized antibodies (HAHA), and human anti-mouse antibodies (HAMA), as well as combinations thereof.

In certain aspects, the assay methods of the present invention further comprise an acid dissociation step comprising contacting a sample with an acid prior to, during, and/or after contacting the sample with a labeled anti-TNFα drug and a labeled TNFα.

Methods for detecting anti-drug antibodies using acid dissociation are described herein and in PCT Application No. PCT/US2012/025437, filed Feb. 16, 2012, the disclosure of which is hereby incorporated by reference in its entirety for all purposes.

In certain other aspects, the assay methods of the present invention comprise detecting the presence or level of one or more isotypes of a neutralizing and/or non-neutralizing form of an autoantibody to an anti-TNFα drug in a sample. As a non-limiting example, the assays of the present invention can be used to determine different neutralizing and/or non-neutralizing ADA isotypes in samples from ADA-positive patients receiving an anti-TNFα drug such as REMICADE™ (infliximab) or HUMIRA™ (adalimumab). In certain embodiments, the one or more isotypes comprises a plurality of at least two, three, four, five, or more isotypes. In other embodiments, the one or more isotypes is selected from the group consisting of IgA, IgD, IgE, IgG, and IgM isotypes, subclasses thereof, and combinations thereof. In certain embodiments, each autoantibody isotype is characterized, identified, and/or detected by its retention time. In other embodiments, each autoantibody isotype is characterized, identified, and/or detected upon a signal that is generated by the proximity binding of detector moieties such as labeled anti-TNFα drug and labeled labeled anti-Ig antibodies specific for different antibody isotypes. In certain instances, the signal comprises a fluorescent signal that can be detected by fluorescence resonance energy transfer (FRET).

Methods for detecting anti-drug antibody (ADA) isotypes are further described in PCT Publication No. WO 2012/054532, the disclosure of which is hereby incorporated by reference in its entirety for all purposes.

A biologic (e.g., anti-TNFα drug) or biologic binding moiety (e.g., TNFα) can be labeled with any of a variety of detectable group(s). In preferred embodiments, the biologic (e.g., anti-TNFα drug) and the biologic binding moiety (e.g., TNFα) comprise different labels. In certain embodiments, a biologic (e.g., anti-TNFα drug) or biologic binding moiety (e.g., TNFα) is labeled with a fluorophore or a fluorescent dye. Non-limiting examples of fluorophores or fluorescent dyes include those listed in the Molecular Probes Catalogue, which is herein incorporated by reference (see, R. Haugland, *The Handbook-A Guide to Fluorescent*

Probes and Labeling Technologies, 10$^{th}$ Edition, Molecular probes, Inc. (2005)). Such exemplary fluorophores or fluorescent dyes include, but are not limited to, Alexa Fluor® dyes such as Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, and/or Alexa Fluor® 790, as well as other fluorophores including, but not limited to, Dansyl Chloride (DNS-Cl), 5-(iodoacetamida)fluoroscein (5-IAF), fluoroscein 5-isothiocyanate (FITC), tetramethylrhodamine 5-(and 6-)isothiocyanate (TRITC), 6-acryloyl-2-dimethyl-aminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids (e.g., 1-anilinonaphthalene-8-sulfonic acid (ANS), 6-(p-toluidinyl) naphthalen-e-2-sulfonic acid (TNS), and the like), Anthroyl fatty acid, DPH, Parinaric acid, TMA-DPH, Fluorenyl fatty acid, fluorescein-phosphatidyletanolamine, Texas Red-phosphatidylethanolamine, Pyrenyl-phophatidylcholine, Fluorenyl-phosphotidylcholine, Merocyanine 540,1-(3-sulfonatopropyl)-4-[β-2[(di-n-butylamino)-6 naphthyl]vinyl] pyridinium betaine (Naphtyl Styryl), 3,3'dipropylthiadicarbocyanine (di S-C$_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1, 4', 6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, metal-ligand complexes, IRDye® 700DX, IRDye® 700, IRDye® 80016, IRDye® 800CW, IRDye® 800, Cy5, Cy5.5, Cy7, DY 676, DY680, DY682, DY780, and mixtures thereof. Additional suitable fluorophores include enzyme-cofactors; lanthanide, green fluorescent protein, yellow fluorescent protein, red fluorescent protein, or mutants and derivates thereof. In one embodiment of the invention, the second member of the specific binding pair has a detectable group attached thereto.

Typically, the fluorescent group is a fluorophore selected from the category of dyes comprising polymethines, pthalocyanines, cyanines, xanthenes, fluorenes, rhodamines, coumarins, fluoresceins and BODIPY™.

In one embodiment, the fluorescent group is a near-infrared (NIR) fluorophore that emits in the range of between about 650 to about 900 nm. Use of near infrared fluorescence technology is advantageous in biological assays as it substantially eliminates or reduces background from auto fluorescence of biosubstrates. Another benefit to the near-IR fluorescent technology is that the scattered light from the excitation source is greatly reduced since the scattering intensity is proportional to the inverse fourth power of the wavelength. Low background fluorescence and low scattering result in a high signal to noise ratio, which is essential for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components. Within aspects of this embodiment, the fluorescent group is preferably selected form the group consisting of IRDye® 700DX, IRDye® 700, IRDye® 800RS, IRDye® 800CW, IRDye® 800, Alexa Fluor® 660, Alexa Fluor® 680, Alexa Fluor® 700, Alexa Fluor® 750, Alexa Fluor® 790, Cy5, Cy5.5, Cy7, DY 676, DY680, DY682, and DY780. In certain embodiments, the near infrared group is IRDye® 800CW, IRDye® 800, IRDye® 700DX, IRDye® 700, or Dynomic DY676.

Fluorescent labeling is accomplished using a chemically reactive derivative of a fluorophore. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide, many of which are commercially available. Reaction of any of these reactive dyes with a biologic (e.g., anti-TNFα drug) or biologic binding moiety (e.g., TNFα) results in a stable covalent bond formed between a fluorophore and a biologic (e.g., anti-TNFα drug) or biologic binding moiety (e.g., TNFα).

In certain instances, following a fluorescent labeling reaction, it is often necessary to remove any nonreacted fluorophore from the labeled target molecule. This is often accomplished by size exclusion chromatography, taking advantage of the size difference between fluorophore and labeled protein.

Reactive fluorescent dyes are available from many sources. They can be obtained with different reactive groups for attachment to various functional groups within the target molecule. They are also available in labeling kits that contain all the components to carry out a labeling reaction. In one preferred aspect, Alexa Fluor® 647 C2 maleimide is used from Invitrogen (Cat. No. A-20347).

Specific immunological binding of a neutralizing and/or non-neutralizing anti-drug antibody (e.g., NAb and/or non-NAb) to a biologic (e.g., anti-TNFα drug) and/or biologic binding moiety (e.g., TNFα) can be detected directly or indirectly. Direct labels include fluorescent or luminescent tags, metals, dyes, radionuclides, and the like, attached to the antibody. In certain instances, a biologic (e.g., anti-TNFα drug) or biologic binding moiety (e.g., TNFα) labeled with different radionuclides can be used for determining the presence or level of NAb and/or non-NAb in a sample. In other instances, a chemiluminescence assay using chemiluminescent biologic (e.g., anti-TNFα drug) and biologic binding moiety (e.g., TNFα) is suitable for sensitive, non-radioactive detection of the presence or level of NAb and/or non-NAb in a sample. In particular instances, a biologic (e.g., anti-TNFα drug) and biologic binding moiety (e.g., TNFα) labeled with different fluorochromes is suitable for detection of the presence or level of NAb and/or non-NAb in a sample. Examples of fluorochromes include, without limitation, Alexa Fluor® dyes, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of NAb and/or non-NAb levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

In certain embodiments, size exclusion chromatography is used. The underlying principle of SEC is that particles of different sizes will elute (filter) through a stationary phase at different rates. This results in the separation of a solution of particles based on size. Provided that all the particles are loaded simultaneously or near simultaneously, particles of the same size elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

In certain aspects, the eluent is collected in constant volumes, or fractions. The more similar the particles are in size, the more likely they will be in the same fraction and not detected separately. Preferably, the collected fractions are examined by spectroscopic techniques to determine the concentration of the particles eluted. Typically, the spectroscopy detection techniques useful in the present invention include, but are not limited to, fluorometry, refractive index (RI), and ultraviolet (UV). In certain instances, the elution volume decreases roughly linearly with the logarithm of the molecular hydrodynamic volume (i.e., heaver moieties come off first).

In a further aspect, the present invention provides a method for monitoring and/or optimizing therapy to a biologic in a subject receiving a course of therapy with the biologic, the method comprising:

(a) detecting or measuring the presence, level, or percent of a neutralizing form of an autoantibody to the biologic in accordance with the assay described herein at a plurality of time points over the course of therapy;

(b) detecting a change in the presence, level, or percent of the neutralizing form of the autoantibody over time; and (c) determining a subsequent dose of the course of therapy for the subject or whether a different course of therapy should be administered to the subject based upon the change in the presence, level, or percent of the neutralizing form of the autoantibody over time.

In certain embodiments, the plurality of time points comprises at least 2, 3, 4, 5, 6, 7, 8, 9, 10, 11, 12, 13, 14, 15, 16, 17, 18, 19, 20, 25, 30, 35, 40, 45, 50, or more time points.

In one particular aspect, the present invention provides a method for monitoring and/or optimizing therapy to a biologic in a subject receiving a course of therapy with the biologic, the method comprising:

(a) measuring the level or percent of a neutralizing form of an autoantibody to the biologic in a first sample from the subject as described herein at time point $t_0$;

(b) measuring the level or percent of the neutralizing form of the autoantibody in a second sample from the subject as described herein at time point $t_1$;

(c) optionally repeating step (b) with n additional samples from the subject at time points $t_{n+1}$, wherein n is an integer from 1 to about 25 (e.g., n is 1, 2, 3, 4, 5, 6, 7, 8, 9, 10, 11, 12, 13, 14, 15, 16, 17, 18, 19, 20, 21, 22, 23, 24, or 25, or any range therein);

(d) detecting a change in the level or percent of the neutralizing form of the autoantibody from time points $t_0$ to $t_1$ or from time points $t_0$ to $t_{n+1}$; and (e) determining a subsequent dose of the course of therapy for the subject or whether a different course of therapy should be administered to the subject based upon the change in the level or percent of the neutralizing form of the autoantibody over time.

In certain other embodiments, the level or percent of the neutralizing form of the autoantibody (e.g., NAb) is measured during the course of biologic drug therapy at one or more (e.g., a plurality) of the following weeks: 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 80, 90, 100, etc.

In some embodiments, determining a subsequent dose of the course of therapy for the subject comprises maintaining, increasing, or decreasing a subsequent dose of the course of therapy for the subject. In other embodiments, determining a different course of therapy for the subject comprises treatment with a different biologic drug. In other embodiments, determining a different course of therapy for the subject comprises treatment with the current course of therapy along with another therapeutic agent. In further embodiments, determining a different course of therapy for the subject comprises changing the current course of therapy (e.g., switching to a different biologic or to a drug that targets a different mechanism).

In particular embodiments, an increase in the level or percent of the neutralizing form of the autoantibody (e.g., NAb) over time is an indication that treatment adjustment should be recommended for the subject. In certain other embodiments, a change from an absence of the neutralizing form of the autoantibody (e.g., NAb) to the presence thereof over time is an indication that treatment adjustment should be recommended for the subject. In these embodiments, the subject can be treated with the current course of therapy (e.g., taking the existing biologic) along with one or more other therapeutic agents. In certain alternative embodiments, the subject can be switched to a different biologic. In certain other alternative embodiments, the subject can be switched to a drug (e.g., biologic and/or non-biologic) that targets a different mechanism.

In an additional aspect, the present invention provides a method for optimizing therapy and/or reducing toxicity in a subject receiving a course of therapy with a first biologic, the method comprising:
  (a) determining whether a neutralizing form of an autoantibody to the first biologic is cross-reactive with a second (i.e., different) biologic by detecting or measuring the presence, level, or percent of a neutralizing form of the autoantibody in a sample from the subject in accordance with an assay described herein; and
  (b) determining that a different course of therapy should be administered to the subject if the neutralizing form of the autoantibody is cross-reactive with the second biologic.

In certain embodiments, determining that a different course of therapy should be administered comprises switching to a drug (e.g., biologic and/or non-biologic) that targets a different mechanism.

In some embodiments, the method further comprises determining that a subsequent dose of the current course of therapy be increased or decreased, or that a different course of therapy should be administered to the subject if the neutralizing form of the autoantibody is not cross-reactive with the second biologic. In certain instances, the different course of therapy comprises treatment with the second biologic. In certain other instances, the different course of therapy comprises treatment with the first or second biologic along with one or more other therapeutic agents.

In one particular aspect, the present invention provides a method for monitoring and/or optimizing therapy to an anti-TNFα drug in a subject receiving a course of therapy with the anti-TNFα drug, the method comprising:
  (a) detecting or measuring the presence, level, or percent of a neutralizing form of an autoantibody to the anti-TNFα drug in accordance with the assay described herein at a plurality of time points over the course of therapy;
  (b) detecting a change in the presence, level, or percent of the neutralizing form of the autoantibody over time; and
  (c) determining a subsequent dose of the course of therapy for the subject or whether a different course of therapy should be administered to the subject based upon the change in the presence, level, or percent of the neutralizing form of the autoantibody over time.

In certain embodiments, the plurality of time points comprises at least 2, 3, 4, 5, 6, 7, 8, 9, 10, 11, 12, 13, 14, 15, 16, 17, 18, 19, 20, 25, 30, 35, 40, 45, 50, or more time points.

In another particular aspect, the present invention provides a method for monitoring and/or optimizing therapy to an anti-TNFα drug in a subject receiving a course of therapy with the anti-TNFα drug, the method comprising:
  (a) measuring the level or percent of a neutralizing form of an autoantibody to the anti-TNFα drug in a first sample from the subject as described herein at time point $t_0$;
  (b) measuring the level or percent of the neutralizing form of the autoantibody in a second sample from the subject as described herein at time point $t_1$;
  (c) optionally repeating step (b) with n additional samples from the subject at time points $t_{n+1}$, wherein n is an integer from 1 to about 25 (e.g., n is 1, 2, 3, 4, 5, 6, 7, 8, 9, 10, 11, 12, 13, 14, 15, 16, 17, 18, 19, 20, 21, 22, 23, 24, or 25, or any range therein);
  (d) detecting a change in the level or percent of the neutralizing form of the autoantibody from time points $t_0$ to $t_1$ or from time points $t_0$ to $t_{n+1}$; and
  (e) determining a subsequent dose of the course of therapy for the subject or whether a different course of therapy should be administered to the subject based upon the change in the level or percent of the neutralizing form of the autoantibody over time.

In certain other embodiments, the level or percent of the neutralizing form of the autoantibody (e.g., NAb) is measured during the course of anti-TNFα drug therapy at one or more (e.g., a plurality) of the following weeks: 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 80, 90, 100, etc.

In some embodiments, determining a subsequent dose of the course of therapy for the subject comprises maintaining, increasing, or decreasing a subsequent dose of the course of therapy for the subject. In other embodiments, determining a different course of therapy for the subject comprises treatment with a different anti-TNFα drug. In other embodiments, determining a different course of therapy for the subject comprises treatment with the current course of therapy along with another therapeutic agent including, but not limited to, an anti-TNF therapy, an immunosuppressive agent, a corticosteroid, a drug that targets a different mechanism, a nutrition therapy, and other combination treatments. In further embodiments, determining a different course of therapy for the subject comprises changing the current course of therapy (e.g., switching to a different anti-TNF drug or to a drug that targets a different mechanism such as an IL-6 receptor-inhibiting monoclonal antibody, anti-integrin molecule (e.g., Tysabri, Vedaluzamab), JAK-2 inhibitor, and tyrosine kinase inhibitor, or to a nutrition therapy (e.g., special carbohydrate diet)).

In particular embodiments, an increase in the level or percent of the neutralizing form of the autoantibody (e.g., NAb) over time is an indication that treatment adjustment should be recommended for the subject. In certain other embodiments, a change from an absence of the neutralizing form of the autoantibody (e.g., NAb) to the presence thereof over time is an indication that treatment adjustment should be recommended for the subject. In these embodiments, the subject can be treated with the current course of therapy (e.g., taking the existing anti-TNFα drug) along with one or more immunosuppressive agents such as, e.g., methotrexate (MTX) or azathioprine (AZA). In certain alternative embodiments, the subject can be switched to a different anti-TNFα drug. In certain other alternative embodiments, the subject can be switched to a drug that targets a different mechanism (e.g., a non-anti-TNFα drug).

In yet another particular aspect, the present invention provides a method for optimizing therapy and/or reducing toxicity in a subject receiving a course of therapy with a first anti-TNFα drug, the method comprising:

(a) determining whether a neutralizing form of an autoantibody to the first anti-TNFα drug is cross-reactive with a second (i.e., different) anti-TNFα drug by detecting or measuring the presence, level, or percent of a neutralizing form of the autoantibody in a sample from the subject in accordance with an assay described herein; and (b) determining that a different course of therapy should be administered to the subject if the neutralizing form of the autoantibody is cross-reactive with the second anti-TNFα drug.

In certain embodiments, determining that a different course of therapy should be administered comprises switching to a drug that targets a different mechanism (e.g., a non-anti-TNFα drug). Non-limiting examples of such drugs include an IL-6 receptor-inhibiting monoclonal antibody, anti-integrin molecule (e.g., Tysabri, Vedaluzamab), JAK-2 inhibitor, tyrosine kinase inhibitor, a nutritition therapy (e.g., special carbohydrate diet), and mixtures thereof.

In some embodiments, the method further comprises determining that a subsequent dose of the current course of therapy be increased or decreased, or that a different course of therapy should be administered to the subject if the neutralizing form of the autoantibody is not cross-reactive with the second anti-TNFα drug. In certain instances, the different course of therapy comprises treatment with the second anti-TNFα drug. In certain other instances, the different course of therapy comprises treatment with the first or second anti-TNFα drug along with one or more immunosuppressive agents such as MTX or AZA.

Methods for detecting anti-TNFα drugs and anti-drug antibodies are further described in PCT Publication No. WO 2011/056590, the disclosure of which is hereby incorporated by reference in its entirety for all purposes.

In certain instances, the present invention may further comprise administering to a subject a therapeutically effective amount of a course of therapy such as an anti-TNFα drug or a drug that targets a different mechanism (e.g., a non-anti-TNFα drug) useful for treating one or more symptoms associated with a TNFα-mediated disease or disorder (e.g., IBD such as CD or UC). For therapeutic applications, the course of therapy can be administered alone or co-administered in combination with one or more additional agents as described herein. As such, the present invention advantageously enables a clinician to practice "personalized medicine" by guiding treatment decisions and informing therapy selection and optimization for anti-TNFα drugs such that the right drug is given to the right patient at the right time.

IV. Acid Dissociation

In certain aspects, the assay methods of the present invention further comprise an acid dissociation step, e.g., to enable equilibration of immune complexes for measuring the presence or level of neutralizing autoantibodies (NAb), non-neutralizing autoantibodies (non-NAb), and/or isotypes thereof that are generated against biologics such as anti-TNFα drugs. As a result, the presence or level of NAb and/or non-NAb to a biologic (e.g., anti-TNFα drug) administered to a subject in need thereof can be measured without substantial interference from the administered biologic that is also present in the subject's sample. In particular, a subject's sample can be incubated with an amount of acid that is sufficient to provide for the measurement of the presence or level of NAb and/or non-NAb in the presence of the biologic (e.g., anti-TNFα drug) but without substantial interference from high biologic drug levels.

In some embodiments, step (a) of the assay methods of the present invention may comprise:

(a') contacting the sample with an acid to dissociate preformed complexes of the autoantibody (e.g., including neutralizing and/or non-neutralizing forms thereof) and the biologic (e.g., anti-TNFα drug);

(b') contacting the sample with a labeled biologic (e.g., anti-TNFα drug) and a labeled biologic binding moiety (e.g., TNFα) following dissociation of the preformed complexes; and (c') neutralizing the acid in the sample to form:
(i) a first labeled complex of the labeled biologic (e.g., anti-TNFα drug) and the autoantibody; and/or
(ii) a second labeled complex of the labeled biologic (e.g., anti-TNFα drug), the labeled biologic binding moiety (e.g., TNFα), and the autoantibody.

In some alternative embodiments, steps (a') and (b') are performed simultaneously, e.g., the sample is contacted with an acid, a labeled biologic (e.g., anti-TNFα drug), and a labeled biologic binding moiety (e.g., TNFα) at the same time. In other alternative embodiments, step (b') is performed prior to step (a'), e.g., the sample is first contacted with a labeled biologic (e.g., anti-TNFα drug) and a labeled biologic binding moiety (e.g., TNFα), and then contacted with an acid. In further embodiments, steps (b') and (c') are performed simultaneously, e.g., the sample is contacted with a labeled biologic (e.g., anti-TNFα drug) and a labeled biologic binding moiety (e.g., TNFα) and neutralized (e.g., by contacting the sample with one or more neutralizing agents) at the same time.

In particular embodiments, the sample is contacted with an amount of an acid that is sufficient to dissociate preformed complexes of the autoantibody and the biologic (e.g., anti-TNFα drug), such that the labeled biologic binding moiety (e.g., TNFα), the labeled biologic (e.g., anti-TNFα drug), the unlabeled biologic (e.g., anti-TNFα drug), and the autoantibody to the biologic (e.g., anti-TNFα drug) can equilibrate and form complexes therebetween. In certain embodiments, the sample can be contacted with an amount of an acid that is sufficient to allow for the detection and/or measurement of the autoantibody in the presence of a high level of the biologic (e.g., anti-TNFα drug).

In some embodiments, the phrase "high level of a biologic" such as a high level of an anti-TNFα drug includes drug levels of from about 10 to about 100 μg/mL, about 20 to about 80 μg/mL, about 30 to about 70 μg/mL, or about 40 to about 80 μg/mL. In other embodiments, the phrase "high level of a biologic" such as a high level of an anti-TNFα drug includes drug levels greater than or equal to about 10, 20, 30, 40, 50, 60, 70, 80, 90, or 100 μg/mL.

In some embodiments, the acid comprises an organic acid. In other embodiments, the acid comprises an inorganic acid. In further embodiments, the acid comprises a mixture of an organic acid and an inorganic acid. Non-limiting examples of organic acids include citric acid, isocitric acid, glutamic acid, acetic acid, lactic acid, formic acid, oxalic acid, uric acid, trifluoroacetic acid, benzene sulfonic acid, aminomethanesulfonic acid, camphor-10-sulfonic acid, chloroacetic acid, bromoacetic acid, iodoacetic acid, propanoic acid, butanoic acid, glyceric acid, succinic acid, malic acid, aspartic acid, and combinations thereof. Non-limiting examples of inorganic acids include hydrochloric acid, nitric acid, phosphoric acid, sulfuric acid, boric acid, hydrofluoric acid, hydrobromic acid, and combinations thereof.

In certain embodiments, the amount of an acid corresponds to a concentration of from about 0.01M to about 10M, about 0.1M to about 5M, about 0.1M to about 2M, about 0.2M to about 1M, or about 0.25M to about 0.75M of an acid or a mixture of acids. In other embodiments, the amount of an acid corresponds to a concentration of greater than or equal to about 0.01M, 0.05M, 0.1M, 0.2M, 0.3M, 0.4M, 0.5M, 0.6M, 0.7M, 0.8M, 0.9M, 1M, 2M, 3M, 4M, 5M, 6M, 7M, 8M, 9M, or 10M of an acid or a mixture of acids. The pH of the acid can be, for example, about 0.1, 0.5, 1.0, 1.5, 2.0, 2.5, 3.0, 3.5, 4.0, 4.5, 5.0, 5.5, 6.0, or 6.5.

In some embodiments, the sample is contacted with an acid an amount of time that is sufficient to dissociate preformed complexes of the autoantibody and the biologic (e.g., anti-TNFα drug). In certain instances, the sample is contacted (e.g., incubated) with an acid for a period of time ranging from about 0.1 hours to about 24 hours, about 0.2 hours to about 16 hours, about 0.5 hours to about 10 hours, about 0.5 hours to about 5 hours, or about 0.5 hours to about 2 hours. In other instances, the sample is contacted (e.g., incubated) with an acid for a period of time that is greater than or equal to about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, or 10 hours. The sample can be contacted with an acid at 4° C., room temperature (RT), or 37° C.

In certain embodiments, the step of neutralizing the acid comprises raising the pH of the sample to allow the formation of first and/or second labeled complexes described herein. In some embodiments, the acid is neutralized by the addition of one or more neutralizing agents such as, for example, strong bases, weak bases, buffer solutions, and combinations thereof. One skilled in the art will appreciate that neutralization reactions do not necessarily imply a resultant pH of 7. In some instances, acid neutralization results in a sample that is basic. In other instances, acid neutralization results in a sample that is acidic (but higher than the pH of the sample prior to adding the neutralizing agent). In particular embodiments, the neutralizing agent comprises a buffer such as phosphate buffered saline (e.g., 10× PBS) at a pH of about 7.3.

In some embodiments, step (b') further comprises contacting an internal control with the sample together with a labeled biologic (e.g., anti-TNFα drug) and a labeled biologic binding moiety (e.g., TNFα) (e.g., before, during, or after dissociation of the preformed complexes). In certain instances, the internal control comprises a labeled internal control such as, e.g., Biocytin-Alexa 488. In certain other instances, the amount of the labeled internal control ranges from about 1 ng to about 25 ng, about 5 ng to about 25 ng, about 5 ng to about 20 ng, about 1 ng to about 20 ng, about 1 ng to about 10 ng, or about 1 ng to about 5 ng per 100 μL of sample analyzed. In further instances, the amount of the labeled internal control is greater than or equal to about 1 ng, 5 ng, 10 ng, 15 ng, 20 ng, or 25 ng per 100 μL of sample analyzed.

As one non-limiting example of the methods of the present invention, samples such as serum samples (e.g., serum from subjects receiving therapy with an anti-TNFα drug such as Remicade (IFX)) can be incubated with 0.5M citric acid, pH 3.0 for one hour at room temperature. Following the dissociation of preformed complexes between (unlabeled) anti-TNFα drug and autoantibodies to the anti-TNFα drug (e.g., anti-drug antibodies such as anti-IFX antibodies (ATI)), labeled anti-TNFα drug (e.g., IFX-Alexa 488), labeled TNFα (e.g., TNFα-Alexa 532), and optionally an internal control can be added and the reaction mixture (e.g., immediately) neutralized with a neutralizing agent such as 10× PBS, pH 7.3. After neutralization, the reaction mixture can be incubated for another hour at room temperature (e.g., on a plate shaker) to allow equilibration and to complete the reformation of immune complexes between the labeled TNFα, the labeled anti-TNFα drug, the unlabeled anti-TNFα drug, and/or the autoantibody to the anti-TNFα drug. The samples can then be filtered and analyzed by SEC-HPLC as described herein.

In particular embodiments, the methods of the present invention (e.g., comprising acid dissociation followed by homogeneous solution phase binding kinetics) significantly increases the IFX drug tolerance such that NAb and/or non-NAb ATI can be measured in the presence of IFX up to about 60 μg/mL. In other words, the methods of the present invention can detect the presence or level of NAb and/or non-NAb to anti-TNFα drugs such as ATI as well as autoantibodies to other anti-TNFα drugs in the presence of high levels of anti-TNFα drugs (e.g., IFX), but without substantial interference therefrom.

Methods for detecting anti-drug antibodies using acid dissociation are further described in PCT Application No. PCT/US2012/025437, filed Feb. 16, 2012, the disclosure of which is hereby incorporated by reference in its entirety for all purposes.

V. Biologic Therapy

The assays of the present invention are suitable for detecting and/or measuring the presence or absence (e.g., whether positive or negative), level, or percent of neutralizing and/or non-neutralizing autoantibodies to any biologic in a sample from a subject (e.g., a subject receiving biologic therapy). Non-limiting examples of biologics include antibodies, antibody fragments, proteins, polypeptides, peptides, fusion proteins (e.g., Ig fusion proteins or Fc fusion proteins), multivalent binding proteins (e.g., DVD Ig), antibody-drug conjugates, vaccines, nucleic acids, sugars, recombinant forms thereof, engineered forms thereof, and combinations thereof.

Examples of antibody-based biologics include, but are not limited to, therapeutic monoclonal antibodies and antigen-binding fragments thereof. In particular embodiments, the antibody comprises an anti-TNFα drug such as REMICADE™ (infliximab), HUMIRA™ (adalimumab), CIMZIA® (certolizumab pegol), SIMPONI® (golimumab; CNTO 148), or combinations thereof. Additional examples of antibody-based biologics include antibody-drug conjugates such as Adcetris™ (brentuximab vedotin). Table 1 provides an exemplary list of therapeutic monoclonal antibodies which have either been approved or are currently in development. An extensive list of monoclonal antibody therapeutics in clinical development and approved products is provided in the 2006 PhRMA Report entitled "418 Biotechnology Medicines in Testing Promise to Bolster the Arsenal Against Disease," the disclosure of which is hereby incorporated by reference in its entirety for all purposes.

TABLE 1

Therapeutic monoclonal antibodies

| Product Name | Company | Indication(s) |
|---|---|---|
| *Inflammatory Diseases* | | |
| Remicade ™ (infliximab) | Janssen Biotech, Inc. | Crohn's disease |
| ABT 874 | Abbott Laboratories | Crohn's disease |
| Stelara ® (ustekinumab) | Janssen Biotech, Inc. | Crohn's disease |
| Humira ™ (adalimumab) | Abbott Laboratories | Crohn's disease |
| MDX-1100 | Millennium Pharmaceuticals | ulcerative colitis |
| Nuvion ® (visilizumab) | PDL BioPharma | I.V. steroid-refractory ulcerative colitis and Crohn's disease |
| Tysarbi ® (natalizumab) | Biogen Idec | Crohn's disease |
| Simponi ® (golimumab) | Janssen Biotech, Inc. | uveitis |
| *Autoimmune disorders* | | |
| Humira ™ (adalimumab) | Abbott Laboratories | rheumatoid arthritis, ankylosing spondylitis, juvenile rheumatoid arthritis, psoriasis |
| Remicade ™ (infliximab) | Janssen Biotech, Inc. | rheumatoid arthritis |
| Simponi ® (golimumab) | Janssen Biotech, Inc. | rheumatoid arthritis, ankylosing spondylitis, psoriatic arthritis |
| Rituxan ® (rituximab) | Genentech Biogen Idec | rheumatoid arthritis, lupus, primary progressive multiple sclerosis, SLE, relapsing-remitting multiple sclerosis |
| Tysarbi ® (natalizumab) | Biogen Idec | multiple scleorisis |
| Stelara ® (ustekinumab) | Janssen Biotech, Inc. | plaque psoriasis, multiple sclerosis |
| ART 874 | Abbott Laboratories | multiple sclerosis |
| Actemra | Roche | rheumatoid arthritis |
| AME 527 | Applied Molecular | rheumatoid arthritis |
| AMG 108 | Amgen | rheumatoid arthritis |
| AMG 714 | Amgen | rheumatoid arthritis |
| anti-CD16 MAb | MacroGenics | immune thrombocytopenic |
| daclizumab (anti-CD25 MAb) | PDL BioPharma Biogen Idec | multiple sclerosis |
| denosumab (AMG 162) | Amgen | rheumatoid arthritis |
| ETI-201 | Elusys Therapeutics | SLE |
| HuMax-CD20 (ofatumumab) | Genmab | rheumatoid arthritis |
| HuZAF ™ (fontolizumab) | PDL BioPharma Biogen Idec | rheumatoid arthritis |
| IMMU-106 (hCD20) | Immunomedics | autoimmune disease |
| LymphoStat-B ™ (belimumab) | Human Genome Sciences | rheumatoid arthritis, SLE |
| MEDI-545 (MDX-1103) | Medarex MedImmune | lupus |
| siplizumab (MEDI-507) | MedImmune | psoriasis |
| MLN 1202 | Millennium Pharmaceuticals | multiple sclerosis |
| ocrelizumab (anti-CD20) (R1594) | Genentech Biogen Idec Roche | multiple sclerosis, rheumatoid arthritis |
| OKT3-gamma-1 | Johnson & Johnson | psoriatic arthritis |
| TRX 1 (anti-CD4) | TolerRx | cutaneous lupus erythematosus |
| TRX 4 | TolerRx | psoriasis |
| *Infectious diseases* | | |
| Synagis ® (palivizumab) | MedImmune | prevention of respiratory syncytial virus (RSV) |
| MDX-066 (CDA-1) | Medarex | *C. difficile* disease |
| anti-HIV-1 MAb | Polymun Scientific | HIV infection |
| CCR5 MAb | Hunan Genome Sciences | HIV infection |
| Cytolin ® (anti-CD8 MAb) | CytoDyn | HIV infection |
| NM01 | SRD Pharmaceuticals | HIV infection |
| PRO 140 | Progenics Pharmaceuticals | HIV infection |
| TNX-355 | Tanox | HIV infection |
| ABthrax ™ (raxibacumab) | Human Genome Sciences | anthrax |
| Anthim ™ (ETI-204) | Elusys Therapeutics | anthrax |
| anti-hsp90 MAb | NeuTec Pharma | candidiasis |
| anti-staph MAb | MedImmune | prevention of staphylococcal infections |
| Aurexis (tefibazumab) | Inhibitex | prevention and treatment of *S. aureus* bacteremia |
| bavituximab | Peregrine Pharmaceuticals | hepatitis C |
| MDX-1303 | Medarex PharmAthene | anthrax |
| Numax ™ (motavizumab) | MedImmune | RSV |
| Tarvacin ™ | Peregrine Pharmaceuticals | hepatitis C |
| XTL 6865 | XTL Biopharmaceuticals | hepatitis C |
| *Cancer* | | |

TABLE 1-continued

Therapeutic monoclonal antibodies

| Product Name | Company | Indication(s) |
| --- | --- | --- |
| Avastin ™ (bevacizumab) | Genentech | metastatic colorectal cancer |
| Bexxar ® (tositumomab) | GlaxoSmithKline | non-Hodgkin's lymphoma |
| Campath ® (alemtuzumab) | Berlex Laboratories Genzyme | B-cell chronic lymphocytic leukemia |
| Erbitux ™ (cetuximab) | Bristol-Myers Squibb Medarex | colorectal cancer, squamous cell cancer of the head and neck |
| Herceptin ® (trastuzumab) | Genentech | HER2-overexpressing early stage or metastatic breast cancer |
| Mylotarg ™ (gemtuzumab ozogamicin) | Wyeth | acute myeloid leukemia |
| Rituxan ® (rituximab) | Genentech Biogen Idec | B-cell non-Hodgkin's lymphoma, indolent non-Hodgkin's lymphoma induction therapy, relapsed or refractory CLL |
| Zevalin ™ (ibritumomab tiuxetan) | Biogen Idec | Non-Hodgkin's lymphoma |
| 131I-huA33 | Life Science Pharmaceuticals | colorectal cancer |
| 1D09C3 | GPC Biotech | relapsed/refractory B-cell lymphomas |
| AGS PSCA MAb | Agensys Merck | prostate cancer |
| AMG 102 | Amgen | cancer |
| AMG 479 | Amgen | cancer |
| AMG 623 | Amgen | B-cell chronic lymphocytic leukemia (CLL) |
| AMG 655 | Amgen | cancer |
| AMG 706 | Amgen | imatinib-resistant GIST, advanced thyroid cancer |
| AMG 706 | Amgen | imatinib resistant GIST, advanced thyroid cancer |
| anti-CD23 MAb | Biogen Idec | CLL |
| anti-CD80 MAb | Biogen Idec | non-Hodgkin's B-cell lymphoma |
| anti-idiotype cancer vaccine | Viventia Biotech | malignant melanoma |
| anti-lymphotoxin beta receptor MAb | Biogen Idec | solid tumors |
| anti-PEM MAb | Somanta Pharmaceuticals | cancer |
| anti-Tac(Fv)-E38 immunotoxin | National Cancer Institute | leukemia, lymphoma |
| Avastin ® (bevacizumab) | Genentech | relapsed metastatic colorectal cancer, first line metastatic breast cancer, first-line non-squamous NSCLC cancers |
| AVE 9633 maytansin-loaded anti-CD33 MAb | Sanofi Aventis | AML |
| bavituximab | Peregrine Pharmaceuticals | solid cancers |
| CAT 3888 | Cambridge Antibody Technology | hairy cell leukemia |
| chimeric MAb | National Cancer Institute | neuroblastoma |
| siltuximab (CNTO 328) | Janssen Biotech, Inc. | renal cancer, prostate cancer, multiple myeloma |
| Cotara ™ | Peregrine Pharmaceuticals | brain cancer |
| bivatuzumab | Boehringer Ingelheim Pharmaceuticals | cancer |
| CP-751871 (figitumumab) | Pfizer | adrenocortical carcinoma, non-small cell lung cancer |
| CS-1008 (tigatuzumab) | Daiichi Sankyo | pancreatic cancer, colorectal cancer, non-small cell lung cancer, ovarian cancer |
| BrevaRex ™ | ViRexx | breast cancer, multiple myeloma |
| denosumab | Amgen | bone loss induced by hormone ablation therapy for breast or prostate cancer, prolonging bone metastases-free survival, bone metastases in breast cancer |
| ecromeximab | Kyowa Hakko USA | malignant melanoma |
| EMD 273063 | EMD Lexigen | solid tumors, malignant melanoma, neuroblastoma, SCLC |
| Erbitux ™ | Bristol Myers Squibb | head/neck cancer, first-line palicreatic, first-line NSCLC, second-line NSCLC, first line colorectal cancer, second-line colorectal cancer |
| GMK | Progenies Pharmaceuticals | prevention of recurrence following surgery to remove primacy melanoma in high-risk patients |
| Campath ® (alemtuzumab) | National Cancer Institute Berlex Laboratories | leukemia, lymphoma |
| HGS-ETR1 | Human Genome Sciences | hematologic and solid tumors |
| HGS ETR2 (mapatumumab) | Human Genome Sciences | hematologic and solid tumors |

TABLE 1-continued

Therapeutic monoclonal antibodies

| Product Name | Company | Indication(s) |
|---|---|---|
| HGS-TR2J | Human Genome Sciences | advanced solid tumors |
| HuC242-DM4 | ImmunoGen | colorectal, gastrointestinal, NSCLC, pancreatic cancers |
| HuMax-CD4 (zanolimumab) | Genmab Serono | cutaneous T-cell lymphoma, non-cutaneous T-cell lymphoma |
| HuMax CD20 (ofatumumab) | Genmab | CLL, non-Hodgkin's lymphoma |
| HuMax-EGFr | Genmab | head and neck cancer |
| huN901-DM1 | ImmunoGen | SCLC multiple myeloma |
| ipilimumab | Bristol-Myers Squibb Medarex | melanoma monotherapy, leukemia, lymphoma, ovarian, prostate, renal cell cancers, melanoma (MCX-010 +/− DTIC), second-line metastatic melanoma (MDX-010 disomotide/overmotide MDX-1379) |
| M195-bismuth 213 conjugate | Actinium Pharmaceuticals | AML |
| M200 (volociximab) | PDL BioPharma Fremont, CA Biogen Idec Cambridge, MA | advanced solid tumors |
| MAb HeFi-1 | National Cancer Institute Bethesda, MD | lymphoma, non-Hodgkin's lymphoma |
| MDX-060 (iratumumab) | Medarex | Hodgkin's disease, anaplastic large-cell-lymphoma |
| MDX-070 | Medarex | prostate cancer |
| MDX-214 | Medarex | ECFR-expressing cancers |
| MEDI-522 | MedImmune | T-cell lymphoma, melanoma, prostate cancer, solid tumors |
| MORAb 003 | Morphotek | ovarian cancer |
| MORAb 009 | Morphotek | mesothelin-expressing tumors |
| neuradiab | Bradmer Pharmaceuticals | glioblastoma |
| nimotuzumab | YM Biosciences | squamous cell carcinomas of the head and neck, recurrent or refractory high grade malignant glioma, anaplastic astrocytomas, glioblastomas and diffuse intrinsic pontine glioma |
| Omnitarg ™ (pertuzumab) | Genentech | ovarian cancer |
| OvaRex ® (oregovomab) | ViRexx MAb | ovarian cancer |
| PAM 4 | Merck | pancreatic cancer |
| panitumumab (rIIluMAb EGFr) | Abgenix | colorectal cancer |
| PSMA-ADC | Progenics Pharmaceuticals | prostate cancer |
| R1550 RadioTheraCIM | Roche YM BioSciences | metastatic breast cancer, glioma |
| RAV 12 | Raven Biotechnologies | cancer |
| Rencarex ® G250 | Wilex AG | renal cancer |
| SGN30 | Seattle Genetics | cutaneous anaplastic large-cell MAb lyrphoma, systemic anaplastic large-cell lymphoma, Hodgkin's disease |
| SGN-33 (lintuzumab) | Seattle Genetics | AML, myelodysplastic syndromes CLL multiple myeloma, non Hodgkin's lymphoma |
| SGN-40 | Seattle Genetics | AML, myelodysplastic syndromes CLL multiple myeloma, non Hodgkin's lymphoma |
| sibroturtumab | Life Science Pharmaceuticals | colorectal, head and neck, lung cancers |
| Tarvacin ™ (bavituximab) | Peregrine Pharmaceuticals | solid tumors |
| tremelimumab | Pfizer | metastatic melanoma, prostate cancer |
| TNX-650 | Tanox | refractory Hodgkin's lymphoma |
| Zevalin ™ (ibritumomab tiuxetan) | Spectrum Pharmaceuticals | non-Hodgkin's lymphoma |

Blood disorders

| | | |
|---|---|---|
| ReoPro ® (abciximab) | Eli Lilly | adjunct to percutaneous coronary intervention for the prevention of cardiac ischemic complications |
| urtoxazumab | Teijin Pharma | hemolytic uremic |
| afelimomab | Abbot Laboratories | sepsis, septic shock |
| eculizumab | Alexion Pharmaceuticals | paroxysmal nocturnal hemoglobinurea |

Cardiovascular disease

| | | |
|---|---|---|
| MLN 1202 | Millennium Pharmaceuticals | atherosclerosis |
| pexelizumab | Alexion Pharmaceuticals Procter & Gamble Pharmaceuticals | acute myocardial infarction, cardiopulmonary bypass |

Diabetes and Related Conditions

TABLE 1-continued

Therapeutic monoclonal antibodies

| Product Name | Company | Indication(s) |
|---|---|---|
| anti-CD3 MAb | MacroGenics | type-1 diabetes mellitus |
| OKT3-gamma-1 | Johnson & Johnson | type-1 diabetes mellitus |
| TRX 4 (anti-CD3) | TolerRx | type-1 diabetes mellitus |
| Genetic Disorders | | |
| Soliris ™ (eculizumab) | Alexion Pharmaceuticals | paroxysmal nocturnal hemoglobinuria (PNH) |
| Neurological Disorders | | |
| RN624 | Rinat Neuroscience | osteoarthritis pain |
| RN1219 | Rinat Neuroscience | Alzheimer's disease |
| Respiratory Disorders | | |
| ABN 912 | Novartis Pharmaceuticals | asthma, chronic obstructive pulmonary disorders (COPD) |
| ABX-IL8 | Amgen | COPD |
| AMG 317 | Amgen | asthma |
| daclizumab (anti-CD25 MAb) | Protein Design Labs Roche | asthma |
| MEDI-528 (anti-TL-9 MAb) | MedImmune | asthma |
| mepolizumab (anti-TL5 MAb) | GlaxoSmithKline | asthma and nasal polyposis |
| TNX-832 | Tanox Houston, TX | respiratory diseases |
| Xolair ® (omalizumab) | Genentech Novartis Pharmaceuticals | pediatric asthma |
| Transplatation | | |
| ORTHOCLONE OKT ® 3 (muromomab-CD3) | Ortho Biotech | acute kidney transplant rejection, reversal of heart and liver transplant rejection |
| Simulect ® (basiliximab) | Novartis Pharmaceuticals | prevention of renal transplant rejection |
| Zenapax ® (daclizumab) | Roche | prophylaxis of acute kidney transplant rejection |
| OKT3-gamma-1 | Protein Design Labs Johnson & Johnson | renal transplant rejection |
| Other | | |
| CR 0002 | CuraGen | kidney inflammation |
| denosumab (AMG 162) | Amgen | postmenopausal osteoporosis |
| mepolizumab (anti-IL5 MAb) | GlaxoSmithKline | hypereosinophilic syndrome, eosinophlic esophagitis |
| Xolair ® (omalizumab) | Genentech Tanox | peanut allergy |

Non-limiting examples of protein-based or polypeptide-based biologics include cytokines (e.g., interleukins), chemokines, growth factors, blood-production stimulating proteins (e.g., erythropoietin), hormones (e.g., Elonva® (follicle stimulating hormone), growth hormone), enzymes (e.g., Pulmozyme® (dornase alfa)), clotting factors, insulin, albumin, fragments thereof, conservatively modified variants thereof, analogs thereof, and combinations thereof.

Examples of cytokines include, but are not limited to, TNFα, TNF-related weak inducer of apoptosis (TWEAK), osteoprotegerin (OPG), IFN-α, IFN-β, IFN-γ, interleukins (e.g., IL-1α, IL-1β, IL-1 receptor antagonist (IL-Ira), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27), adipocytokines (e.g., leptin, adiponectin, resistin, active or total plasminogen activator inhibitor-1 (PAI-1), visfatin, and retinol binding protein 4 (RBP4)), and combinations thereof. In particular embodiments, the interleukin comprises IL-2 such as Proleukin® (aldesleukin; recombinant IL-2).

Examples of chemokines include, but are not limited to, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, $CX_3CL1$, and combinations thereof.

Non-limiting examples of growth factors include epidermal growth factor (EGF), heparin-binding epidermal growth factor (HB-EGF), vascular endothelial growth factor (VEGF), pigment epithelium-derived factor (PEDF; also known as SERPINF1), amphiregulin (AREG; also known as schwannoma-derived growth factor (SDGF)), basic fibroblast growth factor (bFGF), hepatocyte growth factor (HGF), transforming growth factor-α (TGF-α), transforming growth factor-β (TGF-β1, TGF-β2, TGF-β3, etc.), endothelin-1 (ET-1), keratinocyte growth factor (KGF; also known as FGF7), bone morphogenetic proteins (e.g., BMP1-BMP15), platelet-derived growth factor (PDGF), nerve growth factor (NGF), β-nerve growth factor (β-NGF), neurotrophic factors (e.g., brain-derived neurotrophic factor (BDNF), neurotrophin 3 (NT3), neurotrophin 4 (NT4), etc.), growth differentiation factor-9 (GDF-9), granulocyte-colony stimulating factor (G-CSF), granulocyte-macrophage colony stimulating factor (GM-CSF), myostatin (GDF-8), erythropoietin (EPO), thrombopoietin (TPO), and combinations thereof.

Examples of receptor construct-based or fusion protein-based biologics include, but are not limited to, naturally-occurring receptors linked to an immunoglobulin frame (e.g., Orencia® (abatacept; immunoglobin CTLA-4 fusion protein), Amevive® (alefacept; IgG1 fusion protein), ENBREL™ (etanercept; recombinant human TNF-receptor fusion protein), engineered proteins combining two different polypeptide species (e.g., Ontak® (denileukin diftitox; engineered protein comprising interleukin-2 and diphtheria toxin), and combinations thereof.

The present invention can therefore be used in methods for detecting and measuring the presence or level of neutralizing and non-neutralizing autoantibodies to biologics such as anti-TNFα drug therapeutics in a sample from a subject receiving biologic therapy for one or more of the diseases or disorders referred to herein and Table 1, including one or more of the following:

Inflammatory diseases, such as inflammatory bowel disease (IBD) (e.g., Crohn's disease (CD) and ulcerative colitis (UC)), uveitis, sarcoidosis, Wegener's granulomatosis, and other diseases with inflammation as a central feature;

Autoimmune diseases, such as rheumatoid arthritis (RA), multiple scleorisis (MS), systemic lupus erythematosus (SLE), ankylosing spondylitis (Bechterew's disease), lupus, psoriatic arthritis, juvenile idiopathic arthritis, psoriasis, and erythematosus;

Cancer, such as digestive and gastrointestinal cancers (e.g., colorectal cancer, small intestine (small bowel) cancer; gastrointestinal stromal tumors, gastrointestinal carcinoid tumors, colon cancer, rectal cancer, anal cancer, bile duct cancer, gastric (stomach) cancer; esophageal cancer; appendix cancer; and the like); gallbladder cancer; liver cancer; pancreatic cancer; breast cancer; lung cancer (e.g., non-small cell lung cancer); prostate cancer; ovarian cancer; renal cancer (e.g., renal cell carcinoma); cancer of the central nervous system; skin cancer; choriocarcinomas; head and neck cancers; hematological malignancies (e.g., leukemia, lymphoma such as B-cell non-Hodgkin's lymphoma); osteogenic sarcomas (e.g., Ewing sarcoma); soft tissue sarcomas (e.g., Dermatofibrosarcoma Protuberans (DFSP), rhabdomyosarcoma); other soft tissue malignancies, and papillary thyroid carcinomas;

Infectious diseases, such as C. difficile disease, respiratory syncytial virus (RSV), HIV, anthrax, candidiasis, staphylococcal infections, and hepatitis C;

Blood disorders, such as sepsis, septic shock, paroxysmal nocturnal hemoglobinuria, and hemolytic uremic syndrome;

Cardiovascular disease, such as atherosclerosis, acute myocardial infarction, cardiopulmonary bypass, and angina;

Metabolic disorders, such as diabetes, e.g., type-I diabetes mellitus;

Genetic disorders, such as paroxysmal nocturnal hemoglobinuria (PNH);

Neurological disorders, such as osteoarthritis pain and Alzheimer's disease;

Respiratory disorders, such as asthma, chronic obstructive pulmonary disorders (COPD), nasal polyposis, and pediatric asthma;

Skin diseases, such as psoriasis, including chronic moderate to severe plaque psoriasis;

Transplant rejection, such as acute kidney transplant rejection, reversal of heart and liver transplant rejection, prevention of renal transplant rejection, prophylaxis of acute kidney transplant rejection, and renal transplant rejection; and/or Other disorders, such as kidney inflammation, postmenopausal osteoporosis (bone disorders), hypereosinophilic syndrome, eosinophilic esophagitis and peanut allergy.

In particular embodiments, the subject has a TNFα-mediated disease or disorder such as, e.g., an autoimmune disease (e.g., rheumatoid arthritis) or an inflammatory disease (e.g., inflammatory bowel disease (IBD) such as Crohn's disease (CD) or ulcerative colitis (UC)).

VI. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

The examples from PCT Application No. PCT/US2012/025437, filed Feb. 16, 2012, are hereby incorporated by reference in their entirety for all purposes.

Example 1. Development of a Novel Assay to Monitor Neutralizing Anti-Drug Antibody Formation in IBD Patients.

This example illustrates a novel homogeneous assay for detecting or measuring the presence or level of neutralizing and/or non-neutralizing anti-drug autoantibodies (ADA) in a patient sample (e.g., serum) using size exclusion chromatography in the presence of labeled (e.g., fluorescently labeled) anti-TNFα drug and labeled TNFα. In particular embodiments, this assay is advantageous because it obviates the need for wash steps which remove low affinity ADA, uses distinct labels (e.g., fluorophores) that allow for detection on the visible and/or IR spectra which decreases background and serum interference issues, increases the ability to detect neutralizing and/or non-neutralizing ADA in patients with a low titer due to the high sensitivity of fluorescent label detection, and occurs as a liquid phase reaction, thereby reducing the chance of any changes in the epitope by attachment to a solid surface such as an ELISA plate.

Infliximab (IFX) and adalimumab (ADL) are anti-TNF monoclonal antibodies prescribed for the treatment of inflammatory bowel disease (IBD). Anti-drug antibodies (ADA) often develop during the course of therapy. A proportion of these ADA are neutralizing antibodies (NAb). While ADA will negatively impact drug pharmacokinetics, the presence of NAb will additionally cause loss of drug efficacy through blockage of the drug's binding site. This example describes an assay to monitor the development of NAb in IBD patients receiving IFX treatment based on a homogenous mobility shift assay (HMSA) platform and shows the correlation between antibody-to-infliximab (ATI) maturation and NAb formation.

Methods: Serum concentrations of IFX and ATI were measured by HMSA as described in, e.g., PCT Application No. PCT/US2012/025437, filed Feb. 16, 2012, and PCT Publication No. WO 2011/056590, the disclosures of which are hereby incorporated by reference in their entirety for all purposes. For the NAb assay, patient serum containing ATI was first acid dissociated, then two labeled proteins (e.g., IFX-Alexa488 and TNF alpha-Alexa532) were added, followed by neutralization. The solution was diluted to 2% serum, injected by HPLC on a size exclusion column and complexes monitored by fluorescence. The area under the curve (AUC) of the free TNF-Alexa532 peak in each spectrum (e.g., plot or chromatogram) was calculated for controls and patient samples and then a percent NAb calculated. ATI that completely block antigen binding are defined as 100% NAb, 50% means that an equal proportion of ATI in the sample is non-NAb, and 0% means that all ATI is non-NAb. A reference range was established using serum from 75 healthy volunteers. ATI positive serum samples (>3.13 U/mL) from 132 residual IBD patient serum screened for IFX and ATI levels were analyzed for NAb. Positive controls were created using pooled ATI positive patient serum.

For data analysis, a peak detection algorithm is used to find all of the peaks and troughs in each spectrum per experiment. A cubic smoothing spline is fit to each spectrum, and peaks and troughs are defined as a change in the first derivative of the signal. A peak is a sign change of the spectrum's slope from positive to negative. Conversely, troughs are defined as a change in sign from negative to positive. The tallest peak within a window at the expected location of the free TNF-Alexa532 peak (e.g., 11.5 to 13 minutes) is taken to be the free peak itself. The troughs directly above and below the detected free peak define the upper and lower limits of the peak itself. Areas under the bound, free (TNF and IFX) and negative control peaks are found by integrating the peak area within the limits described above using the trapezoid rule. The % of the TNF-Alexa532 peak area is then calculated for each sample by using the formula:

$$\% = [(a-b)/c]*100$$

wherein a=AUC of the TNF-Alexa532 peak in an unknown sample, b=AUC of the TNF-Alexa532 peak from a NAb negative control (e.g., IFX-Alexa488+TNF-Alexa532 in normal human serum), and c=AUC of the free TNF-Alexa532 in normal human serum. For the calculation, "c" is set to 100% and "b" is as close to 0% as possible, although it may vary based on reaction conditions. The range between "b" and "c" defines the maximum window of sensitivity.

Figure 2:
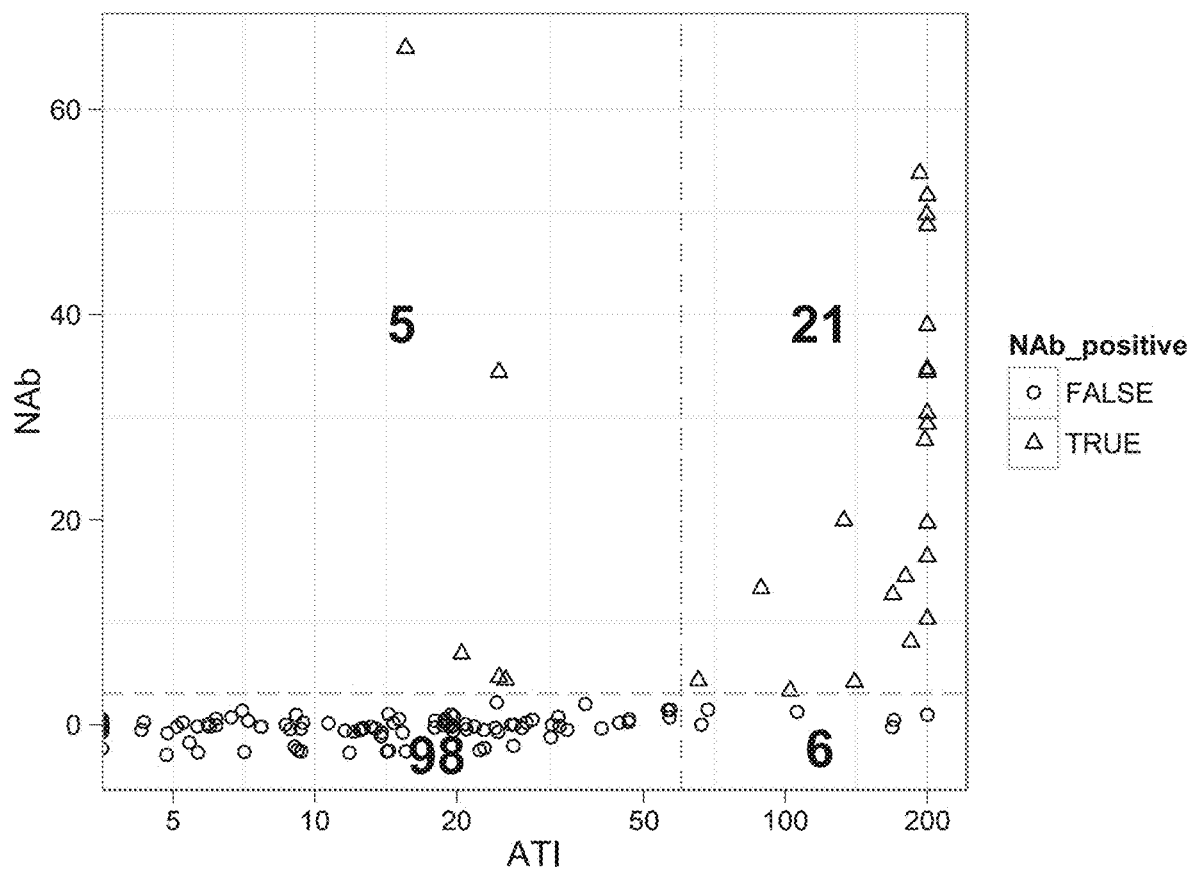
FIG. 2 illustrates that an ATI concentration ≥60 U/ml is predictive of NAb+.
Figure 3:
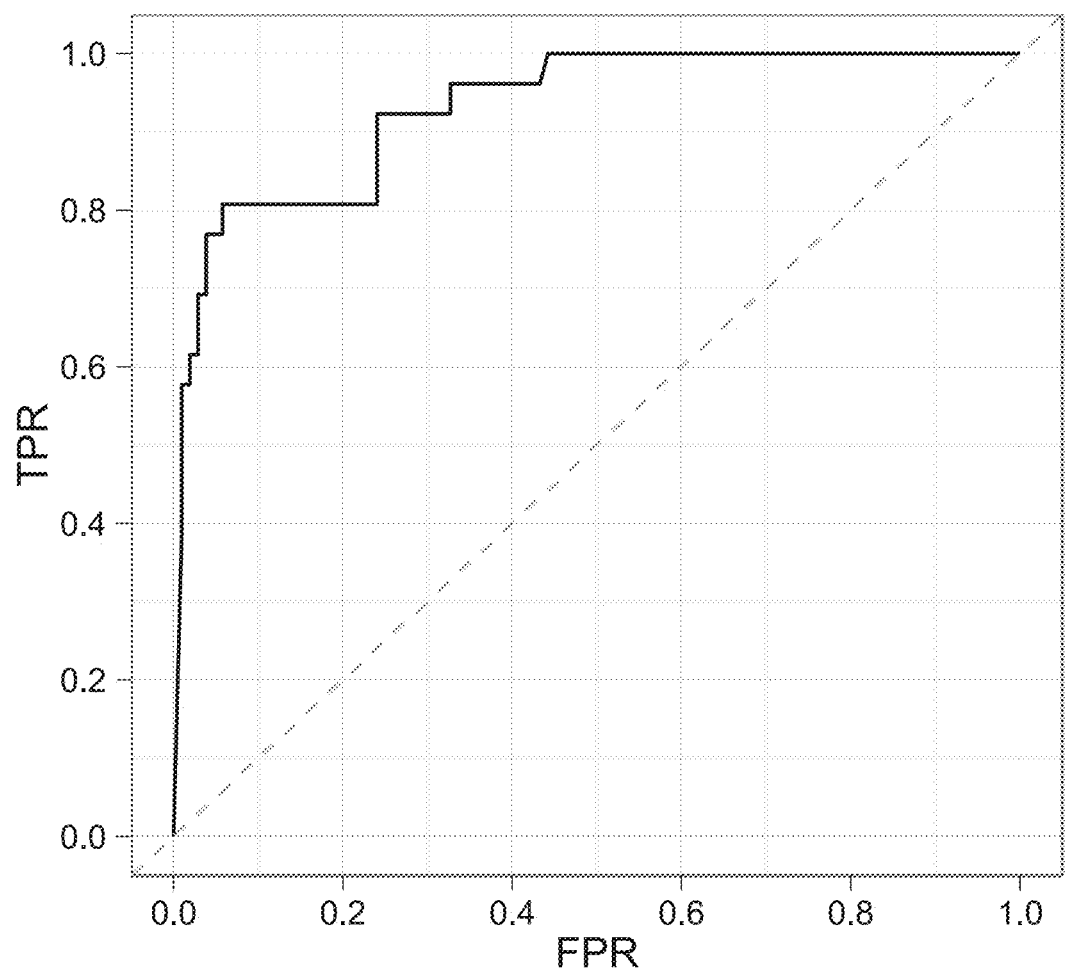
FIG. 3 illustrates that ATI predicts NAb with a ROC AUC of 0.931.

Results: The NAb assay of the invention has demonstrated high reproducibility, accuracy, and precision. The intra- and inter-assay precision is less than 20% of CV, and the accuracy of the assay is within 25%. The precision and accuracy obtained with the NAb assay of the invention is substantially better than cell-based assays or ELISAs. IFX drug tolerance is ~6 µg/mL, while TNFα interferes at greater than 1.0 ng/mL. Positive controls from pooled ATI positive patient serum dilute linearly from 40-5% NAb. Analysis of healthy controls shows that samples that return a value of ≥3% (e.g., 3.06%) are considered NAb positive. More than 30 ATI positive patient serum samples (3.12-199.43 U/mL) were screened for NAb, and 26 out of 132 (19.7%) of the ATI positive patient serum samples were NAb positive (mean 22.47%, range 3.29-51.63%). ATI levels greater than 60 U/mL corresponded to highly neutralizing Ab. Further analysis of NAb positive samples reveals a linear correlation between ATI titer and NAb positivity. In particular, FIG. 1 illustrates that there was a clear relationship between NAb percent (y-axis) and ATI levels (Spearman Rank Correlation, rho=0.564, p <<0.0001). FIG. 2 illustrates that an ATI concentration ≥60 U/ml is predictive of NAb positivity (NAb+). Sensitivity=77.8%; Specificity=98.1%; Odds ratio=63.6, p <<0.0001, Fisher's Exact Test. FIG. 3 illustrates an ATI cutoff analysis and demonstrates that ATI predicts NAb with a ROC AUC of 0.931. True Positive Rate (TPR)=Sensitivity; False Positive Rate (FPR)=1−Specificity.

Conclusion: Monitoring of NAb, in addition to drug and ADA levels, provides necessary information on the ADA response and helps guide early therapeutic intervention. This method can be applied to the characterization of ADA against any biologic therapy.

Example 2. Patient Case Studies for Monitoring the Formation of Neutralizing Anti-Drug Antibodies Over Time.

This example illustrates additional embodiments of a novel homogeneous assay for detecting or measuring the presence or level of neutralizing and/or non-neutralizing anti-drug autoantibodies (ADA) in a patient sample (e.g., serum) using size exclusion chromatography in the presence of labeled (e.g., fluorescently labeled) anti-TNFα drug and labeled TNFα. In addition, this example demonstrates time course case studies of IBD patients on anti-TNFα drug therapy for monitoring the formation of neutralizing and/or non-neutralizing anti-drug antibodies and/or a shift from non-neutralizing to neutralizing anti-drug antibodies while the patient is on therapy.

1. Drug and Anti-Drug Antibody Assays

Figure 4:
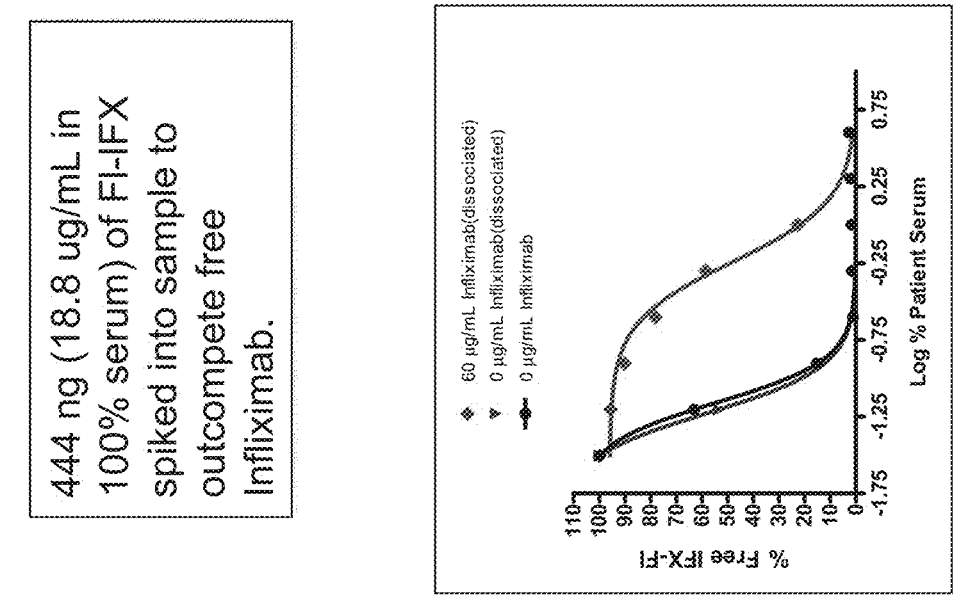
FIG. 4 illustrates detection of ATI by the fluid phase mobility shift assay of the present invention.
Figure 4:
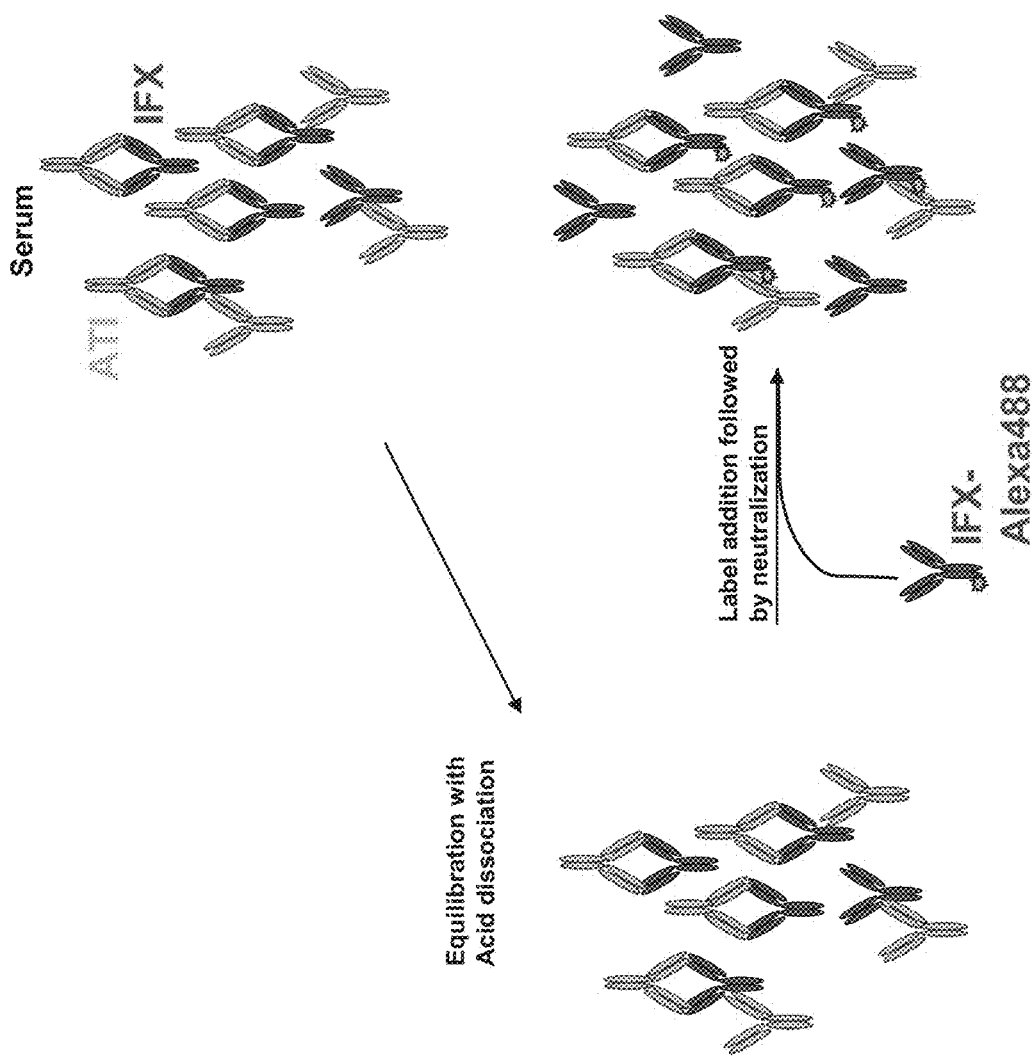

FIG. 4 illustrates detection of ATI (i.e., antibody to IFX; "HACA") by the fluid phase mobility shift assay described herein. For example, 444 ng of Alexa488 labeled IFX (18.8 µg/ml in 100% serum) was spiked into a sample to outcompete free IFX. In particular embodiments, patient serum samples containing complexes of IFX and ATI can be subjected to acid dissociation, wherein equilibration with acid dissociation and label addition followed by neutralization is performed.

Figure 5:
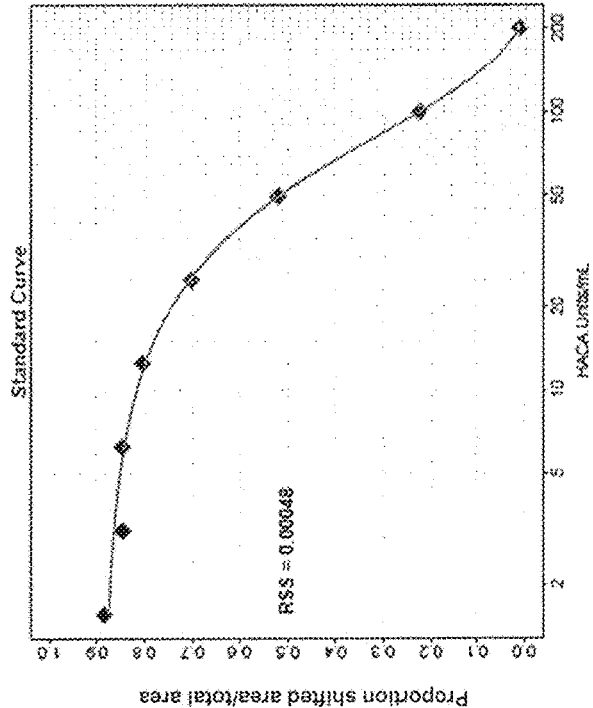
FIG. 5 illustrates an exemplary ATI/IFX fluid phase mobility shift assay of the present invention. Samples containing various concentrations of ATI (standards or unknowns) equilibrated with fluorescently labeled Infliximab (IFX-488) were injected on size exclusion columns in 2% serum. Large IFX-488/ATI complexes eluted first, followed by smaller complexes and then unbound IFX-488 and the Alexa488 loading control. Unknown concentrations were determined by interpolation from a standard curve. Detection of IFX followed a similar methodology.
Figure 5:
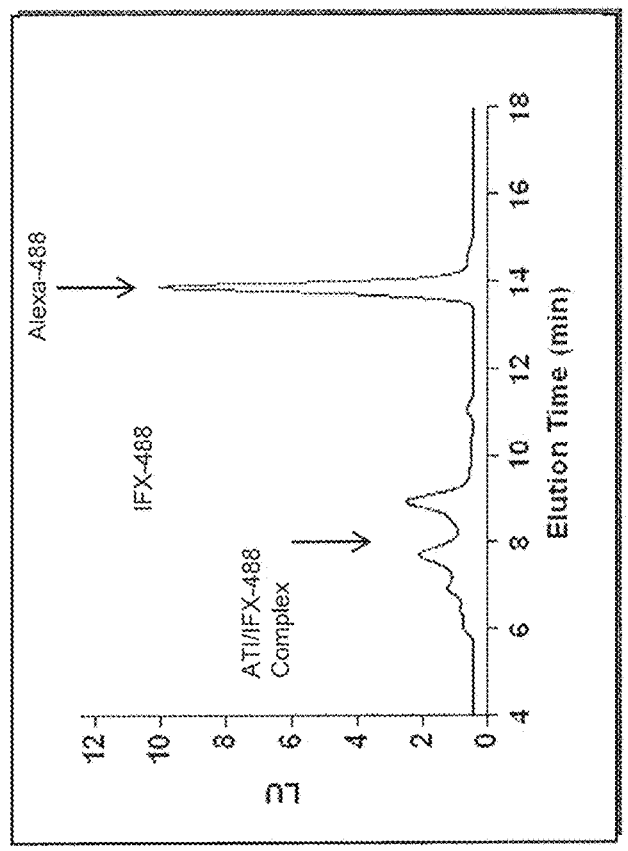

FIG. 5 illustrates an exemplary ATI/IFX fluid phase mobility shift assay of the present invention. For example, samples containing various concentrations of ATI (standards or unknowns) equilibrated with fluorescently labeled Infliximab (IFX-488) were injected on size exclusion columns in 2% serum. FIG. 5 shows that large IFX-488/ATI complexes eluted first, followed by smaller complexes and then unbound IFX-488 and the Alexa488 loading control. Unknown concentrations were determined by interpolation from a standard curve. Detection of IFX followed a similar methodology.

2. Neutralizing and Non-Neutralizing Anti-Drug Antibody Assays

Figure 6:
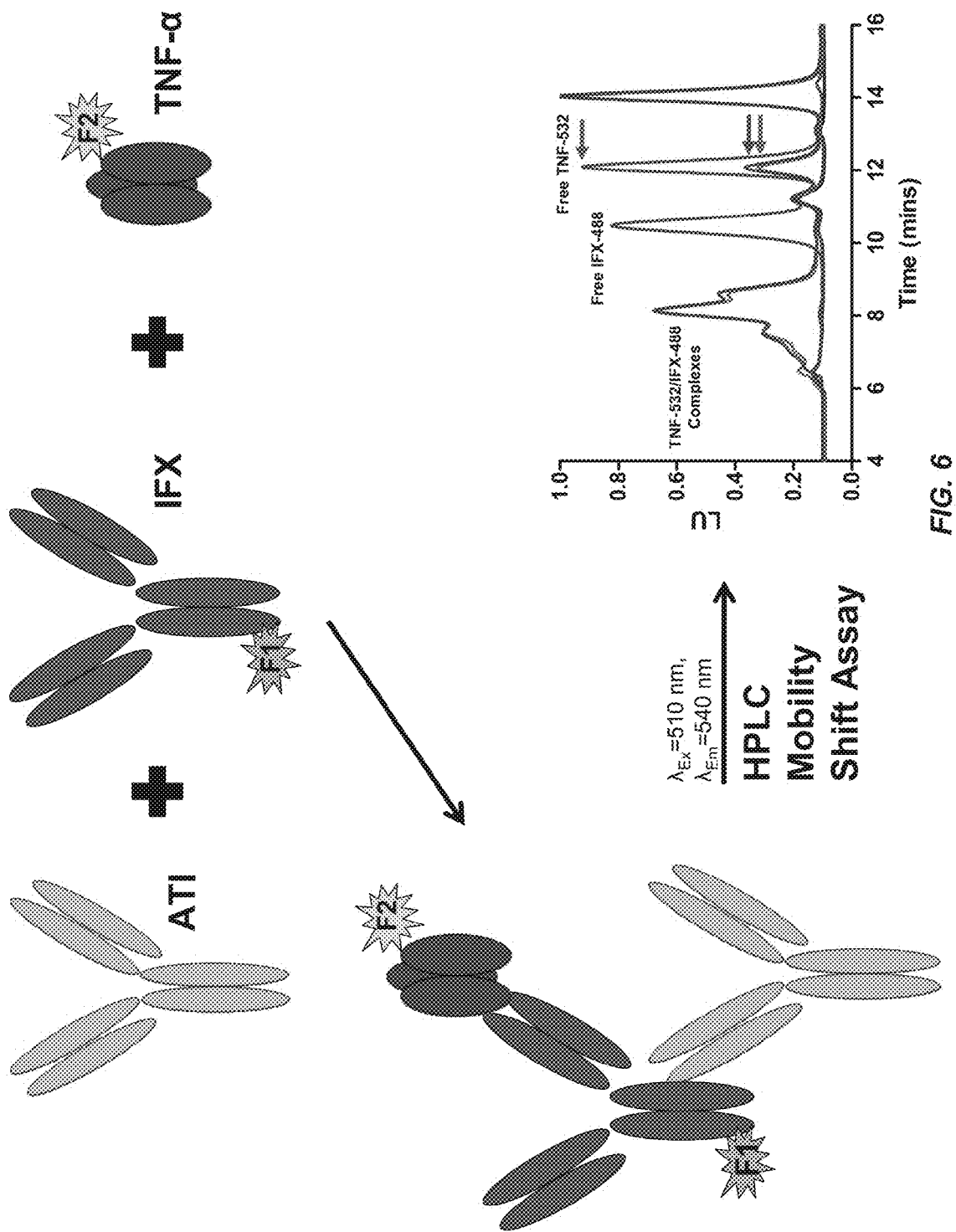
FIG. 6 illustrates a non-neutralizing anti-drug antibody (ADA) assay of the present invention.
Figure 7:
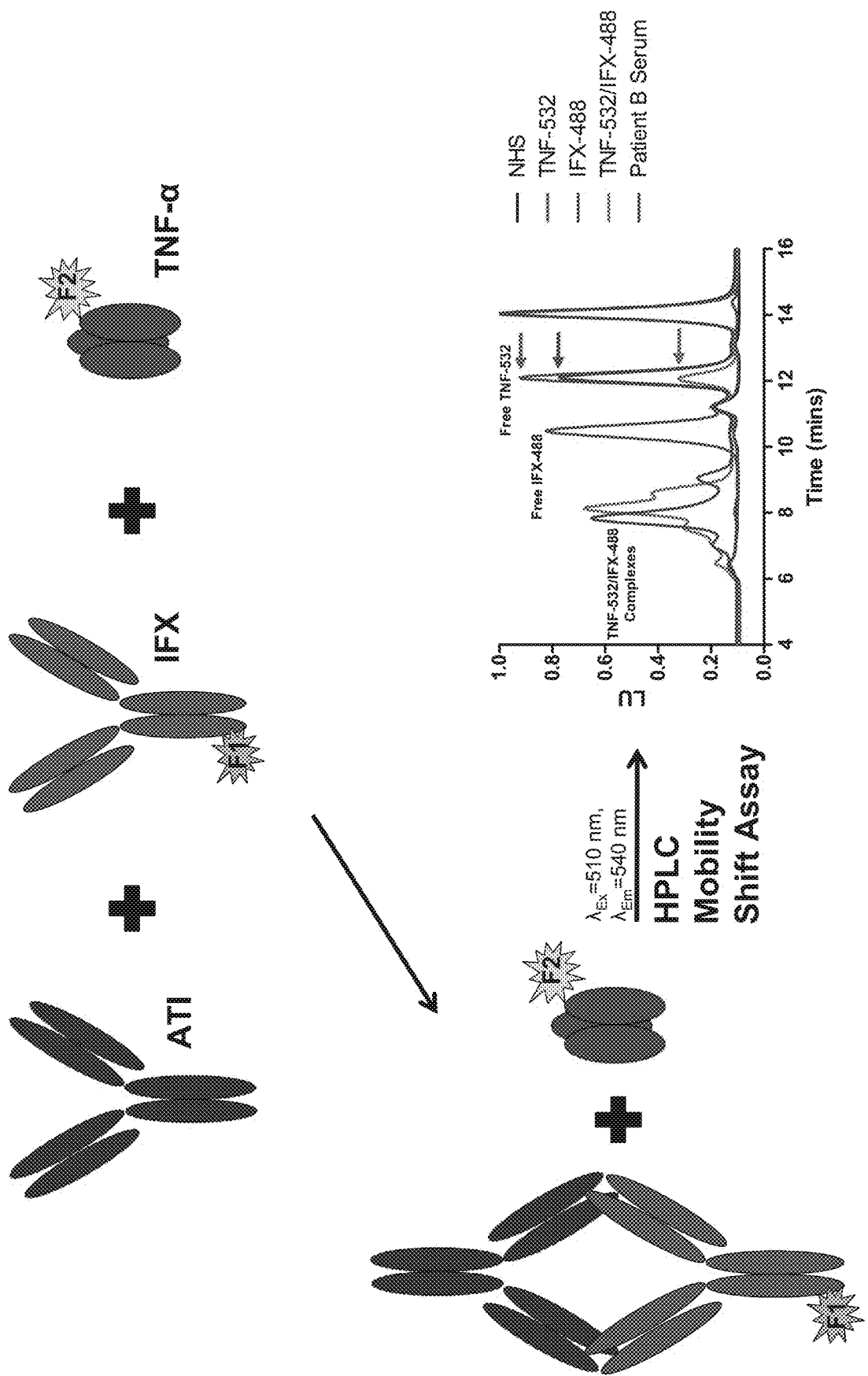
FIG. 7 illustrates a neutralizing ADA assay of the present invention.

FIGS. 6 and 7 illustrate assays of the present invention for determining whether anti-drug antibodies such as ATI are neutralizing or non-neutralizing autoantibodies using size exclusion chromatography to detect the binding of these autoantibodies to fluorescently labeled anti-TNFα drug in the presence of fluorescently labeled TNFα. In one exemplary embodiment, an anti-TNFα drug such as IFX is labeled with a fluorophore "F1", wherein the fluorophore can be detected on either or both the visible and IR spectra. Similarly, TNFα is labeled with a fluorophore "F2", wherein the fluorophore can also be detected on either or both the visible and IR spectra, and wherein "F1" and "F2" are different fluorophores. The labeled anti-TNFα drug and the labeled TNFα are incubated with human serum in a liquid phase reaction to allow the formation of complexes (i.e., immune complexes) between the labeled anti-TNFα drug (e.g., IFX), labeled TNFα, and/or anti-drug antibodies (e.g., ATI) present in the serum.

Following incubation, the samples are loaded directly onto a size exclusion column and subjected to the HPLC mobility shift assay. FIG. 6 illustrates a non-neutralizing anti-drug antibody (ADA) assay of the present invention in which binding of both the anti-drug antibody (e.g., ATI) and the labeled TNFα (e.g., Alexa532 labeled TNFα; "TNF-532") to the labeled anti-TNFα drug (e.g., Alexa488 labeled IFX; "IFX-488") results in a decrease in free TNF-532 levels. FIG. 7 illustrates a neutralizing ADA assay of the present invention in which binding of anti-drug antibody (e.g., ATI) to the labeled anti-TNFα drug (e.g., IFX-488) without binding of the labeled TNFα (e.g., TNF-532) results in substantially the same amount of free TNF-532 levels as the TNF-532 control.

Figure 8:
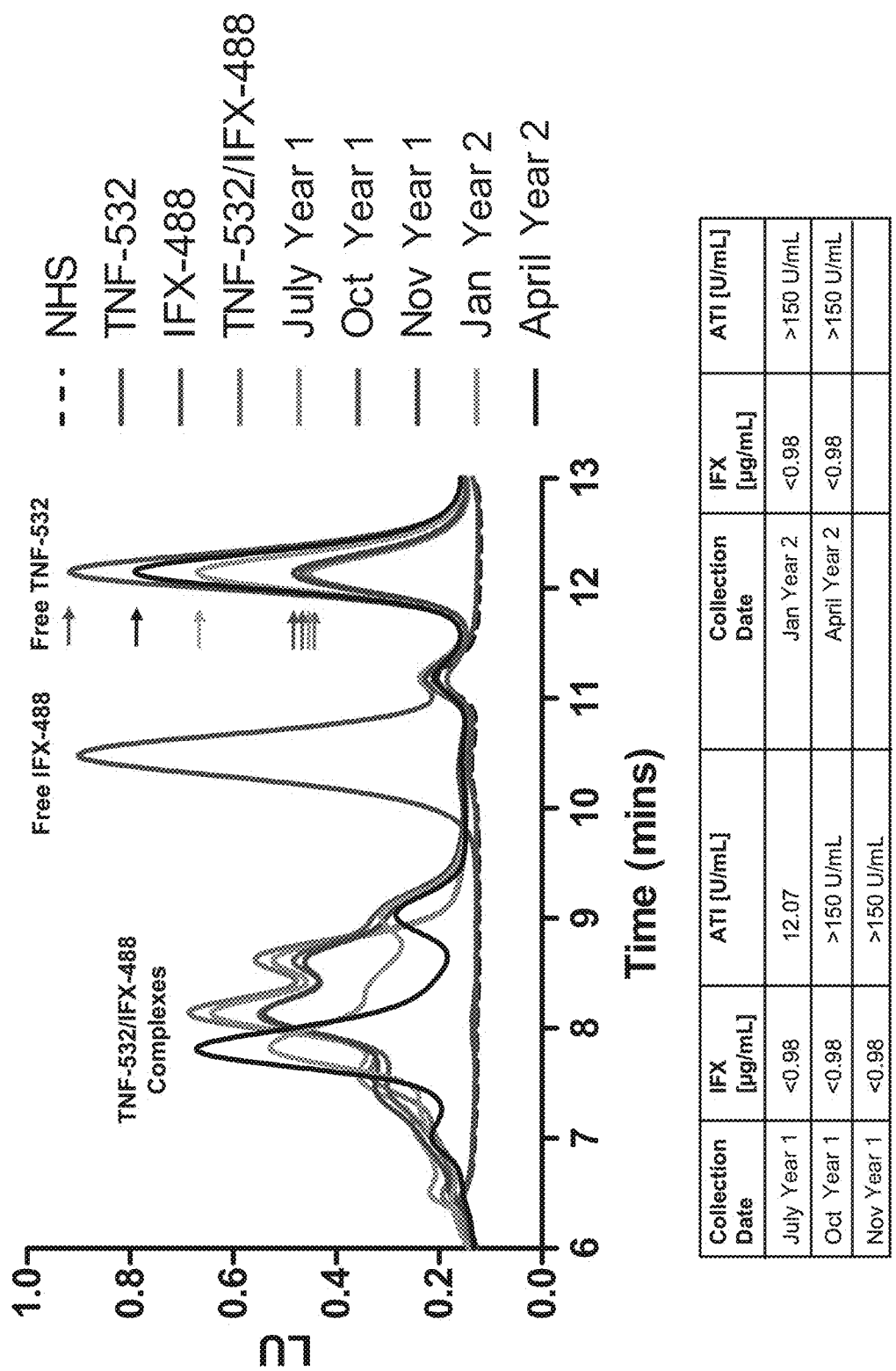
FIG. 8 illustrates the levels of IFX and ATI over a time course of 5 samples from a UC patient taken 1, 2, or 3 months apart.
Figure 9:
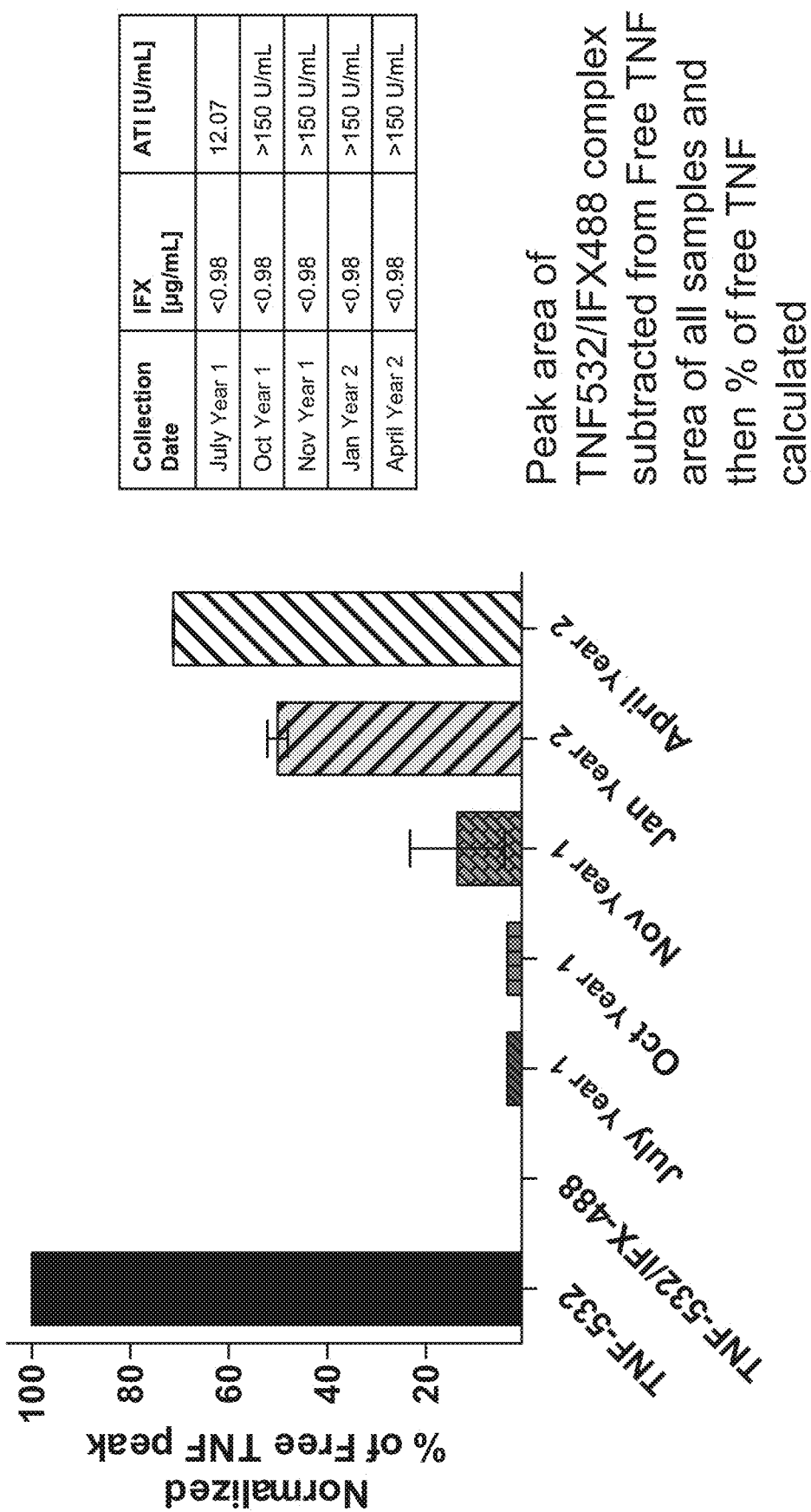
FIG. 9 shows peak analysis to determine the percentage of free TNFα over time in a UC patient.
Figure 10:
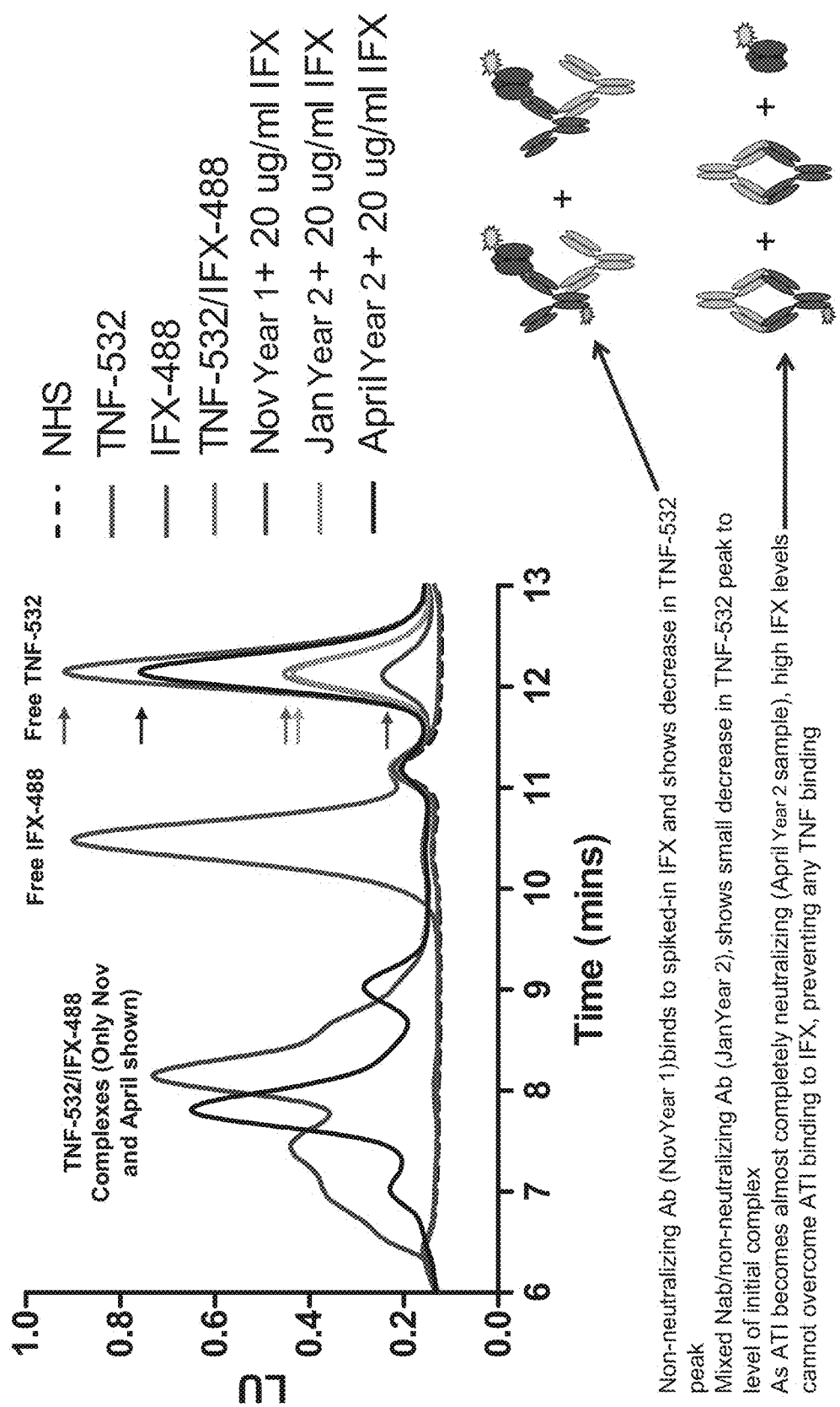
FIG. 10 illustrates a shift from the presence of non-neutralizing autoantibodies to neutralizing autoantibodies over time as exemplified in 3 samples from a UC patient taken 2 or 3 months apart and spiked with IFX.
Figure 11:
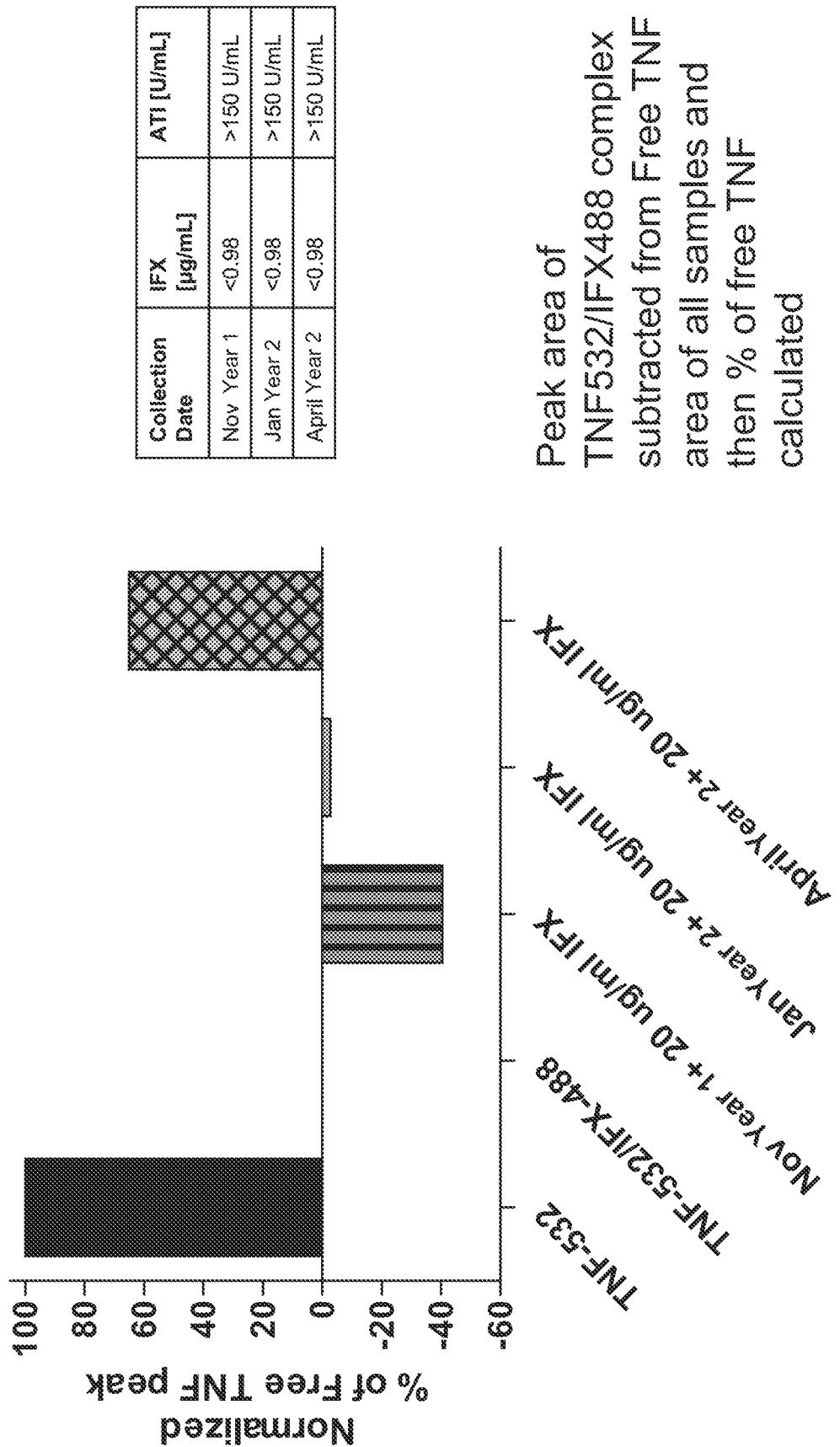
FIG. 11 shows peak analysis to determine the percentage of free TNFα over time in samples from a UC patient that were spiked with IFX.

3. Time Course Studies for Monitoring Neutralizing and Non-Neutralizing Anti-Drug Antibodies FIGS. 8-11 illustrate data from a UC patient case study for determining whether anti-drug antibodies such as ATI are neutralizing or non-neutralizing autoantibodies using the mobility shift assays of the present invention. For example, FIG. 8 illustrates the levels of IFX and ATI over a time course of 5 samples taken 1, 2, or 3 months apart. FIG. 9 shows peak analysis to determine the percentage of free TNFα over time. In particular, the peak area of TNF-532/IFX-488 complexes was subtracted from the free labeled TNFα area of all samples and then % of free TNFα was calculated. Notably, FIG. 9 demonstrates an increase in the level of free TNFα over the time course of 5 samples taken 1, 2, or 3 months apart, indicating an increase in neutralizing autoantibody levels. FIG. 10 illustrates a shift from the presence of non-neutralizing autoantibodies to neutralizing autoantibodies over time as exemplified in 3 samples taken 2 or 3 months apart and spiked with IFX. For the "Nov Year 1" sample, non-neutralizing antibody binds to spiked-in IFX and shows a decrease in the TNF-532 peak. For the "Jan Year 2" sample, a mixture of neutralizing antibody (NAb)/non-neutralizing antibody (Ab) shows a small decrease in the TNF-532 peak relative to the level of the initial complex. As ATI becomes almost completely neutralizing ("April Year 2" sample), high IFX levels cannot overcome ATI binding to IFX, preventing any TNFα binding. As such, FIG. 10 demonstrates a UC patient ATI profile in which the ATI profile shifts from a non-neutralizing ATI profile to a profile containing a mixture of neutralizing ATI and non-neutralizing ATI to a neutralizing ATI profile over the course of IFX therapy. FIG. 11 shows peak analysis to determine the percentage of free TNFα over time in samples that were spiked with IFX. In particular, the peak area of TNF-532/IFX-488 complexes was subtracted from the free TNFα area of all samples and then the percent (%) of free TNFα was calculated. Notably, FIG. 11 demonstrates an increase in the level of free TNFα over the time course of samples taken from the UC patient, indicating an increase in neutralizing autoantibody levels and a shift from non-neutralizing ATI to neutralizing ATI while the patient is on IFX therapy.

Figure 12:
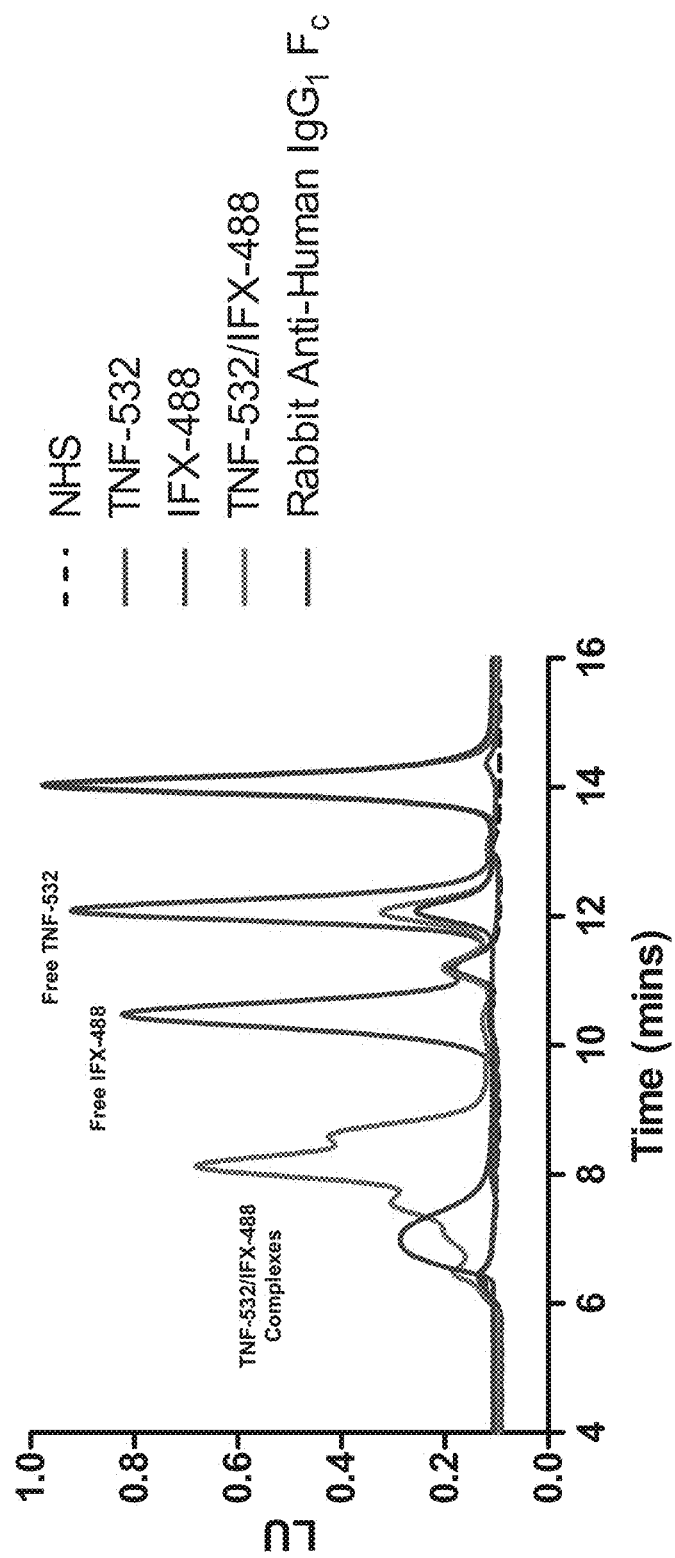
FIG. 12 shows the use of rabbit anti-human IgG1 Fc as a non-neutralizing antibody (Ab) control.
Figure 13:
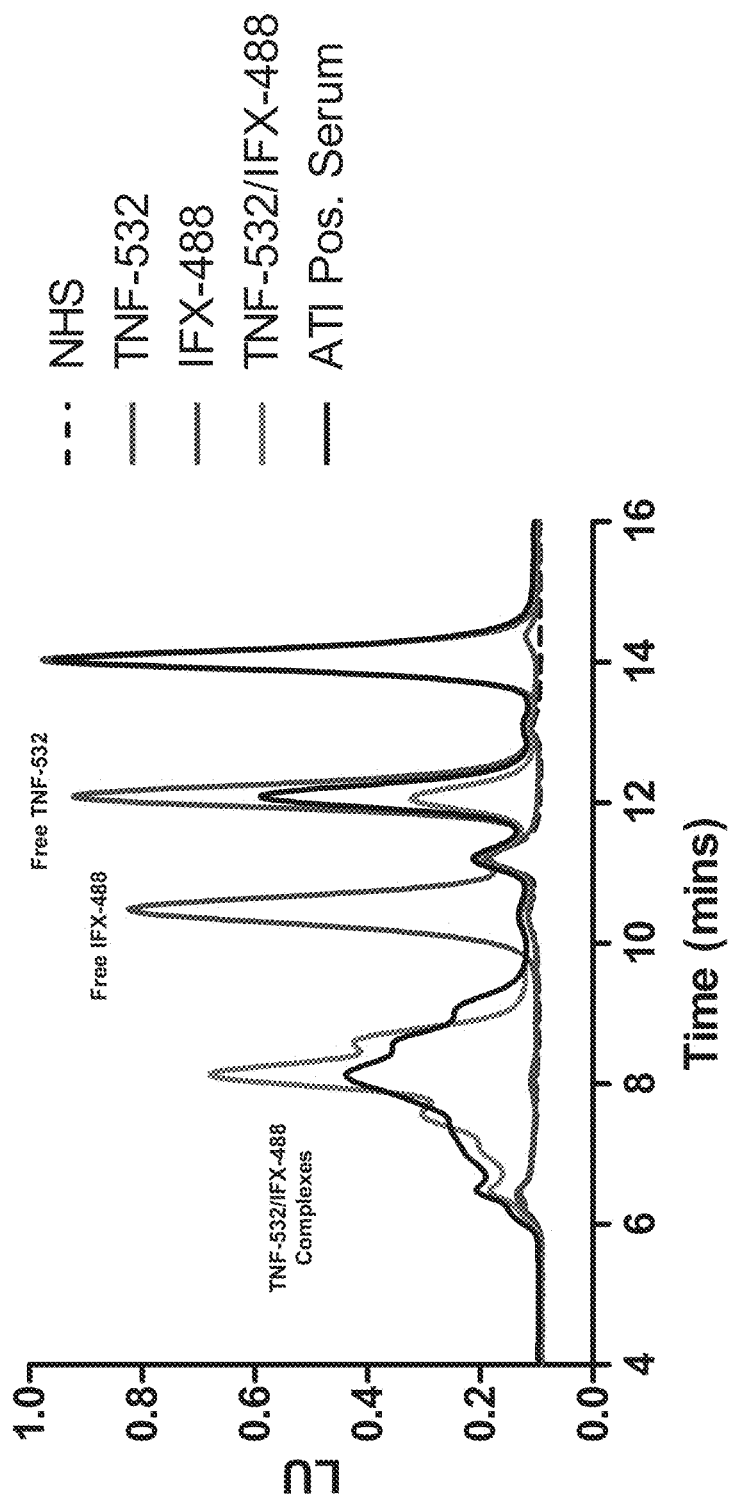
FIG. 13 shows the use of ATI positive serum as a mixed neutralizing antibody (NAb)/non-neutralizing antibody (Ab) control.
Figure 14:
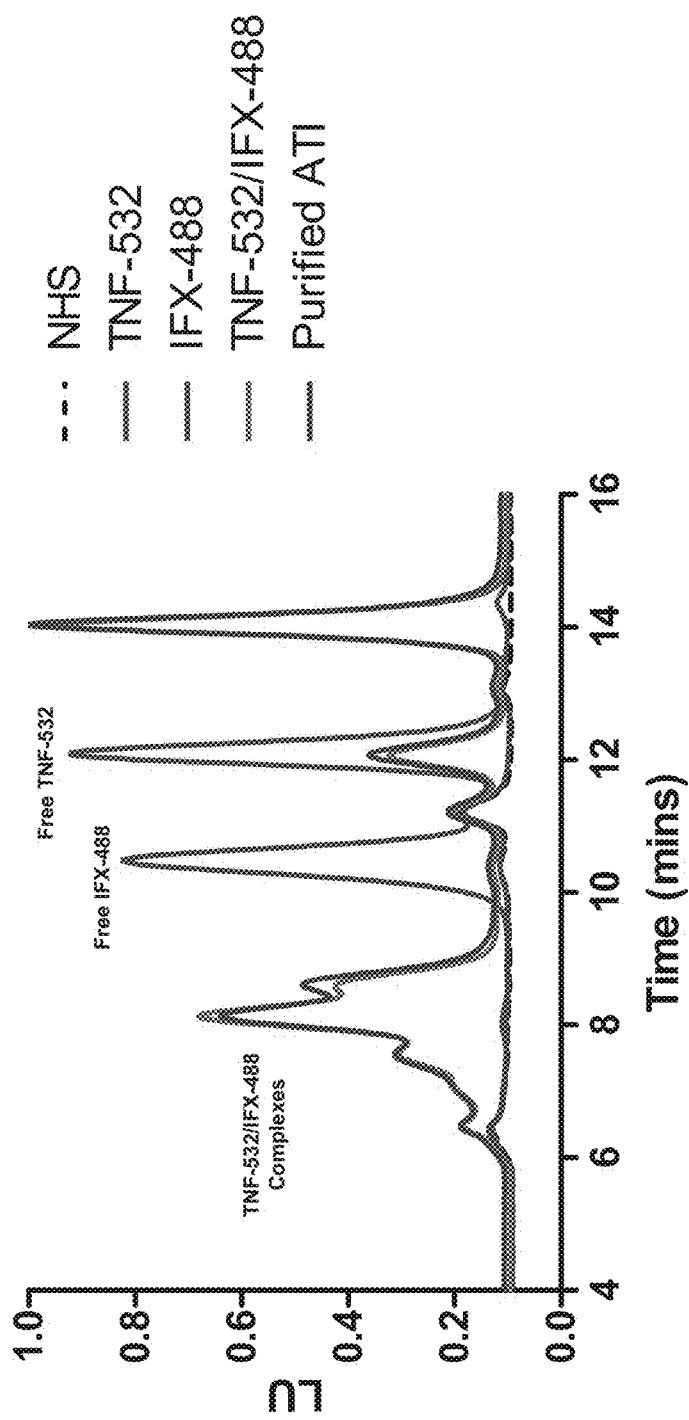
FIG. 14 shows that purification of ATI from ATI positive serum results in loss of weaker affinity NAb.
Figure 15:
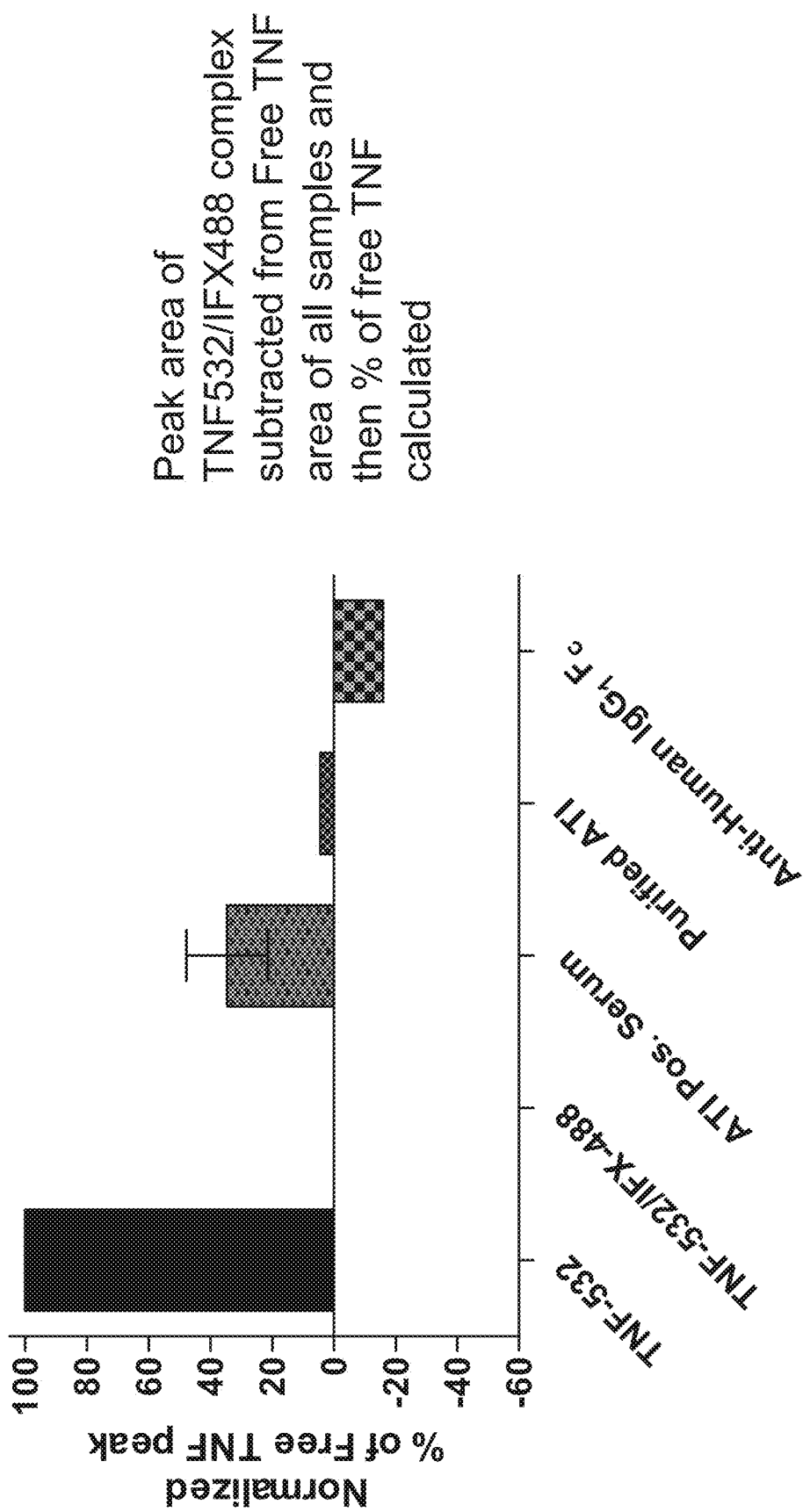
FIG. 15 illustrates peak analysis from a UC patient case study to determine the percentage of free TNFα in these various controls.

FIGS. 12-14 illustrate various controls performed using the mobility shift assays of the present invention. In particular, FIG. 12 shows the use of rabbit anti-human IgG1 Fc as a non-neutralizing antibody (Ab) control. FIG. 13 shows the use of ATI positive serum as a mixed neutralizing antibody (NAb)/non-neutralizing antibody (Ab) control. FIG. 14 shows that purification of ATI from ATI positive serum results in loss of weaker affinity NAb. FIG. 15 illustrates peak analysis from a UC patient case study to determine the percentage of free TNFα in these various controls. In particular, the peak area of the TNF-532/IFX-488 complex was subtracted from the free TNFα area of all samples and then the percent (%) of free TNFα was calculated.

Figure 16:
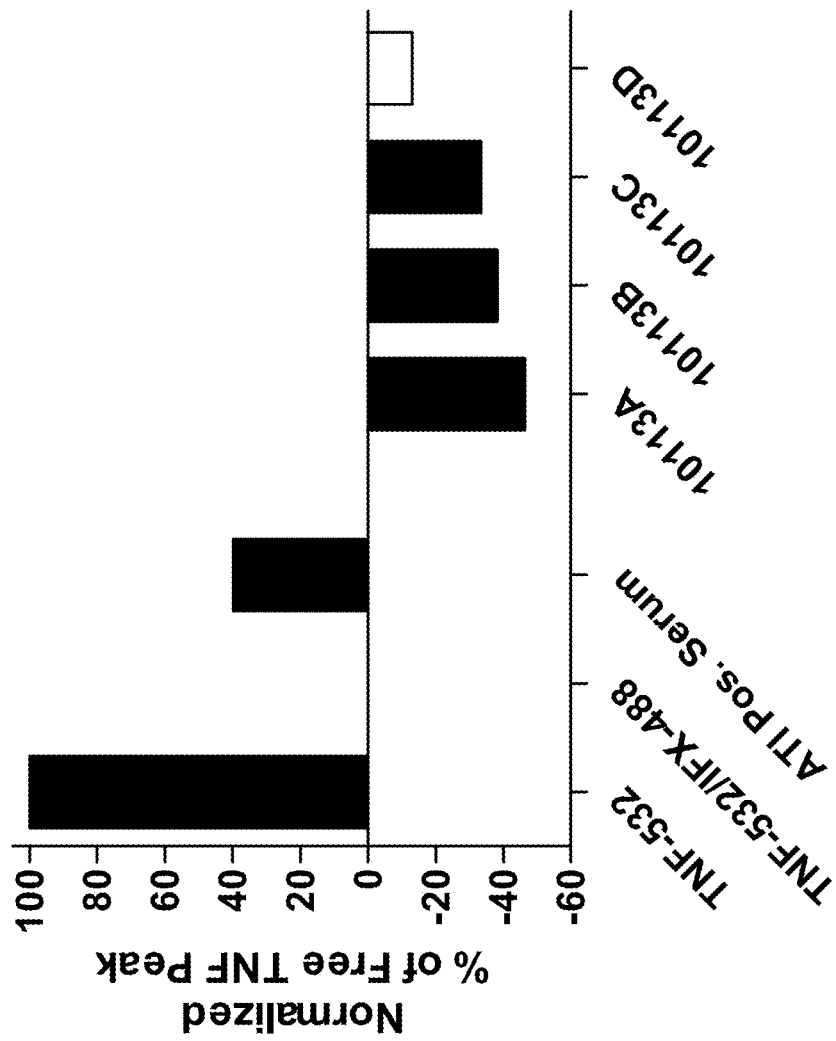
FIG. 16 shows a peak analysis from a CD patient case study to determine the percentage of free TNFα over a time course of 4 samples taken 7 or 8 weeks apart during a 30-week period.
Figure 17:
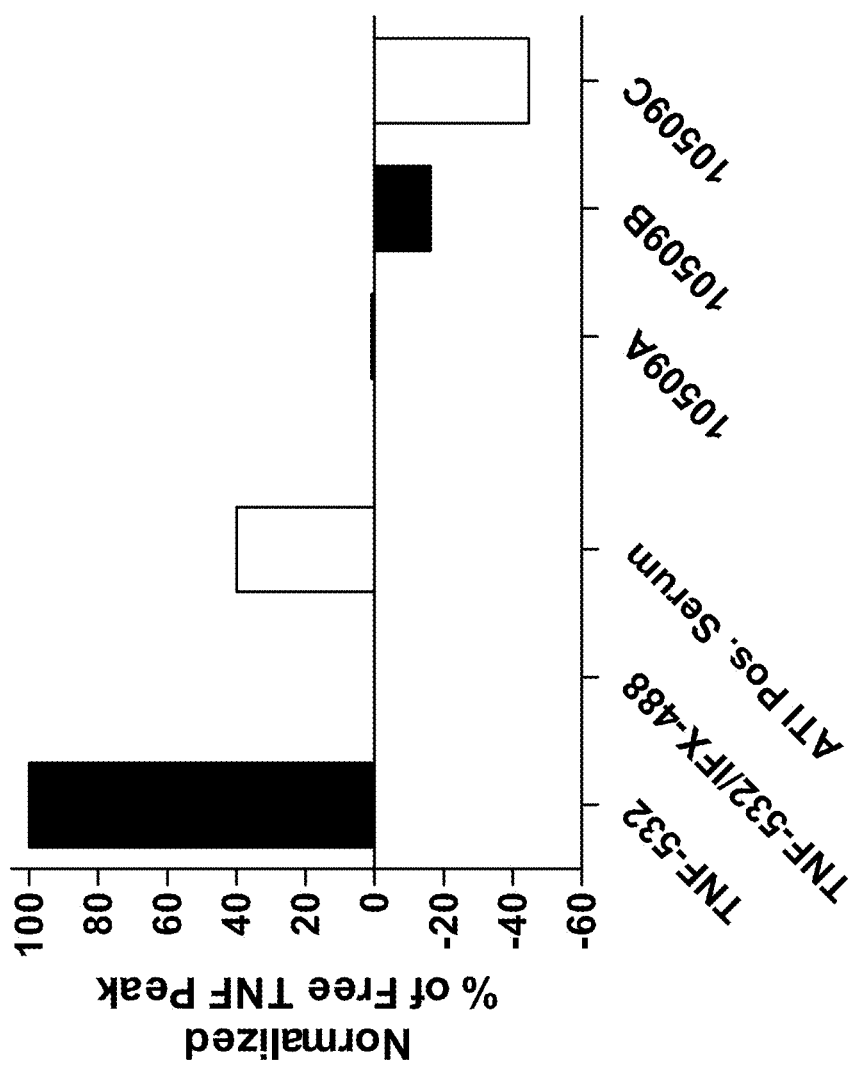
FIG. 17 shows a peak analysis from another CD patient case study to determine the percentage of free TNFα over a time course of 3 samples taken during a 50-week period.
Figure 18:
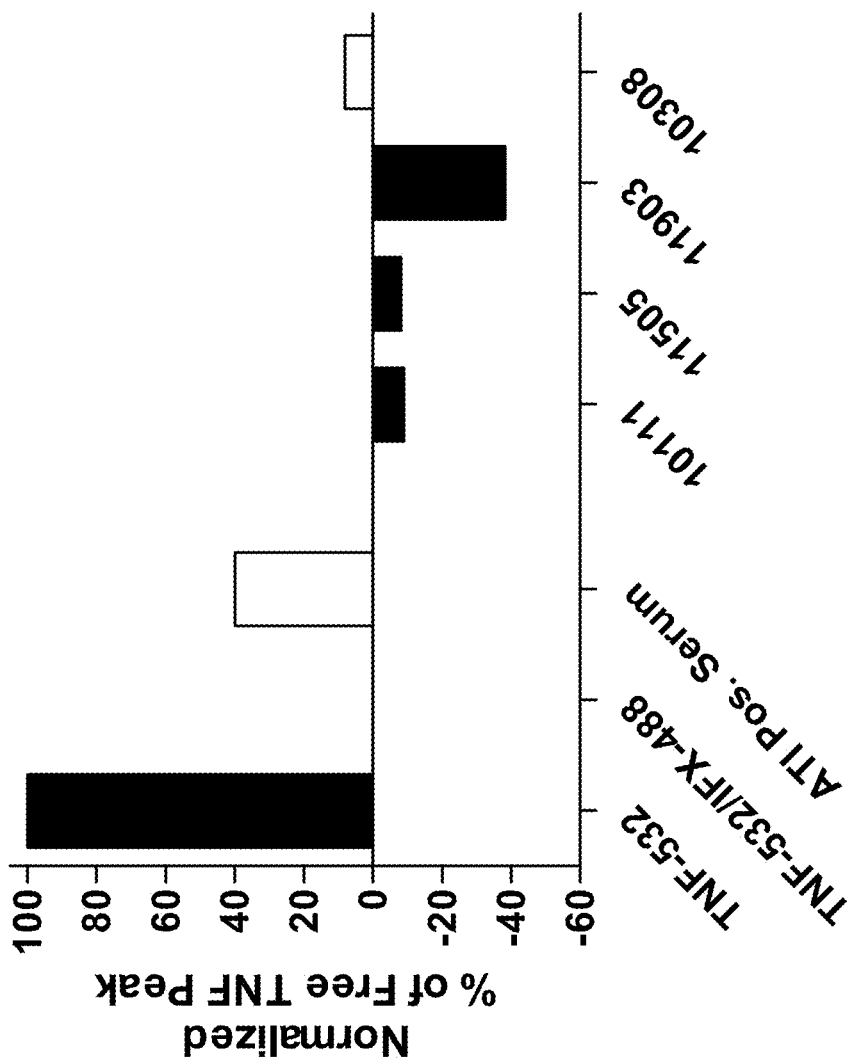
FIG. 18 shows a peak analysis from 4 additional CD patient case studies to determine the percentage of free TNFα in a sample at a particular week during or after induction or maintenance of therapy.

FIGS. 16-18 illustrate data from CD patient case studies for determining whether anti-drug antibodies such as ATI are neutralizing or non-neutralizing autoantibodies using the mobility shift assays of the present invention. For example, FIG. 16 shows a peak analysis from a CD patient case study to determine the percentage of free TNFα over a time course of 4 samples taken 7 or 8 weeks apart during a 30-week period. Moreover, FIG. 17 shows a peak analysis from another CD patient case study to determine the percentage of free TNFα over a time course of 3 samples taken during a 50-week period. In addition, FIG. 18 shows a peak analysis from 4 additional CD patient case studies to determine the percentage of free TNFα in a sample at a particular week during or after induction or maintenance of therapy.

Example 3: Detection of Neutralizing Antibody (NAb) Activity via an HPLC Mobility Shift Competitive Ligand-Binding Assay.

This example illustrates yet additional embodiments of a novel homogeneous assay for detecting or measuring the presence or level of neutralizing and/or non-neutralizing anti-drug autoantibodies (ADA) in a patient sample (e.g., serum) using an HPLC size exclusion chromatography assay. In addition, this example demonstrates methods for predicting and/or determining the cross-reactivity of NAb with alternative biological drugs such as other anti-TNF drugs.

In some embodiments, a multi-tiered approach to immunogenicity testing comprises first screening both drug and anti-drug antibodies by a rapid, sensitive screening assay. This approach is recommended by both the FDA and the EMEA and is a useful management tool for large clinical trials and multiple time points per patient. After confirming the presence of ADA such as ATI, patient samples are then further examined for the presence of neutralizing antibodies that may have significant negative clinical consequences. Neutralizing antibodies interfere with the biological activity by binding to or near the active site, or by induction of conformational changes, inducing a loss of efficacy. Samples containing ATI may also be screened for isotype and epitope specificity. Comparison of patients' clinical responses to product before and following ADA development can provide information on the correlation between ADA development (and antibody characteristics) and clinical responses.

A NAb assay has been developed as disclosed herein that utilizes an HPLC mobility shift assay. In certain embodiments, the multi-tiered approach or test comprises or consists of any one, two, or all three of the following tiers: (1) screening to qualitatively determine if a sample is NAb positive (yes/no based on cutpoint established from analysis of normal human serum); (2) confirming that the sample is NAb positive using, e.g., immunocompetition and/or immunodepletion; and/or (3) predicting and/or determining the cross-reactivity of NAb with alternative biological drugs.

I. Screening Tier

After a patient sample has been confirmed as positive for ADA, it can be screened for NAb. In certain aspects, a subpopulation of ADA is NAb. In certain embodiments, patient serum containing ADA (e.g., antibody to IFX, also known as "ATI" or "HACA") is first acid dissociated with 0.5M citric acid in HPLC water for 1 hr at room temperature (RT). Samples are prepared in a 96 well plate and incubation is conducted in the dark on a plate shaker. Next, two labeled proteins (e.g., drug-Alexa488 (e.g., IFX-Alexa488) and TNFα-Alexa532 in HPLC water containing 0.1% BSA) are added. The samples are neutralized by the addition of 10× PBS, pH 7.3, and incubation for 1 hour at RT in the dark on a plate shaker. The samples are diluted to 2% serum with additional 10X buffer and HPLC water. The samples are then injected by HPLC on a size exclusion column. Complexes or species of differing sizes are separated and monitored by fluorescence, e.g., Free TNFα-Alexa532 ("TNF532"), Free IFX-Alexa488 ("IFX488"), TNF532/

IFX488 complexes, TNF532/IFX488/ATI complexes (non-neutralizing Ab), and ATI/IFX488 complexes (NAb). After comparing the results to negative (see, e.g., FIGS. 12, 19) and positive (see, e.g., FIG. 13) controls along with a cutoff established from normal human sera (e.g., reference range of 3.06% NAb), the sample can be designated as positive or negative for NAb and a titer can be determined.

Figure 19:
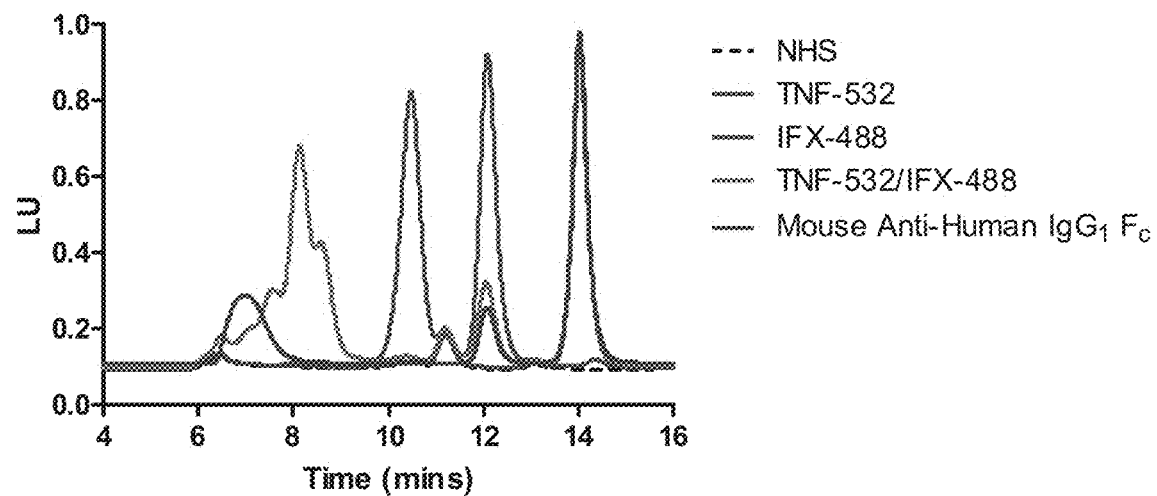
FIG. 19 shows detection of non-neutralizing antibody activity via the mobility shift assay.

FIG. 19 demonstrates detection of non-neutralizing antibody activity via the mobility shift assay. Upon combination of TNF532 with IFX488, there is a shift to the retention time of approximately 8 minutes, indicating the formation of a higher molecular weight complex. The Free IFX-488 peak (around 10.5 minutes) completely disappears and the Free TNF-532 peak (around 12 minutes) almost completely disappears as well (indicating the formation of an ATI/IFX/TNF ternary complex). A non-neutralizing Ab that binds away from the active site of IFX follows a similar pattern. The mouse monoclonal antibody (e.g., around 7 minutes) performs as desired.

FIG. 13 demonstrates detection of neutralizing antibody activity via the mobility shift assay. A completely neutralizing Ab prevents the ability of IFX to bind to TNF (e.g., due to blockage of the active site). This is seen in the chromatogram as a disappearance of the IFX-488 peak with the formation of a higher molecular weight species. The TNF-532 peak will not change. In reality, most patients experience a combination of non-neutralizing/neutralizing Ab as seen in the pooled patient serum in FIG. 13 (ATI Pos. Serum, solid black line). Rabbit polyclonal antibodies against the F(ab')2 fragment of IFX/Humira as an improved NAb positive control are also useful.

FIG. 8 illustrates the development of a NAb response over time in a patient during the course of IFX treatment. While they are positive for ATI at all time points, it is not until the Jan Year 2 (light grey arrow, third from top at ~12 min) time point that NAb develops. The ATI/IFX-488 complexes shift to a slightly different retention time (~7.8 minutes) that indicates a different sized complex as compared to complexes of TNF532/IFX488/ATI (~8.2 and 8.8 mins). Confirmation of neutralizing activity in the presence of additional IFX versus an irrelevant protein (immunocompetition) may be performed as well. Patients such as this would be ideal candidates for treatment adjustment.

FIG. 9 plots the data as a bar graph of the AUC of the % free TNF peak remaining, clearly demonstrating that over time the patient is developing NAb. Even low levels of NAb development observed at early time points are predictive of disease relapse; treatment adjustment for patients displaying this activity is recommended. For example, the patient should be placed on one or more immunosuppressive agents such as methotrexate (MTX) or azathioprine (AZA) while taking the existing anti-TNF drug and/or switched to a different anti-TNF drug.

II. Confirmatory Tier

In the confirmatory tier, drug (e.g., anti-TNFα antibody) is spiked into the sample at a variety of concentrations (e.g., 1-50 µg/mL) to determine the neutralizing capability of the sample. In parallel, non-specific IgG is spiked in at similar levels. The samples spiked with drug should show a dose response to the drug and an EC50 of the NAb can be calculated. Non-specific IgG should have no effect. Immunodepletion can also be performed to rule out the effect of the matrix, if necessary.

FIG. 10 illustrates a shift from the presence of non-neutralizing autoantibodies to neutralizing autoantibodies over time as exemplified in 3 samples taken 2 or 3 months apart and spiked with IFX. Patient serum from each time point responds to spiked-in IFX, showing specificity of response. Over time, the NAb becomes more neutralizing and eventually can neutralize ≥20 µg/mL IFX (the April Year 2 sample does not decrease when IFX is spiked-in). A complete titration can be performed to determine the EC50 of the NAb at each time point.

III. Cross-Reactivity Tier

The cross-reactivity tier is particularly useful for predicting whether a patient will respond to a drug or therapy such as, e.g., an anti-TNFα drug or therapy.

In some embodiments, the present invention provides methods to rapidly determine which therapeutic drugs will or will not work in a patient (e.g., a Crohn's disease, ulcerative colitis, or rheumatoid arthritis patient) based on the ability of an anti-drug antibody (ADA) to cross-react with a series of different anti-TNF therapeutics. As a non-limiting example, one or more of the following drugs may be tested in patients (e.g., Crohn's disease, ulcerative colitis, and/or rheumatoid arthritis patients) that have NAb to Remicade (infliximab): Enbrel (etanercept); Humira (adalimumab); Cimzia (certolizumab pegol); and Simponi (golimumab). After testing positive for NAb with a specific drug (e.g., IFX), the NAb assay can then be performed with a series of other drugs (e.g., fluorescently-labeled drugs) using the method of the initial NAb test described above.

Figure 20:
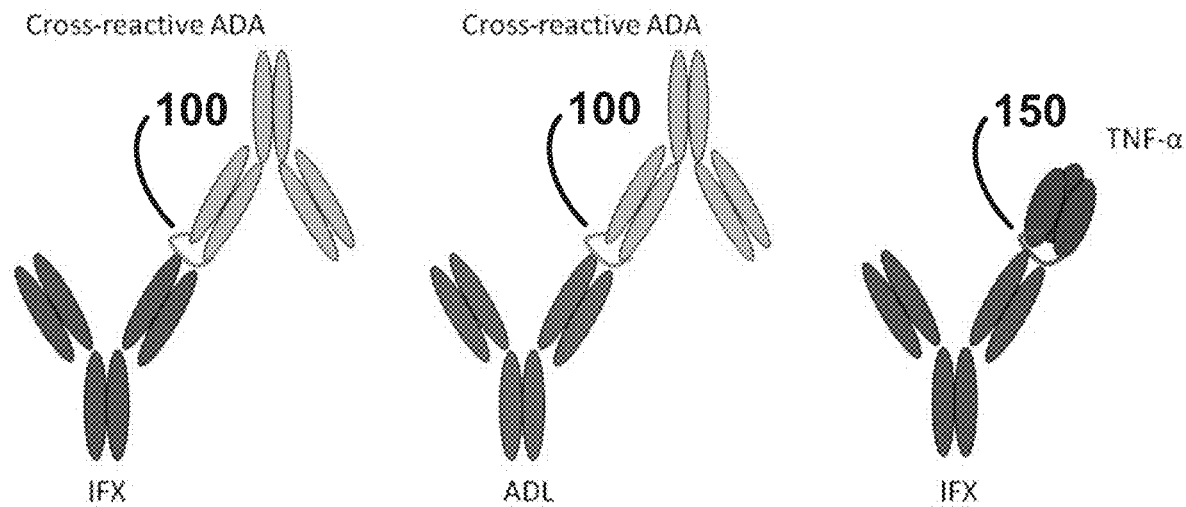
FIG. 20 depicts the cross-reactivity of ADA against both IFX and ADL, wherein the binding site of ADA mimics the binding site of TNFα and can therefore bind to multiple anti-TNF drugs.

The predictive test of the present invention is useful in the management of patient treatment by preventing the use of a drug (e.g., an anti-TNFα drug) that will be neutralized by a patient's antibodies. Without being bound by any particular theory, the sequence of the binding site of the neutralizing ADA has likely developed in such a way to resemble that of TNFα (see, FIG. 20). If the NAb neutralizes any of the other anti-TNF drugs, then those other anti-TNF drugs would likely be a poor alternative to the drug that is already being administered as the patient will likely have an immune response. In some embodiments, a cutoff established from normal human serum can be used to determine if a test sample from a patient is positive or negative. The test can be run in a rapid, cost-effective manner in an in vitro setting.

The following non-limiting case studies included Patients 1 and 2, who were treated with Remicade (infliximab), but who subsequently lost response to Remicade. Patient 1 had UC and Patient 2 had CD. The mobility shift assay described herein clearly demonstrated that Patients 1 and 2 lost response to Remicade as they developed anti-Remicade antibodies (e.g., ATI). These anti-Remicade antibodies were then shown to be neutralizing antibodies (e.g., NAb).

Figure 21:
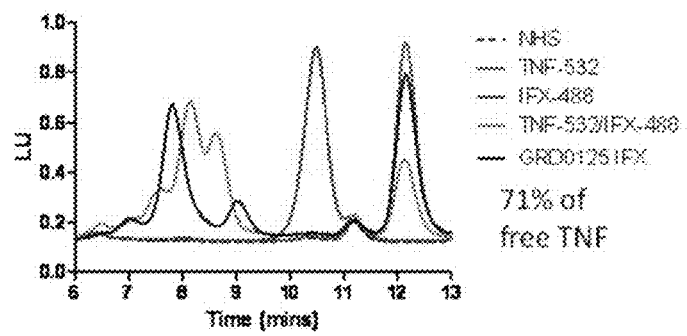
FIG. 21 shows two patient examples (Patients 1 and 2) in which cross-reactivity of NAb produced in response to one anti-TNF drug was determined for other anti-TNF drugs. In particular, NAb which developed when the patient was on Remicade (IFX) were tested against Humira (ADL).
Figure 21:
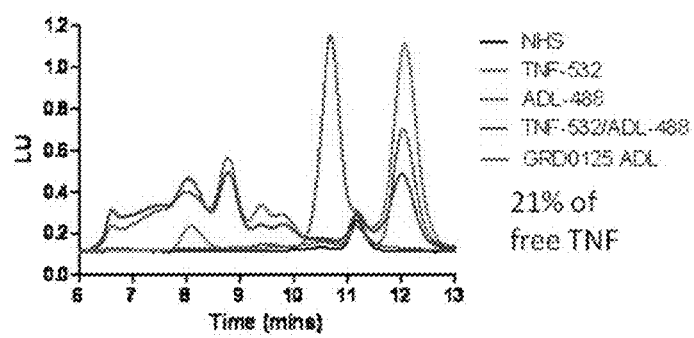
Figure 21:
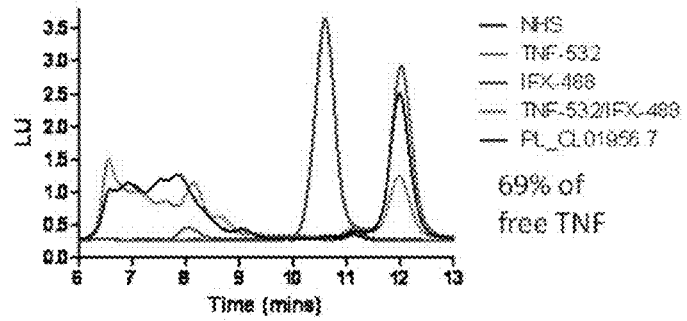
Figure 21:
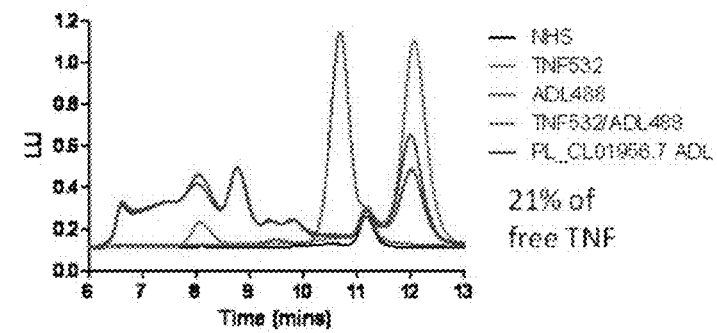

FIG. 21 illustrates that Patients 1 and 2 developed neutralizing antibodies (NAb). These NAb compete with TNFα for the Remicade binding site. Importantly, these NAb might cross-react with other anti-TNF therapeutics. If the NAb cross-react with other anti-TNF therapeutics, changing to another anti-TNF therapeutic will not help these patients. As such, the predictive assays of the present invention provide advantages over current methods of managing patients who lose response to Remicade, in which positive HACA (detectable antibody) is managed by changing to another anti-TNF agent (see, e.g., Afif et al., *Am. J. Gastroenterol.*, 105(5): 1133-9 (2010)).

Figure 22:
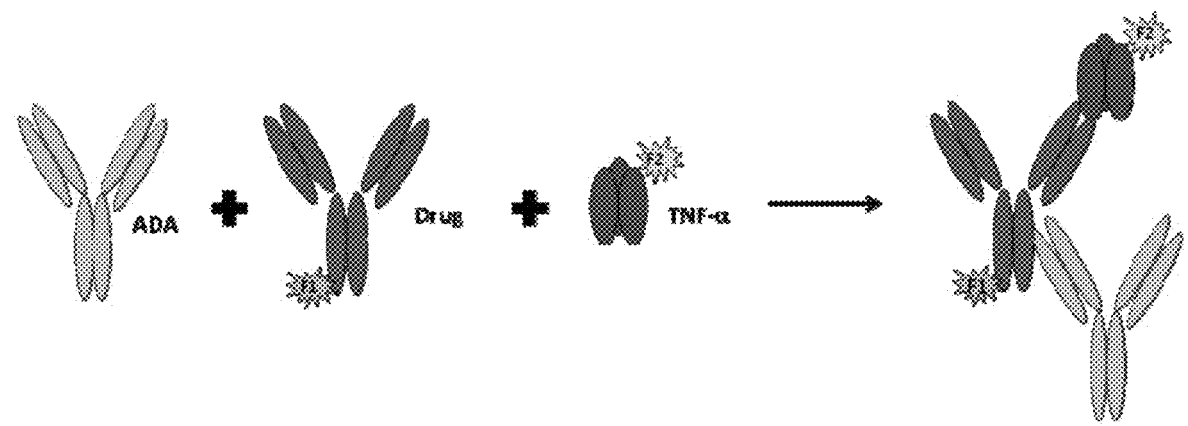
FIG. 22 shows exemplary embodiments of the assays of the present invention to detect the presence of non-neutralizing antibodies (non-NAb) (top) or neutralizing antibodies (NAb) (bottom) against a drug such as IFX or ADL.
Figure 22:
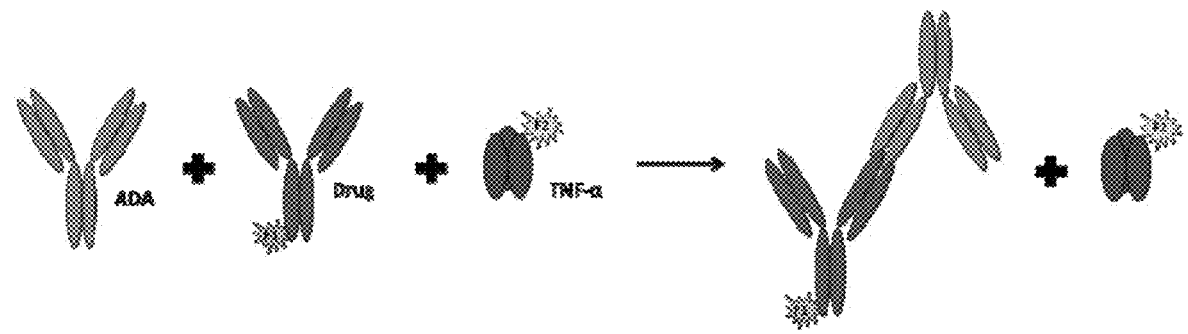

To determine the cross-reactivity of NAb produced in response to one anti-TNF drug with other anti-TNF drugs, NAb which developed when the patient was on Remicade (IFX) were tested against Humira (adalimumab). The data shown in FIG. 21 clearly demonstrated that NAb generated against IFX cross-react with Humira. FIG. 21 illustrates that the free Humira peak (between 10 and 11 minutes, bottom panel of each patient study) is completely shifted to a higher molecular weight when the patient serum containing NAb is added (~12 minutes, patient study #1; ~12 minutes, patient study #2; bottom panel of each patient study). These results indicate that the NAb binds to Humira in such a way that, to an extent, the NAb prevents TNFα from accessing the antigen-binding site of Humira. FIG. 22 depicts this schematically for both NAb and non-NAb determinations.

In certain embodiments, the assay methods of the present invention predict that these patients will not respond to Humira or any other anti-TNF therapeutics. The patient should not be treated with anti-TNF therapy and should be switched to alternative therapy options, including, but not limited to, Actemra, Kineret, Orencia, Rituxan, and/or Arzerra for rheumatoid arthritis (RA), or Tysabri and/or steroids for Crohn's disease (CD).

Accordingly, the methods of the present invention are particularly advantageous for predicting whether a patient will respond to anti-TNFα therapy by determining or measuring the presence and/or concentration level of neutralizing antibodies (NAb) and/or non-NAb in a sample from the patient. In one embodiment, if the sample contains NAb to one anti-TNFα drug, these NAb will likely cross-react and be neutralizing to other anti-TNFα drugs, such that the recommended treatment adjustment for the patient would be to switch to a drug with a different mechanism of action (e.g., a non-anti-TNF agent). In another embodiment, if the sample contains non-neutralizing ADA to one anti-TNFα drug, then the recommended treatment adjustment for the patient would be to switch to another anti-TNFα drug.

Example 4: Assays for Detecting the Presence and Cross-Reactivity of Neutralizing Anti-Drug Antibodies (NAb).

This example illustrates additional embodiments related to the assay methods of the present invention for screening to determine if a sample is NAb positive and predicting and/or determining the cross-reactivity of NAb with alternative biological drugs (see, e.g., Example 3). In particular embodiments, the assay methods described herein are useful for predicting whether a subject receiving a first anti-TNFα drug will respond to alternative anti-TNFα therapy by determining whether a sample obtained from the subject is either positive or negative for NAb. If the sample is positive for NAb, the methods comprise determining whether the NAb will cross-react with a second anti-TNFα drug and recommending that the subject be switched to a non-anti-TNFα drug when the NAb cross-react with the second anti-TNFα drug. If the sample is negative for NAb, the methods comprise recommending that the subject be switched to a second anti-TNFα drug.

Figure 23:
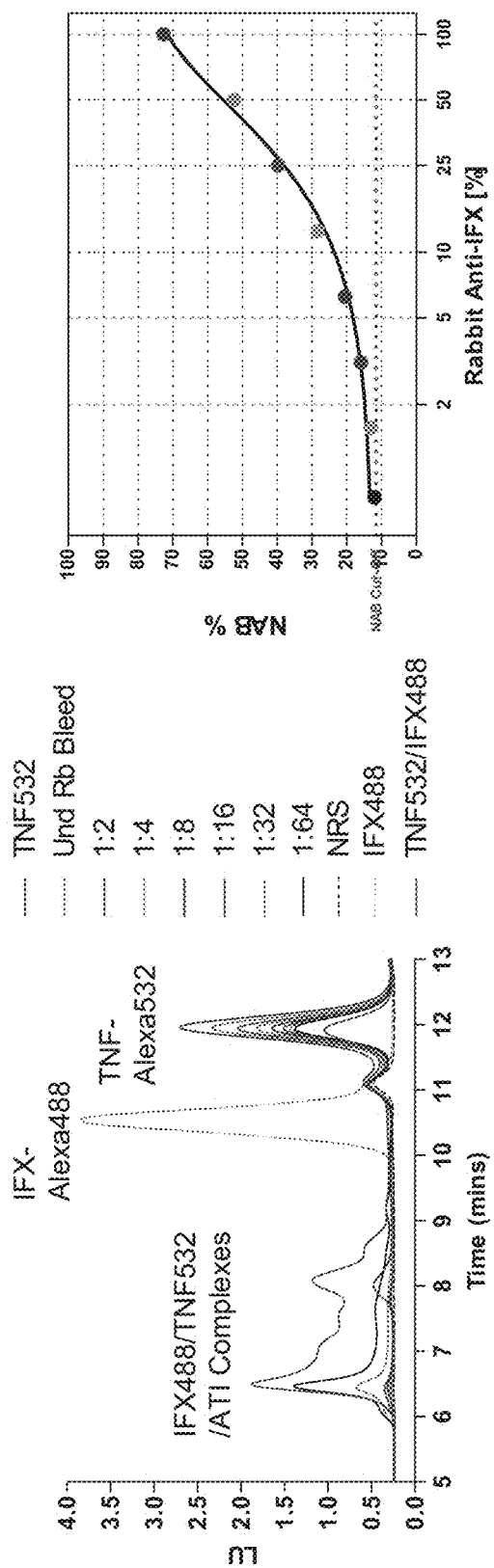
FIG. 23 shows the generation and use of a NAb standard curve.

FIG. 23 shows the generation and use of an exemplary NAb standard curve of the invention. Samples containing various concentrations of rabbit (Rb) anti-IFX antibody (ATI) serum (i.e., standards or unknowns) equilibrated with fluorescently labeled TNF-532/IFX-488 were injected onto size exclusion columns in 2% serum. Large immune complexes eluted first, followed by smaller complexes and then unbound IFX-488 and TNF-532. Unknown concentrations can be determined by interpolation from the standard curve. Rabbit serum containing different mixtures of NAb and non-NAb can be combined to make controls. The NAb assay described herein has an improved cut-off of 2.72% compared to an old cut-off of 11.63% (N=50 normal samples). Table 2 provides a summary of NAb clinical studies by patient.

TABLE 2

NAb Clinical Summary-By Patient

|  | Study 1 n = 154 (290 samples) | Study 2 n = 328 (952 samples) | Study 3 n = 64 (812 samples) | Study 4 |
|---|---|---|---|---|
| ATI+ | 43 | 73 | 58 | 30 |
| (% total) | (28%) | (22%) | (91%) |  |
| NAB+ | 12 | 9 | 3 (23 samples) | 5 |
| (% ATI + tested) | (28%) | (64%) | (60%) | (17%) |
| High Nab activity (20 ug/mL) | 4 | 4 | 2 | 4 |
| (% total) | (2.6%) | (1.2%) | (3.1%) |  |
| (% NAB+) | (33%) | (44%) | (66%) | (80%) |

The cross-reactivity assay methods of the present invention are particularly useful for predicting whether switching to another biological treatment will be beneficial. After finding that a patient is NAb positive to one drug, fluorescently-labeled alternative drugs can be used in the assay. If patient serum still shows neutralizing capability, the new drug will be unlikely to succeed. Such methods are advantageous because they can be used to screen a panel of drugs in a cost-effective and timely manner to enable a suggestion or indication of the best treatment options.

Figure 24:
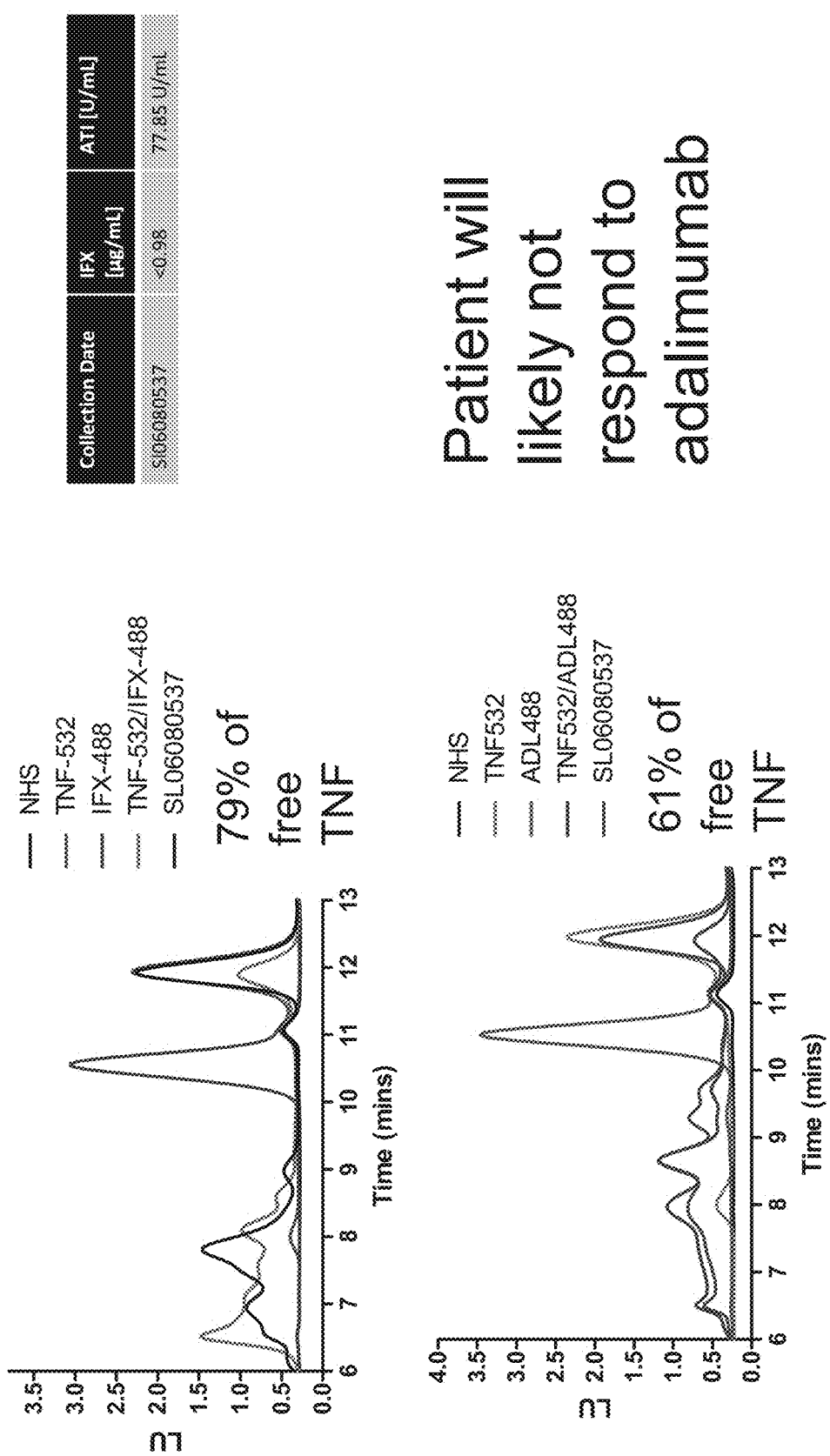
FIG. 24 provides the results of a case study for Patient 3, who was treated with IFX but lost response to IFX, to determine the cross-reactivity of NAb generated against IFX to ADL.
Figure 25:
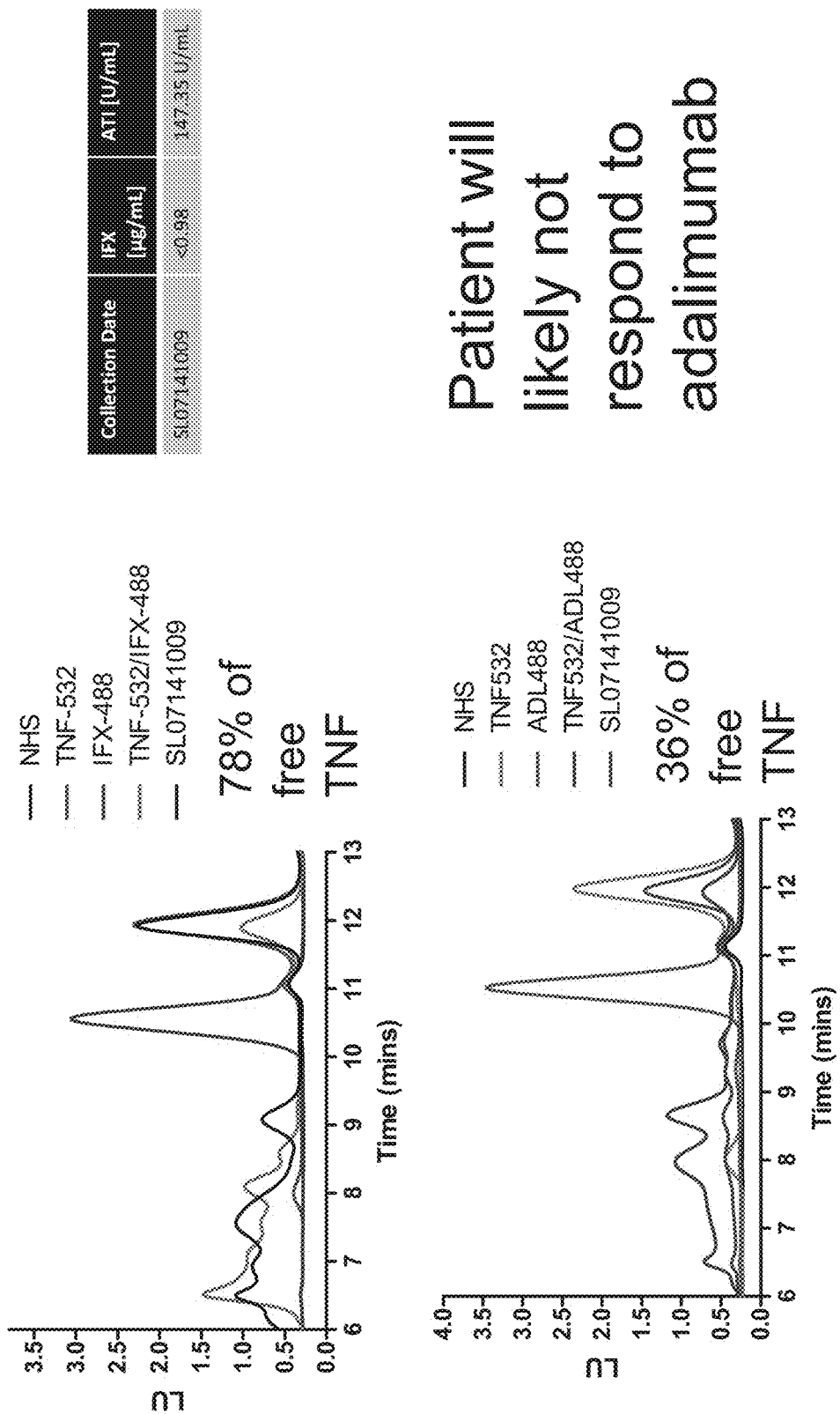
FIG. 25 provides the results of a case study for Patient 4, who was treated with IFX but lost response to IFX, to determine the cross-reactivity of NAb generated against IFX to ADL.

FIGS. 24 and 25 provide additional case studies to the patient studies described in Example 3 and set forth in FIG. 21. In particular, Patients 3 and 4, who were treated with Remicade (infliximab, IFX), but who subsequently lost response to IFX, were identified as being patients who will likely not respond to Humira (adalimumab, ADL) because NAb which developed when the patient was on IFX were determined to be cross-reactive with ADL.

Figure 26:
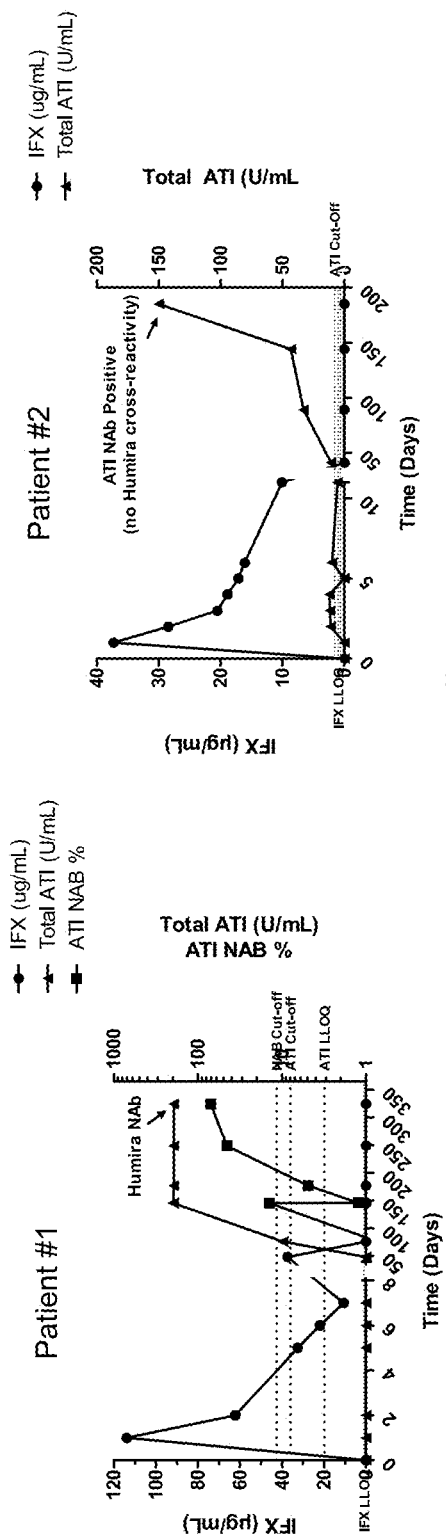
FIG. 26 shows non-limiting examples of patient studies which demonstrate ATI affinity maturation and the development of cross-reactive ATI.
Figure 26:
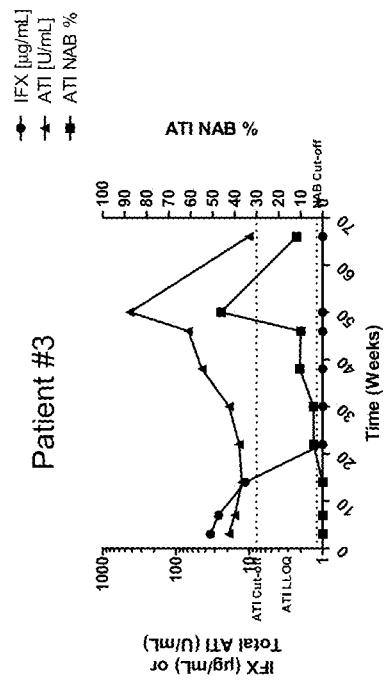

FIG. 26 shows non-limiting examples of patient studies which demonstrate ATI affinity maturation and the development of cross-reactive ATI.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for measuring the level or percent of a neutralizing form of an autoantibody to an anti-TNFα drug in a sample, the method comprising:
   (a) contacting the sample with a labeled anti-TNFα drug and a labeled TNFα to form:
      (i) a first labeled complex of the labeled anti-TNFα drug and the autoantibody; and/or
      (ii) a second labeled complex of the labeled anti-TNFα drug, the labeled TNFα, and the autoantibody;
   (b) subjecting the first labeled complex and/or the second labeled complex to size exclusion chromatography to separate them from free labeled TNFα, free labeled anti-TNFα drug, and/or a complex of labeled anti-TNFα drug and labeled TNFα;
   (c) measuring the level of free labeled TNFα after size exclusion chromatography;
   (d) comparing the level of free labeled TNFα measured in step (c) to a normalized level or percent of free labeled TNFα in a control sample; and
   (e) determining the level or percent of the neutralizing form of the autoantibody in the sample based on the level of free labeled TNFα measured in step (c) compared to the normalized level or percent of free labeled TNFα in the control sample.

2. A method for monitoring or optimizing therapy to an anti-TNFα drug in a subject receiving a course of therapy with the anti-TNFα drug, the method comprising:
(a) detecting or measuring the level or percent of a neutralizing form of an autoantibody to the anti-TNFα drug according to the method of claim 1 at a plurality of time points over the course of therapy;
(b) detecting a change in the level or percent of the neutralizing form of the autoantibody over time; and
(c) determining a subsequent dose of the course of therapy for the subject or whether a different course of therapy should be administered to the subject based upon the change in the level or percent of the neutralizing form of the autoantibody over time.

3. The method of claim 2, wherein the anti-TNFα drug is selected from the group consisting infliximab, etanercept, adalimumab, certolizumab pegol, golimumab, and combinations thereof.

4. The method of claim 2, wherein the autoantibody to the anti-TNFα drug is selected from the group consisting of a human anti-chimeric antibody (HACA), a human anti-humanized antibody (HAHA), a human anti-mouse antibody (HAMA), and combinations thereof.

5. The method of claim 2, wherein the subsequent dose of the course of therapy is increased, decreased, or maintained based upon the change in the level or percent of the neutralizing form of the autoantibody over time.

6. The method of claim 2, wherein the different course of therapy comprises a different anti-TNFα drug, the current course of therapy along with an immunosuppressive agent, or switching to a course of therapy that is not an anti-TNFα drug.

7. The method of claim 6, wherein the different course of therapy is administered when the level or percent of the neutralizing form of the autoantibody increases over time.

8. A method for optimizing therapy and/or reducing toxicity in a subject receiving a course of therapy with a first anti-TNFα drug, the method comprising:
(a) determining whether a neutralizing form of an autoantibody to the first anti-TNFα drug is cross-reactive with a second anti-TNFα drug by detecting or measuring the level or percent of a neutralizing form of the autoantibody in a sample from the subject according to the method of claim 1; and
(b) determining that a different course of therapy should be administered to the subject if the neutralizing form of the autoantibody is cross-reactive with the second anti-TNFα drug.

9. The method of claim 8, wherein the first and second anti-TNFα drugs are independently selected from the group consisting of infliximab, etanercept, adalimumab, certolizumab pegol, golimumab, and combinations thereof.

10. The method of claim 8, wherein the autoantibody to the first anti-TNFα drug is selected from the group consisting of a human anti-chimeric antibody (HACA), a human anti-humanized antibody (HAHA), a human anti-mouse antibody (HAMA), and combinations thereof.

11. The method of claim 8, wherein the different course of therapy comprises switching to a course of therapy that is not an anti-TNFα drug.

12. The method of claim 11, wherein the non-anti-TNFα drug is selected from the group consisting of an IL-6 receptor-inhibiting monoclonal antibody, anti-integrin molecule, JAK-2 inhibitor, tyrosine kinase inhibitor, nutrition therapy, and mixtures thereof.

13. The method of claim 8, wherein the method further comprises determining that a subsequent dose of the current course of therapy should be increased or decreased, or that a different course of therapy should be administered to the subject, if the neutralizing form of the autoantibody is not cross-reactive with the second anti-TNFα drug.

14. The method of claim 1, wherein step (a) comprises adding the labeled anti-TNFα drug and the labeled TNFα to the sample together.

15. The method of claim 1, wherein the level or percent of the neutralizing form of the autoantibody in the sample is determined separately from a level or percent of a non-neutralizing form of the autoantibody in the sample.

* * * * *